United States Patent
Chough et al.

(10) Patent No.: US 10,407,430 B2
(45) Date of Patent: Sep. 10, 2019

(54) JANUS KINASE 1 SELECTIVE INHIBITOR AND PHARMACEUTICAL USE THEREOF

(71) Applicants: YANG JI CHEMICAL CO., LTD., Suwon-si, Gyeonggi-do (KR); HAN WHA PHARMA CO., LTD., Chuncheon-si, Gangwon-do (KR)

(72) Inventors: Chieyeon Chough, Suwon-si (KR); Sunmin Lee, Hwaseong-si (KR); Misuk Joung, Suwon-si (KR); Hyun Uk Jeong, Suwon-si (KR); Hong-sik Moon, Suwon-si (KR)

(73) Assignees: YANG JI CHEMICAL CO., LTD., Suwon-si, Gyeonggi-do (KR); HAN WHA PHARMA CO., LTD., Chuncheon-si, Gangwon (KR)

( * ) Notice: Subject to any disclaimer, the term of this patent is extended or adjusted under 35 U.S.C. 154(b) by 0 days.

(21) Appl. No.: 15/752,635

(22) PCT Filed: Aug. 19, 2016

(86) PCT No.: PCT/KR2016/009205
§ 371 (c)(1),
(2) Date: Feb. 14, 2018

(87) PCT Pub. No.: WO2017/034245
PCT Pub. Date: Mar. 2, 2017

(65) Prior Publication Data
US 2018/0237440 A1    Aug. 23, 2018

(30) Foreign Application Priority Data
Aug. 21, 2015 (KR) .................. 10-2015-0118268

(51) Int. Cl.
| | |
|---|---|
| *A61K 31/519* | (2006.01) |
| *C07D 487/04* | (2006.01) |
| *C07D 403/12* | (2006.01) |
| *A61K 31/506* | (2006.01) |
| *A61P 29/00* | (2006.01) |
| *A61P 37/00* | (2006.01) |

(52) U.S. Cl.
CPC .......... *C07D 487/04* (2013.01); *A61K 31/506* (2013.01); *A61K 31/519* (2013.01); *A61P 29/00* (2018.01); *A61P 37/00* (2018.01); *C07D 403/12* (2013.01)

(58) Field of Classification Search
CPC .......................... A61K 31/519; C07D 487/04
USPC ....................... 514/265.1; 544/280
See application file for complete search history.

(56) References Cited

U.S. PATENT DOCUMENTS

| | | | |
|---|---|---|---|
| 6,956,041 B2 | 10/2005 | Blumenkopf et al. | |
| 6,962,993 B2 | 11/2005 | Blumenkopf et al. | |
| 7,842,699 B2 | 11/2010 | Blumenkopf et al. | |

FOREIGN PATENT DOCUMENTS

| | | |
|---|---|---|
| JP | 2003-516405 A | 5/2003 |
| JP | 2004-501922 A | 1/2004 |
| WO | WO 99/65908 A1 | 12/1999 |
| WO | WO 2006/069080 A2 | 6/2006 |
| WO | WO 2014/101295 A2 | 7/2014 |
| WO | WO 2014/140310 A1 | 9/2014 |
| WO | WO 2015/083028 A1 | 6/2015 |

OTHER PUBLICATIONS

Cheng et al., "Relationship between the inhibition constant ($K_I$) and the concentration of inhibitor which causes 50 per cent inhibition ($I_{50}$) of an enzymatic reaction," *Biochem. Pharmacol.*, 22(23): 3099-3108 (1973).

Flanagan, et al., "Discovery of CP-690,550: A Potent and Selective Janus Kinase (JAK) Inhibitor for the Treatment of Autoimmune Diseases and Organ Transplant Rejection", *J. Med. Chem.*, 53(24): 8468-8484 (2010).

Haan et al., "Jak1 Has a Dominant Role over Jak3 in Signal Transduction through γc-Containing Cytokine Receptors," *Chem. Biol.*, 18(3): 314-323 (2011).

(Continued)

*Primary Examiner* — Jeffrey H Murray
(74) *Attorney, Agent, or Firm* — Leydig, Voit & Mayer

(57) ABSTRACT

Provided are Janus kinase 1 selective inhibitors of Formula 1 or Formula 2:

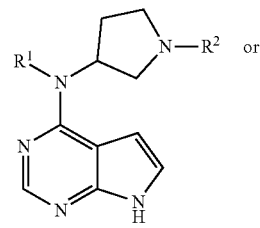

(Formula 1)

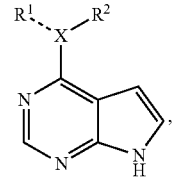

(Formula 2)

wherein $R^1$, $R^2$, and X are as described herein. Pharmaceutical uses thereof, for example, for the treatment of a disease associated with a Janus kinase, are also provided.

18 Claims, 2 Drawing Sheets
Specification includes a Sequence Listing.

(56) References Cited

OTHER PUBLICATIONS

International Bureau, International Search Report in International Application No. PCT/KR2016/009205, dated Dec. 2, 2016.
Kawahara et al., "Critical role of the interleukin 2 (IL-2) receptor γ-chain-associated Jak3 in the IL-2-induced c-fos and c-myc, but not bcl-2, gene induction," *Proc. Natl. Acad. Sci. U.S.A.*, 92(19): 8724-8728 (1995).
Kulagowski et al., "Identification of Imidazo-Pyrrolopyridines as Novel and Potent JAK1 Inhibitors," *J. Med. Chem.*, 55(12): 5901-5921 (2012).
Norman "Selective JAK inhibitors in development for rheumatoid arthritis," *Expert Opin. Investig. Drugs*, 23(8): 1067-1077 (2014).
Nosaka et al., "Defective Lymphoid Development in Mice Lacking Jak3," *Science*, 270(5237): 800-802 (1995).
Papageorgiou et al., "Is JAK3 a new drug for immunomodulation-based therapies?" *Trends Pharmacol. Sol.*, 25(11): 558-562 (2004).
Parganas et al., "Jak2 Is Essential for Signaling through a Variety of Cytokine Receptors," *Cell*, 93(3): 385-395 (1998).
Pesu et al., "Therapeutic targeting of Janus kinases," *Immunol. Rev.*, 223(1): 132-142 (2008).
Rodig et al., "Disruption of the Jak1 Gene Demonstrates Obligatory and Nonredundant Roles of the Jaks in Cytokine-Induced Biologic Responses," *Cell*, 93(3): 373-383 (1998).
Shimoda et al., "Tyk2 Plays a Restricted Role in IFNα Signaling, Although It Is Required for IL-12-Mediated T Cell Function," *Immunity*, 13(4): 561-571 (2000).
Smolen et al., "Effect of interleukin-6 receptor inhibition with tocilizumab in patients with rheumatoid arthritis (OPTION study): a double-blind, placebo-controlled, randomised trial," *Lancet*, 371(9617): 987-997 (2008).
Tanaka et al., "JAK inhibitor tofacitinib for treating rheumatoid arthritis: from basic to clinical," *Mod. Rheumatol.*, 23(3): 415-424 (2013).
Vanhoutte et al., "Selective JAK1 Inhibition in the Treatment of Rheumatoid Arthritis: Proof of Concept with GLPG0634," *Arthritis Rheum.*, 64(Suppl. 10): 2489 (2012).
Zak et al., "Discovery and Optimization of C-2 Methyl Imidazopyrrolopyridines as Potent and Orally Bioavailable JAK1 Inhibitors with Selectivity over JAK2," *J. Med. Chem.*, 55(13): 6176-6193 (2012).
Benveniste et al., "Involvement of the Janus Kinase/Signal Transducer and Activator of Transcription Signaling Pathway in Multiple Sclerosis and the Animal Model of Experimental Autoimmune Encephalomyelitis," *J. Interferon Cytokine Res.*, 34(8): 577-588 (2014).
Boyle et al., "The JAK inhibitor tofacitinib suppresses synovial JAK1-STAT signalling in rheumatoid arthritis," *Ann. Rheum. Dis.*, 74: 1311-1316 (2015).
Carniti et al., "Pharmacologic Inhibition of JAK1/JAK2 Signaling Reduces Experimental Murine Acute GVHD While Preserving GVT Effects," *Clin. Cancer Res.*, 21(16): 3740-3749 (2015).
Cetkovic-Cvrlje et al., "Targeting Janus tyrosine kinase 3 (JAK3) with an inhibitor induces secretion of TGF-b by CD41 T cells," *Cell. Mol. Immunol.*, 9: 350-360 (2012).
Chiricozzi et al., "New topical treatments for psoriasis," *Exp. Opin. Pharmacother.*, 15(4): 461-470 (2014).

Deuse et al., "Significant Reduction of Acute Cardiac Allograft Rejection by Selective Janus Kinase-1/3 Inhibition Using R507 and R545 Tobias," *Transplantation*, 94(7): 695-702 (2012).
Flex et al., "Somatically acquired JAK1 mutations in adult acute lymphoblastic leukemia," *J. Exp. Med.*, 205(4): 751-758 (2008).
Fridman et al., "Preclinical Evaluation of Local JAK1 and JAK2 Inhibition in Cutaneous Inflammation," *J. Invest. Dermatol.*, 131: 1838-1844 (2011).
Gu et al., "Pharmacologic Suppression of JAK1/2 by JAK1/2 Inhibitor AZD1480 Potently Inhibits IL-6-Induced Experimental Prostate Cancer Metastases Formation," *Mol. Cancer Ther.*, 13(5): 1246-1258 (2014).
Hsu et al., "JAK Inhibitors: Treatment Efficacy and Safety Profile in Patients with Psoriasis," *J. Immunol. Res.*, 2014:283617 (2014).
Jabbari et al., "Reversal of Alopecia Areata Following Treatment With the JAK1/2 Inhibitor Baricitinib," *EBioMedicine*, 2: 351-355 (2015).
Kawasaki et al., "Possible role of the JAK/STAT pathways in the regulation of T cell-interferon related genes in systemic lupus erythematosus," *Lupus*, 20(12): 1231-1239 (2011).
Kim et al., "Auranofin blocks interleukin-6 signalling by inhibiting phosphorylation of JAK1 and STAT3," *Immunology*, 122: 607-614 (2007).
Kim et al., "Ceramide accelerates ultraviolet-induced MMP-1 expression through JAK1/STAT-1 pathway in cultured human dermal fibroblasts," *J. Lipid Res.*, 49: 2571-2581 (2008).
Liu et al., "Down-regulation of JAK1 by RNA interference inhibits growth of the lung cancer cell line A549 and interferes with the PI3K/mTOR pathway," *J. Cancer Res. Clin. Oncol.*, 137: 1629-1640 (2011).
Liu et al., "Therapeutic Efficacy of Suppressing the JAK/STAT Pathway in Multiple Models of Experimental Autoimmune Encephalomyelitis," *J. Immunol.*, 192: 59-72 (2014).
Menet et al., "Progress toward JAK1-selective inhibitors," *Future Med. Chem.*, 7(2): 203-235 (2015).
Merciris et al., "P072 GLPG0634, the first selective JAK1 inhibitor, shows strong activity in the mouse DSS-colitis model," JAAD, 8(Suppl1): S92 (2014).
Neurath, MF. "New targets for mucosal healing and therapy in inflammatory bowel diseases," *Mucosal Immunol.*, 7(1): 6-19 (2014).
O'Shea et al., Supplement "Janus kinase inhibitors in autoimmune diseases," *Ann. Rheum. Dis.*, 72(Suppl2): ii111-ii115 (2013).
Ortiz-Ibáñez et al., "Tofacitinib and Other Kinase Inhibitors in the Treatment of Psoriasis," *Actas Dermosifiliogr.*, 104(4): 304-310 (2013).
Papp et al., "Efficacy and safety of tofacitinib, an oral Janus kinase inhibitor, in the treatment of psoriasis: a Phase 2b randomized placebo-controlled dose-ranging study K.A.," *Br. J. Dermatol.*, 167: 668-677 (2012).
Park et al., "Inhibition of JAK1/STAT3 signaling mediates compound K-induced apoptosis in human multiple myeloma U266 cells," *Food. Chem. Toxicol.*, 49(6): 1367-1372 (2011).
Patterson et al., "Protein kinase inhibitors in the treatment of inflammatory and autoimmune diseases," *Clin. Exp. Immunol.*, 176: 1-10 (2014).
Scott, L., "Lymphoid malignancies: Another face to the Janus kinases," *Blood Rev.*, 27(2): 63-70 (2013).
Wang et al., "Jak/STAT signaling is involved in the inflammatory infiltration of the kidneys in MRL/lpr mice," *Lupus*, 19(10): 1171-1180 (2010).
Xiao et al., "Association of single-nucleotide polymorphisms in the STAT3 gene with autoimmune thyroid disease in Chinese individuals," *Fund. Integr. Genomics*, 13: 455-461 (2013).

SEQUENCE LISTING

<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: JAK1 substrate

<400> SEQUENCE: 1

Gly Glu Glu Pro Leu Tyr Trp Ser Phe Pro Ala Lys Lys Lys
1               5                   10

```
<210> SEQ ID NO 2
<211> LENGTH: 39
<212> TYPE: PRT
<213> ORGANISM: Artificial Sequence
<220> FEATURE:
<223> OTHER INFORMATION: JAK2 substrate

<400> SEQUENCE: 2

Lys Thr Phe Cys Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
            20                  25                  30

Asp Tyr Ile Ala Asp Trp Cys
            35

<210> SEQ ID NO 3
<211> LENGTH: 15
<212> TYPE: PRT
<213> ORGANISM: Artificial Sequence
<220> FEATURE:
<223> OTHER INFORMATION: JAK3 substrate

<400> SEQUENCE: 3

Gly Gly Glu Glu Glu Glu Tyr Phe Glu Leu Val Lys Lys Lys Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: TYK2 substrate

<400> SEQUENCE: 4

Gly Gly Met Glu Asp Ile Tyr Phe Glu Phe Met Gly Gly Lys Lys Lys
1               5                   10                  15
```

JANUS KINASE 1 SELECTIVE INHIBITOR AND PHARMACEUTICAL USE THEREOF

CROSS-REFERENCE TO RELATED APPLICATIONS

This patent application is the U.S. national stage of Patent Application No. PCT/KR2016/009205, filed Aug. 19, 2016, which claims the benefit of Korean Patent Application No. 10-2015-0118268, filed Aug. 21, 2015, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,000 Byte ASCII (Text) file named "9. PX052988_SEQUENCE LISTING.TXT," dated Apr. 10, 2015.

TECHNICAL FIELD

The present disclosure relates to a Janus kinase (JAK) inhibitor, and more particularly, to a compound having high selectivity for Janus kinase 1 (JAK1) and a pharmaceutical use thereof.

BACKGROUND ART

T-cells transmit signals received from antigen-presenting cells via T-cell receptors (TCRs) present on surfaces thereof to sub-effectors (effector T-cells) by the activation of a variety of intracellular protein kinases such as Janus kinases (JAKs). In this process, T-cells secrete various interleukins (ILs) or interferon-γ (IFN) to activate various white blood cells and also B-cells. Typical protein kinases involved in signaling in T-cells are four JAK isozymes, i.e., JAK1, JAK2, JAK3, and tyrosine kinase 2 (TYK2), which will be collectively referred to as "Janus kinase" or "JAK" hereinafter.

JAKs have been widely studied as a target for treatment of autoimmune and/or inflammatory diseases. JAK inhibitors have been reported to be useful for the treatment of general symptoms of autoimmune diseases; immune system dysfunctions; viral diseases; and cancers, for example rheumatoid arthritis, psoriasis, atopic dermatitis, lupus, multiple sclerosis, type I diabetes, diabetic complications, asthma, autoimmune thyroid disorders, ulcerative colitis, Crohn's disease, Alzheimer's disease, cancer, leukemia, and organ transplantation or xenograft rejection (*Immunol. Rev.,* 2008, 223(1), 132-142; *Proc. Natl. Acad. Sci. U.S.A,* 1995, 92(19), 8724-8728; *Science,* 1995, 270(5237), 800-802; *Trends Pharmacol. Sci.,* 2004, 25(11), 558-562).

Many pharmaceutical companies have competitively studied and developed JAK3 inhibitors with the expectation of developing therapeutic agents for autoimmune diseases such as rheumatoid arthritis (RA) with selective inhibitory activity against JAK3 among JAKs. As a result, recently Pfizer's Xeljanz® (tofacitinib) has received FDA approval as a therapeutic agent for rheumatoid arthritis. However, tofacitinib thought to have selective inhibitory activity against JAK3 at the earlier stage of development has now been identified as a pan-JAK inhibitor having general inhibitory activity against the JAK kinase family, raising an ongoing controversial issue regarding that inhibitory activity against which particular JAK isozyme is the most important factor in the efficacy of a therapeutic agent for rheumatoid arthritis.

To sum up the results of a series of recent studies (*Cell,* 1998, 93(3), 373-383; *Immunity,* 2000, 13(4), 561-571; *Cell,* 1998, 93(3), 385-395; *Lancet,* 2008, 371(9617), 987-997; *Chem. Biol.,* 2011, 18(3), 314-323), it was found that the JAK kinase that is crucial in signaling by T-cell receptors is JAK1, and JAK3 merely plays a limited auxiliary role. Accordingly, in the field of therapeutic agents for autoimmune diseases and/or inflammatory diseases, development of JAK inhibitors is focused on JAK1, not on JAK3, and substances having selective inhibitory activity against JAK1 are being reported one after another (*J. Med. Chem.,* 2012, 55(12), 5901-5921; *J. Med. Chem.,* 2012, 55(13), 6176-6193).

Tofacitinib, which has been identified as a pan-JAK inhibitor, was reported to have side effects, including headache, nausea, diarrhea, infection due to decreased immunity, hyperlipidemia, nasopharyngitis, increased alanine transaminase (ALT) and aspartate transaminase (AST), severe anemia, and neutropenia (*Mod. Rheumatol.,* 2013, 23(3), 415-424). On the contrary, filgotinib as a JAK1 selective inhibitor was reported not to have such side effects of tofacitinib (*Arthritis Rheum.,* 2012, 64 (Suppl. 10), 2489). As a result of clinical studies on various drugs known as JAK inhibitors, filgotinib and INCB-039110, as selective JAK1 inhibitors, were reported to have a significantly higher therapeutic limit than other JAK isozyme inhibitors or non-selective inhibitors (*Expert Opin. Investig. Drugs,* 2014, 23(8), 1067-1077).

A selective inhibitor of JAK1 is effective in the treatment of rheumatoid arthritis. Inactivation of JAK2 may induce anemia in animal models since JAK2 is essential in the erythropoietin (EPO) signaling pathway essential for red blood cell production. Accordingly, compounds having a higher enzymatic inhibition rate of JAK1 with respect to JAK2 may exhibit a relatively broad therapeutic index in JAK2-dependent anemia. Therefore, a selective inhibitor of JAK1 over JAK2 is likely to be effective as a therapeutic agent having reduced side effects for rheumatoid arthritis and other immune diseases (*J. Med. Chem.,* 2012, 55(13), 6176-6193).

Patent document 1 discloses a wide range of compounds as JAK inhibitors represented by the following formula.

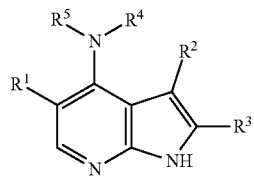

Patent document 1 discloses an assay method of inhibitory activity against JAK1, JAK2, and JAK3, but does not provide any data of a compound represented by the above formula or any comment on the selective inhibitory activity against JAK1.

Patent document 2 discloses that a compound represented by the following formula has inhibitory activity against JAK3, and an assay method of inhibitory activity against JAK3, but does not provide any data of the compound or any comment on the selective inhibitory activity against JAK1.

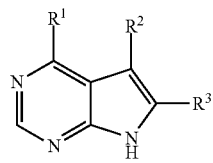

Patent document 2 also discloses 3-{4-methyl-3-[methyl-(7H-pyrrolo[2,3-d]pyrimidine-4-yl)-amino]-piperidine-1-yl}-3-oxo-propionitrile, which corresponds to tofacitinib, the above-described FDA-approved drug.

PRIOR ART DOCUMENTS

Patent Document (Patent document 1) WO 2006/069080
(Patent document 2) U.S. Pat. No. 6,956,041

DETAILED DESCRIPTION OF THE INVENTION

Technical Problem

The present disclosure provides a compound of Formula 1 or Formula 2, or a pharmaceutically acceptable salt, solvate, or stereoisomer thereof.

The present disclosure provides a pharmaceutical composition including a compound of Formula 1 or Formula 2, or a pharmaceutically acceptable salt, solvate, or stereoisomer of the compound, and a pharmaceutically acceptable carrier.

The present disclosure provides a method of inhibiting the activity of a Janus kinase (JAK) by using a compound of Formula 1 or Formula 2, or a pharmaceutically acceptable salt, solvate, or stereoisomer of the compound.

The present disclosure provides a method of treating a disease associated with JAK in a subject by administering a compound of Formula 1 or Formula 2, or a pharmaceutically acceptable salt, solvate, or stereoisomer of the compound to the subject.

The present disclosure provides a method of preparing a compound of Formula 1 or Formula 2.

Technical Solution

Unless otherwise defined, all terms (including technical and scientific terms) used herein have the same meaning as commonly understood by one of ordinary skill in the art to which this invention belongs. Although exemplary methods or materials are listed herein, other similar or equivalent ones are also within the scope of the present invention. All publications disclosed as references herein are incorporated in their entirety by reference.

In an aspect of the present disclosure, a compound of Formula 1, or a pharmaceutically acceptable salt, solvate, or stereoisomer thereof is provided.

[Formula 1]

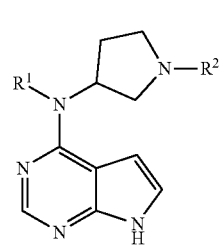

In Formula 1,
$R^1$ may be hydrogen, $C_{1-2}$ alkyl, or cyclopropylmethyl;
$R^2$ may be 2-cyanoacetyl, 2-cyanoethyl, butyl, 2-azidoacetyl, 3-methylbutanoyl, isobutoxycarbonyl, anilinocarbonyl, methylsulfonyl, (trifluoromethyl)sulfonyl, ethylsulfonyl, propylsulfonyl, isopropylsulfonyl, (1-methyl-1H-imidazole-4-yl)sulfonyl, phenylsulfonyl, (2-fluorophenyl)sulfonyl, (3-fluorophenyl)sulfonyl, (4-fluorophenyl)sulfonyl, (2-cyanophenyl)sulfonyl, (3-cyanophenyl)sulfonyl, (4-cyanophenyl)sulfonyl, (2-nitrophenyl)sulfonyl, (3-nitrophenyl)sulfonyl, (4-nitrophenyl)sulfonyl, m-tolylsulfonyl, tosyl, (4-methoxyphenyl)sulfonyl, ((4-trifluoromethyl)phenyl)sulfonyl, naphthalene-2-ylsulfonyl, piperidine-1-ylsulfonyl, or morpholinosulfonyl.

Examples of the compound of Formula 1, or pharmaceutically acceptable salts, solvates, or stereoisomers thereof may include compounds selected from the group consisting of the following listed compounds:

(R)-3-(3-(methyl(7H-pyrrolo[2,3-d]pyrimidine-4-yl)amino) pyrrolidine-1-yl)-3-oxopropanenitrile;
(R)-3-(3-(methyl(7H-pyrrolo[2,3-d]pyrimidine-4-yl)amino) pyrrolidine-1-yl)propanenitrile;
(R)—N-(1-butylpyrrolidine-3-yl)-N-methyl-7H-pyrrolo[2,3-d]pyrimidine-4-amine;
(R)-2-azido-1-(3-(methyl(7H-pyrrolo[2,3-d]pyrimidine-4-yl)amino)pyrrolidine-1-yl)ethane-1-one;
(R)-3-methyl-1-(3-(methyl(7H-pyrrolo[2,3-d]pyrimidine-4-yl)amino)pyrrolidine-1-yl)butane-1-one;
isobutyl (R)-3-(methyl(7H-pyrrolo[2,3-d]pyrimidine-4-yl)amino)pyrrolidine-1-carboxylate;
(R)-3-(methyl(7H-pyrrolo[2,3-d]pyrimidine-4-yl)amino)-N-phenylpyrrolidine-1-carboxamide;
(R)—N-methyl-N-(1-(methylsulfonyl)pyrrolidine-3-yl)-7H-pyrrolo[2,3-d]pyrimidine-4-amine;
(R)—N-methyl-N-(1-((trifluoromethyl)sulfonyl)pyrrolidine-3-yl)-7H-pyrrolo[2,3-d]pyrimidine-4-amine;
(R)—N-(1-(ethylsulfonyl)pyrrolidine-3-yl)-N-methyl-7H-pyrrolo[2,3-d]pyrimidine-4-amine;
(R)—N-methyl-N-(1-(propylsulfonyl)pyrrolidine-3-yl)-7H-pyrrolo[2,3-d]pyrimidine-4-amine;
(R)—N-(1-(isopropylsulfonyl)pyrrolidine-3-yl)-N-methyl-7H-pyrrolo[2,3-d]pyrimidine-4-amine;
(R)—N-methyl-N-(1-((1-methyl-1H-imidazole-4-yl)sulfonyl)pyrrolidine-3-yl)-7H-pyrrolo[2,3-d]pyrimidine-4-amine;
(R)—N-methyl-N-(1-(phenylsulfonyl)pyrrolidine-3-yl)-7H-pyrrolo[2,3-d]pyrimidine-4-amine;
(R)—N-(1-((2-fluorophenyl)sulfonyl)pyrrolidine-3-yl)-N-methyl-7H-pyrrolo[2,3-d]pyrimidine-4-amine;
(R)—N-(1-((3-fluorophenyl)sulfonyl)pyrrolidine-3-yl)-N-methyl-7H-pyrrolo[2,3-d]pyrimidine-4-amine;
(R)—N-(1-((4-fluorophenyl)sulfonyl)pyrrolidine-3-yl)-N-methyl-7H-pyrrolo[2,3-d]pyrimidine-4-amine;
(R)-2-((3-(methyl(7H-pyrrolo[2,3-d]pyrimidine-4-yl) amino)pyrrolidine-1-yl)sulfonyl)benzonitrile;

(R)-3-((3-(methyl(7H-pyrrolo[2,3-d]pyrimidine-4-yl)amino)pyrrolidine-1-yl)sulfonyl)benzonitrile;
(R)-4-((3-(methyl(7H-pyrrolo[2,3-d]pyrimidine-4-yl)amino)pyrrolidine-1-yl)sulfonyl)benzonitrile;
(R)—N-methyl-N-(1-((2-nitrophenyl)sulfonyl)pyrrolidine-3-yl)-7H-pyrrolo[2,3-d]pyrimidine-4-amine;
(R)—N-methyl-N-(1-((3-nitrophenyl)sulfonyl)pyrrolidine-3-yl)-7H-pyrrolo[2,3-d]pyrimidine-4-amine;
(R)—N-methyl-N-(1-((4-nitrophenyl)sulfonyl)pyrrolidine-3-yl)-7H-pyrrolo[2,3-d]pyrimidine-4-amine;
(R)—N-methyl-N-(1-(m-tolylsulfonyl)pyrrolidine-3-yl)-7H-pyrrolo[2,3-d]pyrimidine-4-amine;
(R)—N-methyl-N-(1-tosylpyrrolidine-3-yl)-7H-pyrrolo[2,3-d]pyrimidine-4-amine;
(R)—N-(1-((4-methoxyphenyl)sulfonyl)pyrrolidine-3-yl)-N-methyl-7H-pyrrolo[2,3-d]pyrimidine-4-amine;
(R)—N-methyl-N-(1-((4-(trifluoromethyl)phenyl)sulfonyl)pyrrolidine-3-yl)-7H-pyrrolo[2,3-d]pyrimidine-4-amine;
(R)—N-methyl-N-(1-(naphthalene-2-ylsulfonyl)pyrrolidine-3-yl)-7H-pyrrolo[2,3-d]pyrimidine-4-amine;
(R)—N-methyl-N-(1-(piperidine-1-ylsulfonyl)pyrrolidine-3-yl)-7H-pyrrolo[2,3-d]pyrimidine-4-amine;
(R)—N-methyl-N-(1-(morpholinosulfonyl)pyrrolidine-3-yl)-7H-pyrrolo[2,3-d]pyrimidine-4-amine;
(S)-3-(3-(methyl(7H-pyrrolo[2,3-d]pyrimidine-4-yl)amino)pyrrolidine-1-yl)-3-oxopropanenitrile;
(R)-3-((3-((7H-pyrrolo[2,3-d]pyrimidine-4-yl)amino)pyrrolidine-1-yl)sulfonyl)benzonitrile;
(R)-3-(3-(ethyl(7H-pyrrolo[2,3-d]pyrimidine-4-yl)amino)pyrrolidine-1-yl)-3-oxopropanenitrile;
(R)-3-((3-(ethyl(7H-pyrrolo[2,3-d]pyrimidine-4-yl)amino)pyrrolidine-1-yl)sulfonyl)benzonitrile;
(R)-3-(3-((cyclopropylmethyl)(7H-pyrrolo[2,3-d]pyrimidine-4-yl)amino)pyrrolidine-1-yl)-3-oxopropanenitrile; and
(R)-3-((3-((cyclopropylmethyl)(7H-pyrrolo[2,3-d]pyrimidine-4-yl)amino)pyrrolidine-1-yl)sulfonyl)benzonitrile.

In another aspect of the present disclosure, a compound of Formula 2, or a pharmaceutically acceptable salt, solvate, or stereoisomer thereof is provided.

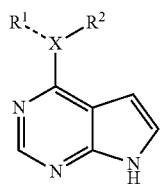

[Formula 2]

In Formula 2,
X may be nitrogen or oxygen,
--- may be a single bond when X is nitrogen, or may be absent when X is oxygen, and
$R^1$ may be methyl,
$R^2$ may be 1-(2-cyanoacetyl)piperidine-4-yl, 1-(phenylsulfonyl)piperidine-4-yl, 1-(3-cyanophenylsulfonyl)piperidine-4-yl, 1-(2-cyanoacetyl)piperidine-3-yl, 1-(3-cyanophenylsulfonyl)piperidine-3-yl, 1-(3-cyanophenylsulfonyl)-4-methyl-piperidine-3-yl, 1-(2-cyanoacetyl)-3,3-dimethylpyrrolidine-4-yl, [1-(2-cyanoacetyl)piperidine-3-yl]methyl, or [1-(3-cyanophenylsulfonyl)piperidine-3-yl]methyl,
or $R^1$ and $R^2$, together with X, may form 6-(2-cyanoacetyl)octahydro-6H-pyrrolo-[3,4-b]pyridine-1-yl.

Examples of the compound of Formula 2, or pharmaceutically acceptable salts, solvates, or stereoisomers thereof may include compounds selected from the group consisting of the following listed compounds:
3-(4-(methyl(7H-pyrrolo[2,3-d]pyrimidine-4-yl)amino)piperidine-1-yl)-3-oxopropanenitrile;
N-methyl-N-(1-(phenylsulfonyl)piperidine-4-yl)-7H-pyrrolo[2,3-d]pyrimidine-4-amine;
3-((4-(methyl(7H-pyrrolo[2,3-d]pyrimidine-4-yl)amino)piperidine-1-yl)sulfonyl)benzonitrile;
(R)-3-(3-(methyl(7H-pyrrolo[2,3-d]pyrimidine-4-yl)amino)piperidine-1-yl)-3-oxopropanenitrile;
(R)-3-((3-(methyl(7H-pyrrolo[2,3-d]pyrimidine-4-yl)amino)piperidine-1-yl)sulfonyl)benzonitrile;
3-(((3R,4R)-4-methyl-3-(methyl(7H-pyrrolo[2,3-d]pyrimidine-4-yl)amino)piperidine-1-yl)sulfonyl)benzonitrile;
(R)-3-(3,3-dimethyl-4-(methyl(7H-pyrrolo[2,3-d]pyrimidine-4-yl)amino)pyrrolidine-1-yl)-3-oxopropanenitrile;
(S)-3-(3,3-dimethyl-4-(methyl(7H-pyrrolo[2,3-d]pyrimidine-4-yl)amino)pyrrolidine-1-yl)-3-oxopropanenitrile;
3-(4-((7H-pyrrolo[2,3-d]pyrimidine-4-yl)oxy)piperidine-1-yl)-3-oxopropanenitrile;
3-((4-((7H-pyrrolo[2,3-d]pyrimidine-4-yl)oxy)piperidine-1-yl)sulfonyl)benzonitrile;
3-(3-(((7H-pyrrolo[2,3-d]pyrimidine-4-yl)oxy)methyl)piperidine-1-yl)-3-oxopropanenitrile;
3-((3-(((7H-pyrrolo[2,3-d]pyrimidine-4-yl)oxy)methyl)piperidine-1-yl)sulfonyl)benzonitrile;
3-((4aR,7aR)-1-(7H-pyrrolo[2,3-d]pyrimidine-4-yl)octahydro-6H-pyrrolo[3,4-b]pyridine-6-yl)-3-oxopropanenitrile; and
3-((4aS,7aS)-1-(7H-pyrrolo[2,3-d]pyrimidine-4-yl)octahydro-6H-pyrrolo[3,4-b]pyridine-6-yl)-3-oxopropanenitrile.

Hereinafter, the compound of Formula 1, the compound of Formula 2, or a pharmaceutically acceptable salt, solvate, or stereoisomer thereof will be collectively referred to as a compound according to one or more embodiments.

The compound according to one or more embodiments may be substituted with a detectable label. The detectable label may be an optical label, an electrical label, a magnetic label, or an indirect label. The optical label, as a material generating a detectable optical signal, may be a radioactive material or a chromogenic material such as a fluorescent material. The indirect label may refer to a material that may generate a detectable label by binding to a specific material such as an enzyme which converts a substrate into a chromogenic material, a substrate thereof, or a particular material such as an antibody or an antigen. The optical label may be an isotope of any element that constitutes the compound according to one or more embodiments. Accordingly, the compound according to one or more embodiments may be substituted with an isotope, for example, a radioactive isotope, of at least one of the elements which constitute the compound. Examples of the isotope may include $^2H$ (represented also as D for deuterium), $^3H$ (represented also as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The compounds of Formulae 1 and 2 substituted with a detectable label, according to embodiments, may be used to identify the location of JAK in a cell or subject, and thus to identify treat a site of diseases related to increased activity of JAK.

The compound according to one or more embodiments may be in the form of a pharmaceutically acceptable salt thereof. The salt may be a common acid addition salt used in the art of JAK inhibitors, for example, a salt derived from an inorganic salt such as hydrochloric acid, bromic acid, sulfuric acid, sulfamic acid, phosphoric acid, or nitric acid; or a salt derived from an organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. The salt may be in the form of a common metal salt, for example, a salt derived from a metal such as lithium, sodium, potassium, magnesium, or calcium. The acid addition salt or the metal salt may be prepared by a common method known in the field of organic chemistry.

The compound according to one or more embodiments may be in the form of a solvate thereof.

The term "solvate" refers to a complex or aggregate of at least one solute molecule, that is, the compound of Formula 1 or Formula 2 or a pharmaceutically acceptable salt thereof, and at least one solvent molecule. The solvate may be a complex or aggregate of the compound of Formula 1 or a pharmaceutically acceptable salt thereof, with, for example, water, methanol, ethanol, isopropanol, or acetic acid.

The compound according to one or more embodiments may be in the form of a stereoisomer thereof. The stereoisomer may be any stereoisomer, including an enantiomer or a diastereomer. The compound according to one or more embodiments may be in a stereoisomerically pure form or a mixture of at least one stereoisomer, for example, a racemic mixture. Isolation of specific stereoisomers may be carried out by one of common methods known in the art.

In another aspect of the present disclosure, there is provided a pharmaceutical composition including a therapeutically effective amount of the compound of Formula 1 or Formula 2, or a pharmaceutically acceptable salt, solvate, or stereoisomer thereof.

The compound of Formula 1 or Formula 2 according to one or more embodiments may have an effect of inhibiting the activity of one, two, or more JAK isozymes. Any form of the term "inhibition" used herein may refer to reducing the activity of one, two, or more JAK isozymes.

The "JAK" used herein may include any enzyme in the Janus kinase family. In some embodiments, the compound may inhibit the activity of JAK1, JAK2, JAK3, and TYK2. In some embodiments, the compound may selectively inhibit the activity of JAK1, JAK3, and TYK2. In some other embodiments, the compound may inhibit the activity of JAK1 only. This JAK inhibitory effect of the compound according to one or more embodiments was confirmed in Test Example 1. The compound according to one or more embodiments exhibited an anti-inflammatory effect in a croton oil-induced inflammation animal model.

The JAK inhibitory effect is measured as the degree to which the convention of ADP to ATP is inhibited in the presence of the compound according to one or more embodiment. When a measured absorbance is under a standard absorption curve, the inhibitory effect may be expressed as a negative value lower than a negative control value, which substantially indicates a 0% inhibition effect having no inhibitory efficacy.

Since the compound of Formula 1 or Formula 2 included in the pharmaceutical composition according to one or more embodiments has JAK inhibitory activity (see Test Example 1), the pharmaceutical composition may be used for the treatment of any disease (hereinafter, referred to as "JAK-related disease") known to be treated using JAK inhibitory activity (*Immunol. Rev.*, 2008, 223(1), 132-142; *Proc. Natl. Acad. Sci. U.S.A.*, 1995, 92(19), 8724-8728; *Science*, 1995, 270(5237), 800-802; *Trends Pharmacol. Sci.*, 2004, 25(11), 558-562). The JAK-related disease may include an autoimmune disease, an immune system dysfunction, a viral disease, an allergic disease, a skin disease, an IL-6 pathway-related disease, an immune response, a hyperproliferative disorder, or a cancer. The autoimmune disease may include, for example, a skin disease, multiple sclerosis, rheumatoid arthritis, juvenile arthritis, type I diabetes, lupus, psoriasis, an inflammatory bowel disease, ulcerative colitis, Crohn's disease, or an autoimmune thyroid disease. The immune system dysfunction may include, for example, an allograft rejection, a graft-versus-host disease, an allograft rejection reaction, or a graft-versus-host reaction. The viral disease may include, for example, Epstein-Barr virus (EBV), hepatitis B, hepatitis C, HIV, HTLV 1, chickenpox, herpes zoster virus (VZV), or human papillomavirus (HPV) disease. The cancer may include, for example, prostate cancer, kidney cancer, liver cancer, pancreatic cancer, gastric cancer, breast cancer, lung cancer, head and neck cancer, glioblastoma, leukemia, lymphoma, or multiple myeloma. However, embodiments are not limited thereto.

The immune response may be, for example, diarrhea, skin irritation, skin rash, contact dermatitis, or allergic contact hypersensitivity. The allergic disease may be asthma, food allergy, atopic dermatitis, or rhinitis. Examples of the IL-6 pathway-related disease may include Castleman's disease and Kaposi's sarcoma. However, embodiments are not limited thereto.

The compound according to one or more embodiments may selectively inhibit JAK1 relative to JAK2 (see Test Example 1). The expression "selectively" used herein may indicate that a certain compound according to an embodiment has a greater inhibitory effect on a specific JAK than on at least one other JAK. The compound according to one or more embodiments may selectively inhibit JAK1, relative to JAK2, by at least 1 fold or greater, 1.1 fold, 1.2 fold, 5 fold, 10 fold, 20 fold, 40 fold, 100 fold, 200 fold, 500 fold, 1,000 fold or greater, or to infinity ($\infty$). The selective inhibition of JAK1 relative to JAK2 "to infinity" may refer to the inhibition of JAK1 only, while substantially not inhibiting JAK2.

The compound according to one or more embodiments may selectively inhibit JAK1 relative to JAK2, and thus may be used for the treatment of the above-listed JAK-related diseases while relieving or preventing any side effects from inhibition of JAK2. For examples, the side effects which likely occur by the inhibition of JAK2 may include headache, nausea, diarrhea, infection due to decreased immunity, hyperlipidemia, nasopharyngitis, increased alanine transaminase (ALT) and aspartate transaminase (AST), severe anemia, and neutropenia. However, embodiments are not limited thereto.

The compound according to one or more embodiments may have a remarkably longer half-life, compared to tofacitinib, which is a conventional, FDA-approved JAK inhibitor, and provide an increased drug dosing interval (see Test Example 3). Accordingly, a pharmaceutical composition including the compound according to one or more embodiments may allow a reduced number of drug doses, and thus improve patient's medication compliance.

The pharmaceutical composition according to one or more embodiments may include a therapeutically effective amount of the compound of Formula 1 or Formula 2, or a pharmaceutically acceptable salt, solvate, or stereoisomer thereof, as described above.

In the pharmaceutical composition according to one or more embodiments, the term "therapeutically effective amount" may refer to an amount sufficient to exhibit a therapeutic effect when administered to a subject in need of treatment.

The term "treatment" may refer to treatment of a disease or a medical symptom, for example, a JAK-related disease, in a mammal, including humans, and may include the following: (a) preventing the occurrence of a disease or medical symptom, i.e., prophylactic treatment of a patient; (b) alleviating a disease or medical symptom, i.e., removal or recovery of a disease or medical condition in a patient; (c) suppressing a disease or medical symptom, i.e., slowing or stopping the progression of a disease or medical symptom in a subject; or (d) alleviating a disease or medical symptom in a subject.

The "effective amount" may be properly chosen by one of ordinary skill in the art. For example, the "effective amount" may be about 0.01 mg to about 10,000 mg, about 0.1 mg to about 1,000 mg, about 1 mg to about 100 mg, about 0.01 mg to about 1,000 mg, about 0.01 mg to about 100 mg, about 0.01 mg to about 10 mg, or about 0.01 mg to about 1 mg.

In the pharmaceutical composition according to one or more embodiments, the compound of Formula 1 or Formula 2 and the pharmaceutically acceptable salt, solvate, or stereoisomer thereof may be the same as described above.

The pharmaceutical composition according to one or more embodiments may be administered to various mammals such as rats, mice, livestock, and humans via various routes, for example, an oral route, a rectal route, or an intravenous, intramuscular, subcutaneous, intrathecal, or intracerebroventricular injection. Accordingly, the pharmaceutical composition may be formulated as pharmaceutical formulations commonly used in the art. The pharmaceutical composition may be formulated as, but not limited to, formulations for oral administration, injections, suppositories, formulations for transdermal administration, and formulations for nasal administration. For example, the pharmaceutical composition may be formulated as formulations for oral administrations such as liquids, suspensions, powders, granules, tablets, capsules, pills, emulsions, syrups, aerosols, or extracts.

In the preparation of each formulation, a pharmaceutically acceptable additive required therefor may be added. For example, when the pharmaceutical composition according to one or more embodiments is formulated as a formulation for oral administration, at least one selected from the group consisting of a diluent, a lubricant, a binder, a disintegrant, a sweetener, a stabilizer, and a preservative may be used as the additive. Optionally, at least one selected from the group consisting of a flavor, a vitamin, and an anti-oxidant may be used.

The additive may be any pharmaceutically acceptable additive. For example, the diluent may be lactose, dextrose, sucrose, corn starch, soybean oil, amorphous cellulose, sorbitol, xylitol, or mannitol. The lubricant may be magnesium stearate or talc. The binder may be polyvinyl pyrrolidine or hydroxypropyl cellulose. The disintegrant may be calcium carboxymethylcellulose, sodium starch glycolate, polacrilin potassium, or crospovidone. The sweetener may be sucrose, fructose, sorbitol, or aspartame. The stabilizer may be sodium carboxymethyl cellulose, β-cyclodextrin, white beeswax, or xanthan gum. The preservative may be methyl p-hydroxybenzoate, propyl p-hydroxybenzoate, or potassium sorbate.

In addition to the aforementioned ingredients, a natural flavors such as a plum flavor, a lemon flavor, a pineapple flavor, and a herb flavor, a natural food colorant such as natural fruit juice, chlorophyllin, and flavonoids, a sweetener such as fructose, honey, sugar alcohol, and sugar, or an acidifier such as citric acid and sodium citrate may be used in combinations to make the formulation taste better.

Among the above-listed formulations, examples of formulations for parenteral administration may include sterilized aqueous solutions, non-aqueous solutions, suspensions, emulsions, lyophilized formulations, and suppositories. To prepare the non-aqueous solutions and suspensions, propylene glycol, polyethylene glycol, vegetable oils such as olive oil, and injectable esters such as ethyloleate may be used. Bases for the suppositories may include Witepsol, Macrogol, Tween 61, cacao butter, laurin fat, glycerogelatin, or the like.

The pharmaceutical composition according to one or more embodiments may be used in combination with at least one other therapeutic agent used for the treatment of JAK-related diseases. The at least one other therapeutic agent may vary according to a type of the JAK-related disease. Examples of the therapeutic agent may include a chemotherapeutic agent, an anti-inflammatory agent, an immunosuppressive agent, an anti-cancer agent, or any combinations of the forgoing agents. However, embodiments are not limited thereto. For example, combined use of the pharmaceutical composition according to one or more embodiments with a therapeutic agent for the treatment of multiple myeloma may improve therapeutic response without additional toxicity problems, as compared to when a JAK inhibitor is prescribed alone. Examples of the therapeutic agent that may be used in combination for the treatment of multiple myeloma may include melphalan, a melphalan and prednisone combination, doxorubicin, dexamethasone, and Velcade. Such combination therapy may provide a synergistic effect. Furthermore, the compound according to one or more embodiments may solve a drug resistance problem of dexamethasone in the treatment of multiple myeloma. The therapeutic agent used in the combination therapy may be administered at once or continuously in combination with a JAK inhibitor. In some embodiments, the therapeutic agent and a JAK inhibitor may be administered simultaneously or sequentially, for example, separately from each other.

In another aspect of the present disclosure, a use of the compound of Formula 1 or Formula 2, or a pharmaceutically acceptable salt, solvate, or stereoisomer thereof, in the treatment of a JAK-related disease, is provided.

In another aspect of the present disclosure, there is provided a use of the compound of Formula 1 or Formula 2, or a pharmaceutically acceptable salt, solvate, or stereoisomer thereof, in the treatment of a JAK-related disease.

In another aspect of the present disclosure, a method of inhibiting the activity of a JAK is provided, the method including inhibiting the activity of the JAK by contacting, with the JAK, the compound of Formula 1 or Formula 2, or a pharmaceutically acceptable salt, solvate, or stereoisomer thereof as defined above.

In some embodiments of the method, the contacting may be performed in vitro or in vivo. In some embodiments of the method, the JAK may be present in the cell. The JAK may be JAK1, JAK2, JAK3, or TYK2.

The inhibiting of the activity of a JAK may be reducing the activity of the JAK. The inhibiting of the activity of a JAK may be reducing the activity of a particular type of JAK by a higher degree, as compared to the activity of other types of JAK. For example, the inhibiting may include selectively inhibiting JAK1 when in the presence of JAK1 and at least one of JAK2, JAK3, and TYK2.

In the method of inhibiting the activity of a JAK, according to one or more embodiments, the activity of JAK1 is selectively inhibited relative to the activity of JAK2. The expression "selectively" used herein may indicate that a certain compound according to an embodiment has a greater inhibitory effect on a specific JAK than on at least one other JAK. The compound according to one or more embodiments may selectively inhibit JAK1, relative to JAK2, by at least 1 fold or greater, 1.1 fold, 1.2 fold, 5 fold, 10 fold, 20 fold, 40 fold, 100 fold, 200 fold, 500 fold, 1,000 fold or greater, or to infinity (∞).

In another aspect of the present disclosure, a method of treating a disease in a subject is provided, the method including administering a therapeutically effective amount of the compound of Formula 1 or Formula 2, or a pharmaceutically acceptable salt, solvate, or stereoisomer thereof, as defined above, to a subject.

In some embodiments of the method, a suitable administration route may be selected by one of ordinary skill in the art depending on the condition of a subject. The administering may be by oral, non-oral, or local administration.

In some embodiments of the method, a therapeutically effective amount may be appropriately varied by the physician, depending on various factors, including race, ethnicity, gender, age, weight, drug susceptibility, type and degree of symptoms that the subject has, a drug used in combination, and the like. A therapeutically effective amount may be estimated based on a dose-response curve obtained through an in vitro or animal model test. A ratio and concentration of the compound according to one or more embodiments in a pharmaceutical composition to be administered may be determined according to chemical properties of the compound, the administration route, and a therapeutic dosage amount. The therapeutically effective amount administered to a subject may be about 1 µg/kg to about 1 g/kg per day, or about 0.1 mg/kg to about 500 mg/kg per day.

In some embodiments of the method, the disease may be a JAK-related disease. The JAK-related disease may include an autoimmune disease, an immune system dysfunction, a viral disease, an allergic disease, a skin disease, a IL-6 pathway-related disease, an immune response, a hyperproliferative disorder, or a cancer as described above. In some embodiments, a therapeutically effective amount of the compound of Formula 1 or Formula 2 according to one or more embodiments, or a pharmaceutically acceptable salt, solvate, or stereoisomer thereof, may be administered in combination with at least one other therapeutic agent for the treatment of JAK-related diseases. Other therapeutic agent may be the same as described above.

The compound of Formula 1, or a pharmaceutically acceptable salt, solvate, or stereoisomer thereof according to embodiments, may be prepared by a method illustrated in Reaction Scheme 1.

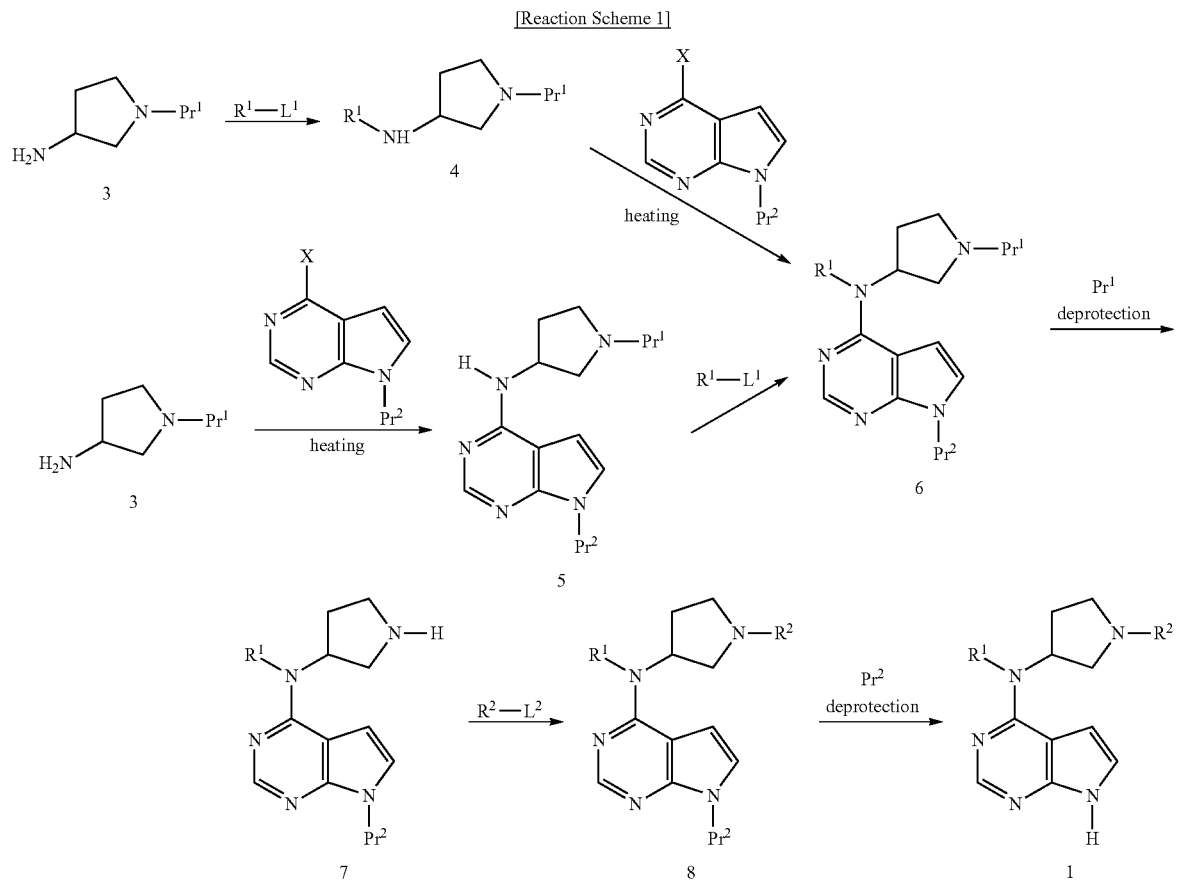

[Reaction Scheme 1]

In Reaction Scheme 1, $L^1$ and $L^2$ in Formulae 3, 4, 5, 6, 7, and 8 may be a leaving group, $Pr^1$ and $Pr^2$ may be an amino-protecting group, X may be F, Cl, Br, or I, and $R^1$ and $R^2$ may be the same as described above in connection with Formula 1.

The method of preparing the compound of Formula 1 according to an embodiment may include:

(a) reacting a compound of Formula 3 or a salt thereof with a compound of the formula $R^1$—$X^1$ to form a compound of Formula 4; and reacting the compound of Formula 4 with 6-halo-7-deazapurine to form a compound of Formula 6 by; or (b) reacting a compound of Formula 3 or a salt thereof with 6-halo-7-deazapurine to form a compound of Formula 5; and reacting the compound of Formula 5 with a compound of the formula $R^1$—$X^1$ to form a compound of Formula 6;

(c) deprotecting a nitrogen of a pyrrolidine ring in the compound of Formula 6 to form a compound of Formula 7;

(d) reacting the compound of Formula 7 with a compound of the formula $R^4$—$X^2$ to form a compound of Formula 8; and (e) deprotecting the compound of Formula 8 to prepare the compound of Formula 1.

In the method, the step (a) including the "reacting a compound of Formula 3 or a salt thereof with a compound of the formula $R^1$—$X^1$ to form a compound of Formula 4" and the "reacting the compound of Formula 5 with a compound of the formula $R^1$—$X^1$ to form a compound of Formula 6" may include, for example, alkylation (for example, methylation), alkenylation, or alkynylation.

In the method, the "reacting the compound of Formula 4 with 6-halo-7-deazapurine to form generating a compound of Formula 6" in step (a) and the "reacting a compound of Formula 3 or a salt thereof with 6-halo-7-deazapurine Formula 3 to form a compound of Formula 5" in step (b) may be performed in a suitable solvent while being heated or under reflux conditions. The 6-halo-7-deazapurine may be commercially purchased for use. The halo may be, for example, chloro.

In the method, the step (c) of "deprotecting a nitrogen of a pyrrolidine ring in the compound of Formula 6 to form a compound of Formula 7"; and the step (e) of "deprotecting the compound of Formula 8 to prepare the compound of Formula 1" may be performed by any known deprotection method.

In the method, the step (d) of "reacting the compound of Formula 7 with a compound of the formula $R^4$—$X^2$ to form a compound of Formula 8" may be performed by substitution of $X^2$ with N.

With regard to the above-described method, the term "leaving group" as used herein may refer to a functional group or atom that may be replaceable by another functional group or atom in a substitution reaction, for example, a nucleophilic substitution reaction. For examples, typical examples of the leaving groups may include a chloro group, a bromo group, and an iodine group; a sulfonic ester group, for example, tosylate, brosylate, nosylate, and the like; and an alkyloxy group, for example, acetoxy, trifluoroacetoxy, and the like.

The term "protected" may indicate that at least one functional group of a compound is protected from undesirable reactions by using a protecting group or blocking group. Functional groups that may be protected may include a carbamate (for example, tert-butoxycarbonyl), which is a typical protecting group for an amino group.

The term "amino-protecting group" as used herein may refer to a suitable protecting group for preventing undesirable reactions at an amino group. Typical examples of the amino-protecting group may include tert-butoxycarbonyl (BOC), trityl (Tr), benzyloxycarbonyl (Cbz), 9-fluorenylmethoxycarbonyl (Fmoc), formyl, trimethylsilyl (TMS), and tert-butyldimethylsilyl (TBS).

The compound of Formula 2, or a pharmaceutically acceptable salt, solvate, or stereoisomer thereof according to one or more embodiments may be prepared by one of ordinary skill in the field of organic chemistry by appropriately varying the above-described method illustrated in Reaction Scheme 1, for example, by replacing the compound of Formula 3 having a pyrrolidine structure with a compound having a piperidine structure.

In the above-described methods, the compounds according to one or more embodiments may be prepared using a general method or process, or may be prepared from a starting material which is easily obtainable, based on other information easily available to one of ordinary skill in the art.

For details of the methods of preparing the compounds according to one or more embodiments, examples that will be described below may be referred to.

The compounds according to one or more embodiments, including salts thereof and solvates thereof, including hydrates thereof, may be prepared using a general organic synthesis method widely known in the art, through one of the available multiple synthesis pathways.

Synthesis reactions of compounds according to embodiments may be performed in a suitable solvent that may be easily chosen by one of ordinary skill in the art of organic synthesis. The suitable solvent may be substantially non-reactive to a starting material or reactant, an intermediate, or a reaction product in a reaction temperature range, i.e., from the freezing point to the boiling point of the solvent. The given reaction may be performed in a solvent or in a mixture of at least two solvents. A suitable solvent may be selected for each specific reaction stage.

Synthesis of a compound according to one or more embodiments may include protecting and deprotecting various chemical functional groups. Whether or not there is a need to perform a protecting and deprotecting process, and selection of a suitable protecting group, may be easily determined by one of ordinary skill in the art.

The synthesis reaction may be observed using any suitable method known in the art. For example, formation of reaction products may be observed by spectroscopy, for example, nuclear magnetic resonance spectroscopy (for example, $^1H$ or $^{13}C$), infrared spectroscopy, spectrophotometry (for example, UV-visible), or mass spectrometry; or chromatography, for example, high-performance liquid chromatography (HPLC) or thin layer chromatography (TLC). The compounds according to one or more embodiments may be synthesized through a variety of known synthesis pathways disclosed in documents.

Advantageous Effects of the Invention

As described above, the compound of Formula 1 or Formula 2 according to the one or more embodiments, or a pharmaceutically acceptable salt, solvate, or stereoisomer thereof, may be used in treating JAK-related diseases such as autoimmune diseases, immune system dysfunctions, viral diseases, or cancers. Furthermore, the compound according to the one or more embodiments may have increased selective inhibitory activity against JAK1, relative to JAK2, compared to the conventional FDA-approved drug tofacitinib, and prevent side effects which likely occur from the inhibition of JAK2. The compound according to the one or more embodiments may have a remarkably longer half-life, compared to the conventional, FDA-approved JAK inhibitor tofacitinib, and thus may allow an increased drug dosing interval, and improve a patients' medication compliance.

MODE OF THE INVENTION

Figure 1:
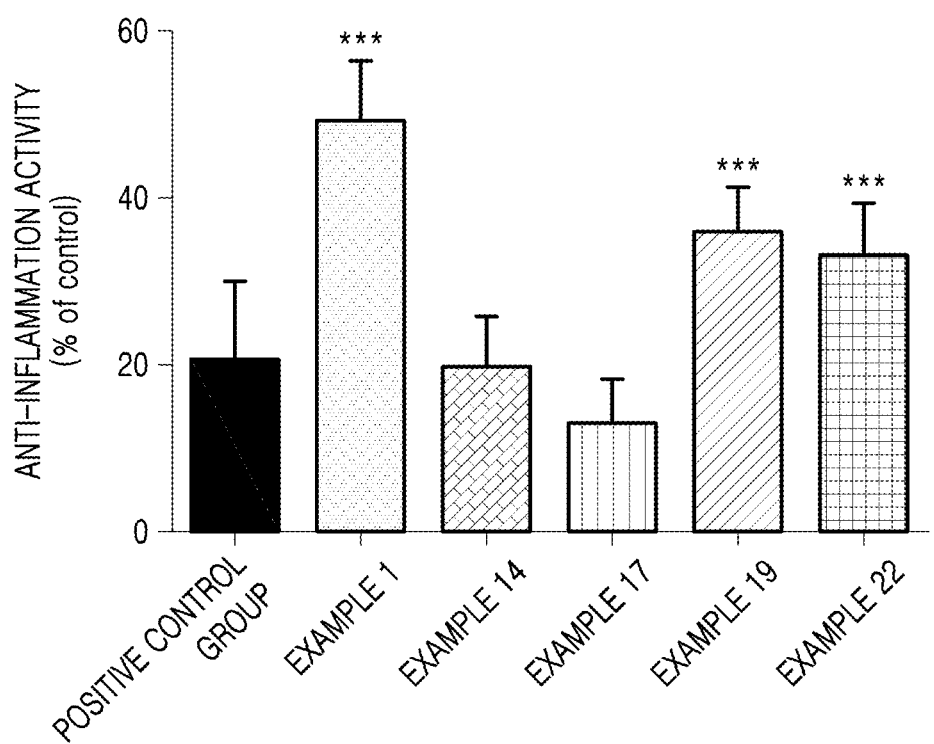
FIGS. 1 and 2 are graphs showing edema inhibition rates of compounds according to examples of the present disclosure, as results of an anti-inflammation test in a croton oil-induced inflammation animal model.

One or more embodiments of the present disclosure will now be described in detail with reference to the following examples. However, these examples are only for illustrative purposes and are not intended to limit the scope of the one or more embodiments of the present disclosure.

Unless stated otherwise in the following examples, reagents, starting materials, and solvents used in the following examples were purchased from commercial providers (for example, Aldrich, Fluka, Sigma, Acros, DAEJUNG Chemicals & Metals Co., Ltd., TCI, and the like), and used without additional purification. Purification involved in synthesis processes was performed by flash column chromatography using Silica gel 60 (0.040-0.063 mm) (available from Merck).

1. Intermediate Preparation Example

Some compounds used in the following examples were synthesized using intermediates which were synthesized as follows.

(1.1) Intermediate 1: Tert-butyl (R)-(1-benzylpyrrolidine-3-yl)carbamate

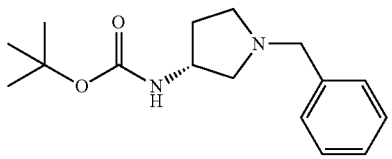 [SMILES: CC(C)(C)OC(=O)N[C@@H]1CCN(Cc2ccccc2)C1]

5.000 g of (3R)-(−)-1-benzyl-3-aminopyrrolidine hydrochloride (available from Hangzhou Tacon Co., Ltd.) was added to a 500-mL round-bottomed flask, and 117.5 mL of deionized water and 117.5 mL of acetonitrile were sequentially added thereto. After 5.924 g of sodium hydrogen carbonate ($NaHCO_3$) and 6.218 g of di-tert-butyl dicarbamate ($Boc_2O$) were sequentially added thereto, the reaction mixture was vigorously stirred overnight. An organic phase was separated from the reaction mixture, and then the resulting aqueous phase was extracted twice with 50 mL of dichloromethane ($CH_2Cl_2$). The collected organic phase was distilled under reduced pressure. The resulting residue was purified by flash column chromatography (MeOH:$CH_2Cl_2$=2:98). As a result, 4.235 g of tert-butyl (R)-(1-benzylpyrrolidine-3-yl)carbamate was obtained with a yield of about 65.2%.

$^1$H NMR (400 MHz, $CDCl_3$) δ 7.36-7.26 (m, 5H), 4.86 (bs, 1H), 4.18 (bs, 1H), 3.61 (s, 2H), 2.79 (bs, 1H), 2.65-2.61 (m, 1H), 2.54 (d, J=8.0 Hz, 1H), 2.34-2.25 (m, 2H), 1.61-1.51 (m, 1H), 1.46 (s, 9H).

(1.2) Intermediate 2: (R)-1-benzyl-N-methylpyrrolidine-3-amine

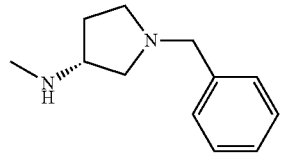

After 3.204 g of tert-butyl (R)-(1-benzylpyrrolidine-3-yl) carbamate was added to a 100-mL round-bottomed flask, 58.0 mL of tetrahydrofuran and 2.639 g of lithium aluminum hydride ($LiAlH_4$) were sequentially added thereto. The reaction mixture was refluxed overnight and then cooled at 0° C. 2.7 mL of deionized water was slowly added to the reaction mixture while cooling. After the reaction mixture was stirred for about 5 minutes, 2.7 mL of a 15% sodium hydroxide (NaOH) aqueous solution was added thereto. The reaction mixture was further stirred for about 5 minutes, and then 8.1 mL of deionized water was added thereto to terminate the reaction. The reaction mixture was filtered through a Celite™ 545 filter agent (available from DAEJUNG Chemicals & Metals Co., Ltd.). The resulting filtrate was concentrated under reduced pressure. The resulting residue was purified by flash column chromatography (MeOH:$CH_2Cl_2$:$NH_4OH$=5:90:5). As a result, 2.174 g of (R)-1-benzyl-N-methylpyrrolidine-3-amine was obtained with a yield of about 98.6%.

$^1$H NMR (400 MHz, $CDCl_3$) δ7.34-7.24 (m, 5H), 3.62 (s, 2H), 3.25-3.19 (m, 1H), 2.74 (dd, J=9.4, 6.8 Hz, 1H), 2.64 (dt, J=8.6, 6.0 Hz, 1H), 2.52 (dt, J=8.4, 6.0 Hz, 1H), 2.41-2.37 (m, 1H), 2.38 (s, 3H), 2.19-2.09 (m, 1H), 2.02 (bs, 1H), 1.63-1.56 (m, 1H).

(1.3) Intermediate 3: (R)—N-(1-benzylpyrrolidine-3-yl)-N-methyl-7H-pyrrolo[2,3-d]pyrimidine-4-amine

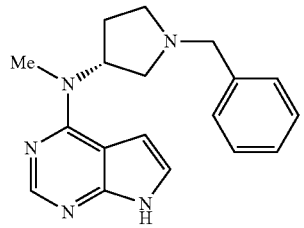 [SMILES: CN(c1ncnc2[nH]ccc12)[C@@H]1CCN(Cc2ccccc2)C1]

After 419.5 mg of (R)-1-benzyl-N-methylpyrrolidine-3-amine was added to a 50-mL round-bottomed flask, 11.0 mL of deionized water and 372.4 mg of 6-chloro-7-deazapurine (available from Acros) were sequentially added thereto. After 609.4 mg of potassium carbonate ($K_2CO_3$) was added to the reaction mixture, the reaction mixture was refluxed for about 24 hours, and then cooled at room temperature. The reaction mixture was extracted three times with 20.0 mL of dichloromethane ($CH_2Cl_2$) to collect an organic phase. The collected organic phase was concentrated under reduced pressure. The resulting residue was purified by flash column chromatography (MeOH:$CH_2Cl_2$=2:98). As a result, 506.9 mg of (R)—N-(1-benzylpyrrolidine-3-yl)-N-methyl-7H-pyrrolo[2,3-d]pyrimidine-4-amine was obtained with a yield of about 74.8%.

$^1$H NMR (400 MHz, CDCl$_3$) δ10.40 (s, 1H), 8.29 (s, 1H), 7.51-7.20 (m, 5H), 7.03 (s, 1H), 6.59 (d, J=2.2 Hz, 1H), 5.66 (s, 1H), 3.65 (dd, J=62.5, 12.9 Hz, 2H), 3.42 (s, 3H), 2.98 (dd, J=13.5, 7.8 Hz, 1H), 2.83 (dd, J=10.3, 3.4 Hz, 1H), 2.69-2.53 (m, 1H), 2.44-2.21 (m, 2H), 1.96-1.83 (m, 1H).

(1.4) Intermediate 4: (R)—N-methyl-N-(pyrrolidine-3-yl)-7H-pyrrolo[2,3-d]pyrimidine-4-amine

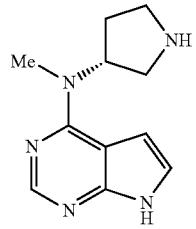 [SMILES: CN(c1ncnc2[nH]ccc12)[C@@H]1CCNC1]

638.1 mg of (R)—N-(1-benzylpyrrolidine-3-yl)-N-methyl-7H-pyrrolo[2,3-d]pyrimidine-4-amine was added to a 100-mL round-bottomed flask and then dissolved with 20.8 mL of methanol. After 638.1 mg of a 10 w/w % palladium/carbon (Pd/C) (available from Acros) was added thereto, a hydrogen-containing balloon was installed on the reaction flask. The reaction mixture was vigorously stirred overnight and then filtered through a Celite™ 545 filter agent. The resulting filtrate was concentrated under reduced pressure, and then the resulting residue was purified by flash column chromatography (MeOH:CH$_2$Cl$_2$=2:98). The resulting fraction was concentrated under reduced pressure and then further under vacuum. As a result, 324.6 mg of (R)—N-methyl-N-(pyrrolidine-3-yl)-7H-pyrrolo[2,3-d]pyrimidine-4-amine was obtained with a yield of about 72.0%.

$^1$H NMR (400 MHz, CDCl$_3$) δ12.16 (bs, 1H), 8.33 (s, 1H), 7.09 (d, J=3.5 Hz, 1H), 6.58 (d, J=3.4 Hz, 1H), 5.62-5.42 (m, 1H), 3.42-3.32 (m, 3H), 3.29 (dd, J=11.5, 8.4 Hz, 1H), 3.24-3.12 (m, 1H), 3.10-3.01 (m, 1H), 2.98 (dd, J=11.5, 6.2 Hz, 1H), 2.66 (bs, 1H), 2.26-2.10 (m, 1H), 1.91 (td, J=14.9, 7.6 Hz, 1H).

Example 1. (R)-3-(3-(methyl(7H-pyrrolo[2,3-d]pyrimidine-4-yl)amino)pyrrolidine-1-yl)-3-oxopropanenitrile

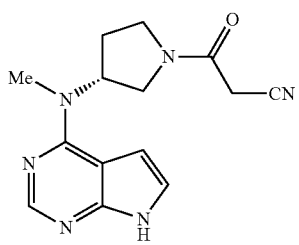 [SMILES: CN(c1ncnc2[nH]ccc12)[C@@H]1CCN(C(=O)CC#N)C1]

103 mg of (R)—N-methyl-N-(pyrrolidine-3-yl)-7H-pyrrolo[2,3-d]pyrimidine-4-amine was added to a 10-mL round-bottomed flask and then dissolved with 4.70 mL of n-butanol. After 0.505 mL of ethyl cyanoacetate was added thereto, the reaction mixture was treated with 0.0360 mL of 1,8-diazabicyclo[5.4.0]undec-7-ene (DBU), and then heated at about 80° C. for about 24 hours. After termination of the reaction, the reaction solution was distilled under reduced pressure to remove the solvent. The resulting residue was purified by flash column chromatography (MeOH:CH$_2$Cl$_2$=2:98). The resulting fraction was concentrated under reduced pressure and then further under vacuum. As a result, 101 mg of (R)-3-(3-(methyl(7H-pyrrolo[2,3-d]pyrimidine-4-yl)amino)pyrrolidine-1-yl)-3-oxopropanenitrile was obtained with a yield of about 74.8%.

$^1$H NMR (400 MHz, CDCl$_3$) δ11.48 (s, 1H), 8.31 (s, 1H), 7.13 (s, 1H), 6.58 (s, 1H), 5.74 (d, J=7.8 Hz, 1H), 3.87 (s, 2H), 3.79-3.57 (m, 2H), 3.48 (s, 2H), 3.34 (d, J=14.9 Hz, 3H), 2.46-2.11 (m, 2H).

LRMS (ESI) calcd for (C$_{14}$H$_{16}$N$_6$O+H$^+$) 285.2, found 285.2.

Example 2. (R)-3-(3-(methyl(7H-pyrrolo[2,3-d]pyrimidine-4-yl)amino)pyrrolidine-1-yl)propanenitrile

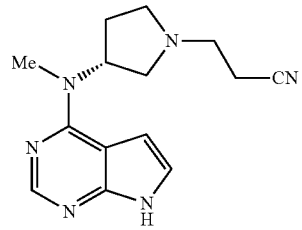 [SMILES: CN(c1ncnc2[nH]ccc12)[C@@H]1CCN(CCC#N)C1]

60.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0240 mL of 3-bromopropionitrile was added thereto, the reaction mixture was treated with 0.0720 mL of N,N-diisopropylethylamine, and then stirred at room temperature for about 5 hours. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 55.3 mg of (R)-3-(3-(methyl(7H-pyrrolo[2,3-d]pyrimidine-4-yl)amino)pyrrolidine-1-yl)propanenitrile was obtained with a yield of about 74.7%.

$^1$H NMR (400 MHz, CDCl$_3$) δ9.65 (s, 1H), 8.30 (s, 1H), 7.05 (d, J=3.6 Hz, 1H), 6.62 (d, J=3.6 Hz, 1H), 5.75-5.73 (m, 1H), 3.44 (s, 3H), 3.11-3.06 (m, 1H), 2.98-2.95 (m, 1H), 2.87-2.83 (m, 1H), 2.78-2.72 (m, 1H), 2.67 (dd, J=8.8, 9.6 Hz, 1H), 2.60 (t, J=6.8 Hz, 2H), 2.41-2.30 (m, 2H), 1.99-1.90 (m, 1H).

LRMS (ESI) calcd for (C$_{14}$H$_{18}$N$_6$+H$^+$) 271.2, found 271.1.

Example 3. (R)—N-(1-butylpyrrolidine-3-yl)-N-methyl-7H-pyrrolo[2,3-d]pyrimidine-4-amine

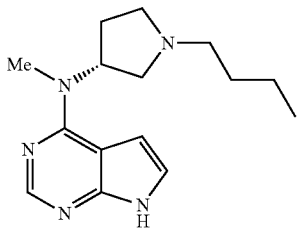 [SMILES: CCCCN1CC[C@@H](N(C)c2ncnc3[nH]ccc23)C1]

80.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane ($CH_2Cl_2$). After 0.0420 mL of 1-bromobutane was added thereto, the reaction mixture was treated with 0.0960 mL of N,N-diisopropylethylamine. After 20 droplets of N,N-dimethylformamide was added thereto, the resulting reaction mixture was stirred at room temperature for about 5 hours. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 90.0 mg of (R)—N-(1-butylpyrrolidine-3-yl)-N-methyl-7H-pyrrolo[2,3-d]pyrimidine-4-amine was obtained with a yield of about 83.3%.

$^1$H NMR (400 MHz, $CDCl_3$) δ10.05 (s, 1H), 8.29 (s, 1H), 7.09 (d, J=3.6 Hz, 1H), 6.63 (d, J=3.6 Hz, 1H), 5.69 (s, 1H), 3.50 (d, J=4.4 Hz, 4H), 2.92-2.85 (m, 3H), 2.39 (s, 2H), 1.76 (s, 4H), 1.48-1.44 (m, 2H), 0.99 (t, J=7.6 Hz, 3H).

LRMS (ESI) calcd for ($C_{15}H_{23}N_5$+$H^+$) 274.2, found 274.2.

Example 4. (R)-2-azido-1-(3-(methyl(7H-pyrrolo[2,3-d]pyrimidine-4-yl)amino)pyrrolidine-1-yl)ethane-1-one

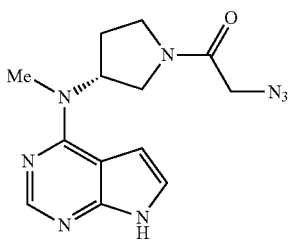 [SMILES: CN(c1ncnc2[nH]ccc12)[C@@H]1CCN(C(=O)CN=[N+]=[N-])C1]

247 mg of 2-azidoacetic acid was added to a 25-mL round-bottomed flask and then dissolved with 8.00 mL of N,N-dimethylformamide. After 503 mg of dicyclohexylcarbodiimide and 0.850 mL of N,N-diisopropylethylamine were added thereto, the reaction mixture was stirred for about 15 minutes. 265 mg of (R)—N-methyl-N-(pyrrolidine-3-yl)-7H-pyrrolo[2,3-d]pyrimidine-4-amine was added to another 25-mL round-bottomed flask, and then the previously prepared 2-azidoacetic acid mixture was added thereto. This mixture was refluxed overnight. The mixture was cooled down to room temperature and then filtered through a Celite™ 545 filter agent. The resulting fraction was concentrated under reduced pressure, and then the resulting residue was purified by flash column chromatography (MeOH:$CH_2Cl_2$=2:98). The resulting fraction was concentrated under reduced pressure and then further under vacuum. As a result, 19.3 mg of (R)-2-azido-1-(3-(methyl(7H-pyrrolo[2,3-d]pyrimidine-4-yl)amino)pyrrolidine-1-yl)ethane-1-one was obtained with a yield of about 5.27%.

$^1$H NMR (400 MHz, $CDCl_3$) δ9.64 (s, 1H), 8.33 (s, 1H), 7.11-7.02 (m, 1H), 6.62-6.61 (m, 1H), 5.81-5.71 (m, 1H), 3.97-3.90 (m, 3H), 3.84-3.78 (m, 1H), 3.69-3.51 (m, 2H), 3.37-3.33 (m, 3H), 2.26-2.12 (m, 2H).

LRMS (ESI) calcd for ($C_{13}H_{16}N_8O$+$H^+$) 301.2, found 301.1.

Example 5. (R)-3-methyl-1-(3-(methyl(7H-pyrrolo[2,3-d]pyrimidine-4-yl)amino)pyrrolidine-1-yl)butane-1-one

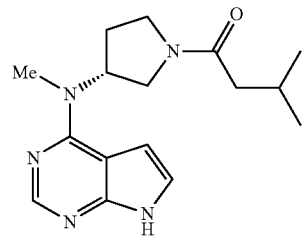 [SMILES: CC(C)CC(=O)N1CC[C@@H](N(C)c2ncnc3[nH]ccc23)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane ($CH_2Cl_2$). After 0.0390 mL of isovaleryl chloride was added thereto, the reaction mixture was treated with 0.0590 mL of N,N-diisopropylethylamine and stirred overnight at room temperature. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 66.7 mg of (R)-3-methyl-1-(3-(methyl(7H-pyrrolo[2,3-d]pyrimidine-4-yl)amino)pyrrolidine-1-yl)butane-1-one was obtained with a yield of about 68.7%.

$^1$H NMR (400 MHz, $CDCl_3$) δ9.87 (d, J=14.8 Hz, 1H), 8.35 (d, J=4.4 Hz, 1H), 7.11-7.08 (m, 1H), 6.62-6.61 (m, 1H), 5.78-5.66 (m, 1H), 3.92-3.69 (m, 2H), 3.61-3.39 (m, 2H), 3.36 (d, J=12.4 Hz, 3H), 2.33 (m, 5H), 1.03-0.99 (m, 6H).

LRMS (ESI) calcd for ($C_{16}H_{23}N_5O$+$H^+$) 302.2, found 302.2.

Example 6. Isobutyl (R)-3-(methyl(7H-pyrrolo[2,3-d]pyrimidine-4-yl)amino)pyrrolidine-1-carboxylate

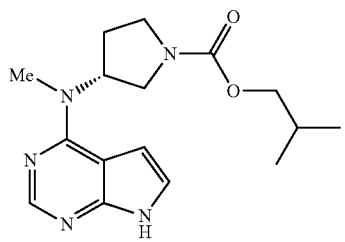 [SMILES: CC(C)COC(=O)N1CC[C@@H](N(C)c2ncnc3[nH]ccc23)C1]

70.0 mg of (R)—N-methyl-N-(pyrrolidine-3-yl)-7H-pyrrolo[2,3-d]pyrimidine-4-amine was added to a 5-mL round-bottomed flask, and then dissolved with 1.00 mL of dichloromethane (CH$_2$Cl$_2$). After 0.0420 mL of isobutyl chloroformate was added thereto, the reaction mixture was treated with 0.0560 mL of N,N-diisopropylethylamine, and then stirred overnight at room temperature. The reaction mixture was concentrated under reduced pressure and then purified by flash column chromatography (MeOH:CH$_2$Cl$_2$=2:98). The resulting fraction was concentrated under reduced pressure and then further under vacuum. As a result, 41.0 mg of isobutyl (R)-3-(methyl(7H-pyrrolo[2,3-d]pyrimidine-4-yl)amino)pyrrolidine-1-carboxylate was obtained with a yield of about 40.2%.

$^1$H NMR (400 MHz, CDCl$_3$) δ9.52 (s, 1H), 8.34 (s, 1H), 7.08 (s, 1H), 6.78 (s, 1H), 5.73-5.71 (m, 1H), 3.92 (d, J=6.4 Hz, 2H), 3.78-3.68 (m, 2H), 3.55-3.39 (m, 2H), 3.34 (s, 3H), 2.22-2.12 (m, 2H), 1.97-1.96 (m, 1H), 0.97-0.95 (m, 6H). LRMS (ESI) calcd for (C$_{16}$H$_{23}$N$_5$O$_2$+H$^+$) 318.2, found 318.2.

Example 7. (R)-3-(methyl(7H-pyrrolo[2,3-d]pyrimidine-4-yl)amino)-N-phenylpyrrolidine-1-carboxamide

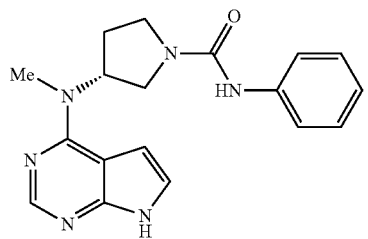 [SMILES: CN(c1ncnc2[nH]ccc12)[C@@H]1CCN(C(=O)Nc2ccccc2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0350 mL of phenyl isocyanate was added thereto, the reaction mixture was treated with 0.0590 mL of N,N-diisopropylethylamine, and then stirred at room temperature for about 5 hours. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 81.5 mg of (R)-3-(methyl(7H-pyrrolo[2,3-d]pyrimidine-4-yl)amino)-N-phenylpyrrolidine-1-carboxamide was obtained with a yield of about 75.4%.

$^1$H NMR (400 MHz, CDCl$_3$) δ10.61 (s, 1H), 8.35 (s, 1H), 7.45 (d, J=7.6 Hz, 2H), 7.33 (t, J=7.6 Hz, 2H), 7.12 (m, 1H), 7.05 (t, J=8.0 Hz, 1H), 6.62 (d, J=2.8 Hz, 1H), 6.25 (s, 1H), 5.83-5.72 (m, 1H), 3.90 (q, J=8.4, 10 Hz, 1H), 3.83-3.77 (m, 1H), 3.61-3.54 (m, 1H), 3.52-3.47 (m, 1H), 3.38 (s, 3H), 2.35-2.20 (m, 2H).

LRMS (ESI) calcd for (C$_{18}$H$_{20}$N$_6$O+H$^+$) 337.2, found 337.2.

Example 8. (R)—N-methyl-N-(1-(methylsulfonyl)pyrrolidine-3-yl)-7H-pyrrolo[2,3-d]pyrimidine-4-amine

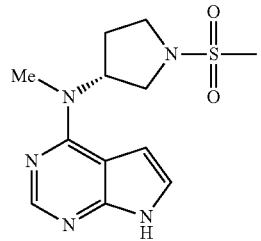

70.0 mg of (R)—N-methyl-N-(pyrrolidine-3-yl)-7H-pyrrolo[2,3-d]pyrimidine-4-amine was added to a 5-mL round-bottomed flask, and then dissolved with 1.0 mL of dichloromethane (CH$_2$Cl$_2$). After 0.0250 mL of methanesulfonyl chloride was added thereto, the reaction mixture was treated with 0.0590 mL of N,N-diisopropylethylamine, and then stirred overnight at room temperature. The reaction mixture was concentrated under reduced pressure and then purified by flash column chromatography (MeOH:CH$_2$Cl$_2$=2:98). The resulting fraction was concentrated under reduced pressure and then further under vacuum. As a result, 40.0 mg of (R)—N-methyl-N-(1-(methylsulfonyl)pyrrolidine-3-yl)-7H-pyrrolo[2,3-d]pyrimidine-4-amine was obtained with a yield of about 42.1%.

$^1$H NMR (400 MHz, CDCl$_3$) δ9.63 (s, 1H), 8.36 (s, 1H), 7.10 (s, 1H), 6.62 (s, 1H), 5.85-5.77 (m, 1H), 3.80→3.69 (m, 1H), 3.66-3.61 (m, 1H), 3.44-3.30 (m, 5H), 2.93 (s, 3H), 2.36-2.17 (m, 2H).

LRMS (ESI) calcd for (C$_{12}$H$_{17}$N$_5$O$_2$S+H$^+$) 296.1, found 296.1.

Example 9. (R)—N-methyl-N-(1-((trifluoromethyl)sulfonyl)pyrrolidine-3-yl)-7H-pyrrolo[2,3-d]pyrimidine-4-amine

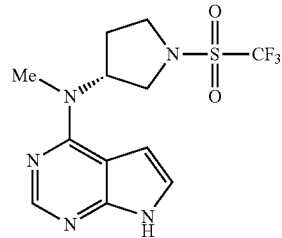

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0340 mL of trifluoromethanesulfonyl chloride was added thereto, the reaction mixture was treated with 0.0590 mL of N,N-diisopropylethylamine, and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 72.0 mg of (R)—N-methyl-N-(1-((trifluoromethyl)sulfonyl)pyrrolidine-3-yl)-7H-pyrrolo[2,3-d]pyrimidine-4-amine was obtained with a yield of about 64.3%.

$^1$H NMR (400 MHz, CDCl$_3$) δ10.00 (s, 1H), 8.35 (s, 1H), 7.13-7.12 (m, 1H), 6.62-6.60 (m, 1H), 5.93-5.79 (m, 1H), 4.02-3.86 (m, 2H), 3.68-3.61 (m, 1H), 3.57 (t, J=8.8 Hz, 1H), 3.38 (s, 3H), 2.39-2.23 (m, 2H).

LRMS (ESI) calcd for (C$_{12}$H$_{14}$F$_3$N$_5$O$_2$S+H$^+$) 350.1, found 350.1.

Example 10. (R)—N-(1-(ethylsulfonyl)pyrrolidine-3-yl)-N-methyl-7H-pyrrolo[2,3-d]pyrimidine-4-amine

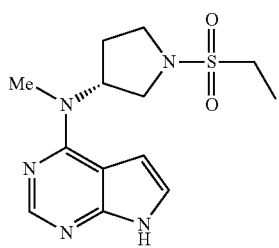 [SMILES: CCS(=O)(=O)N1CC[C@@H](N(C)c2ncnc3[nH]ccc23)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0310 mL of ethanesulfonyl chloride was added thereto, the reaction mixture was treated with 0.0590 mL of N,N-diisopropylethylamine, and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 53.4 mg of (R)—N-(1-(ethylsulfonyl)pyrrolidine-3-yl)-N-methyl-7H-pyrrolo[2,3-d]pyrimidine-4-amine was obtained with a yield of about 53.6%.

$^1$H NMR (400 MHz, CDCl$_3$) δ10.30 (s, 1H), 8.33 (s, 1H), 7.12 (s, 1H), 6.74 (s, 1H), 5.83-5.79 (m, 1H), 3.76-3.67 (m, 2H), 3.55-3.40 (m, 2H), 3.38 (s, 3H), 3.12-3.07 (m, 2H), 2.34-2.15 (m, 2H), 1.46 (t, J=7.2 Hz, 3H).

LRMS (ESI) calcd for (C$_{13}$H$_{19}$N$_5$O$_2$S+H$^+$) 310.1, found 310.1.

Example 11. (R)—N-methyl-N-(1-(propylsulfonyl)pyrrolidine-3-yl)-7H-pyrrolo[2,3-d]pyrimidine-4-amine

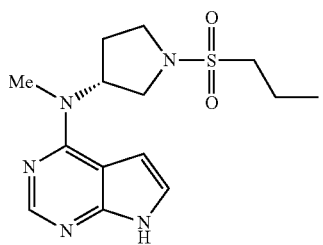 [SMILES: CCCS(=O)(=O)N1CC[C@@H](N(C)c2ncnc3[nH]ccc23)C1]

60.0 mg of (R)—N-methyl-N-(pyrrolidine-3-yl)-7H-pyrrolo[2,3-d]pyrimidine-4-amine was added to a 5-mL round-bottomed flask and then dissolved with 0.600 mL of dichloromethane (CH$_2$Cl$_2$). After 0.0320 mL of 1-propanesulfonyl chloride was added thereto, the reaction mixture was treated with 0.0720 mL of N,N-diisopropylethylamine, and then stirred at room temperature for about 5 hours. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 49.0 mg of (R)—N-methyl-N-(1-(propylsulfonyl)pyrrolidine-3-yl)-7H-pyrrolo[2,3-d]pyrimidine-4-amine was obtained with a yield of about 54.9%.

$^1$H NMR (400 MHz, CDCl$_3$) δ9.64 (s, 1H), 8.32 (s, 1H), 7.09-7.08 (m, 1H), 6.62-6.61 (m, 1H), 5.83-5.77 (m, 1H), 3.74-3.65 (m, 2H), 3.44-3.38 (m, 2H), 3.37 (s, 3H), 3.04-3.00 (m, 2H), 2.40-2.25 (m, 1H), 2.24-2.12 (m, 1H), 1.97-1.87 (m, 2H), 1.13 (t, J=7.6 Hz, 3H).

LRMS (ESI) calcd for (C$_{14}$H$_{21}$N$_5$O$_2$S+H$^+$) 324.1, found 324.1.

Example 12. (R)—N-(1-(isopropylsulfonyl)pyrrolidine-3-yl)-N-methyl-7H-pyrrolo[2,3-d]pyrimidine-4-amine

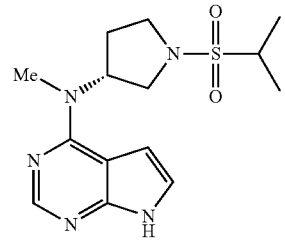 [SMILES: CC(C)S(=O)(=O)N1CC[C@@H](N(C)c2ncnc3[nH]ccc23)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0360 mL of 2-propanesulfonyl chloride was added thereto, the reaction mixture was treated with 0.0590 mL of N,N-diisopropylethylamine, and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 36.0 mg of (R)—N-(1-(isopropylsulfonyl)pyrrolidine-3-yl)-N-methyl-7H-pyrrolo[2,3-d]pyrimidine-4-amine was obtained with a yield of about 34.6%.

$^1$H NMR (400 MHz, CDCl$_3$) δ8.93 (s, 1H), 8.35 (s, 1H), 7.07-7.02 (m, 1H), 6.62-6.61 (m, 1H), 5.90-5.75 (m, 1H), 3.80→3.68 (m, 2H), 3.50-3.44 (m, 2H), 3.36 (s, 3H), 3.33-3.26 (m, 1H), 2.30-2.13 (m, 2H), 1.44 (d, J=6.8 Hz, 6H).

LRMS (ESI) calcd for (C$_{14}$H$_{21}$N$_5$O$_2$S+H$^+$) 324.2, found 324.1.

Example 13. (R)—N-methyl-N-(1-((1-methyl-1H-imidazole-4-yl)sulfonyl)pyrrolidine-3-yl)-7H-pyrrolo[2,3-d]pyrimidine-4-amine

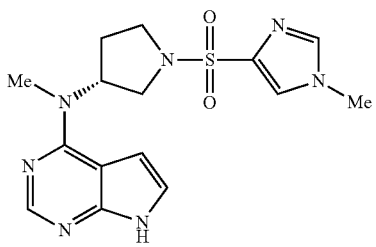 [SMILES: CN(c1ncnc2[nH]ccc12)[C@@H]1CCN(S(=O)(=O)c2cn(C)cn2)C1]

50.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane ($CH_2Cl_2$). After 39.7 mg of 1-methyl-1H-imidazole-4-sulfonyl chloride was added thereto, the reaction mixture was treated with 0.0370 mL of N,N-diisopropylethylamine and then stirred at room temperature for about 1 hour. The resulting residue was purified by flash column chromatography (MeOH:$CH_2Cl_2$=0:100→1:80→1:50). The resulting fraction was concentrated under reduced pressure and then further under vacuum. As a result, 17.0 mg of (R)—N-methyl-N-(1-((1-methyl-1H-imidazole-4-yl)sulfonyl)pyrrolidine-3-yl)-7H-pyrrolo[2,3-d]pyrimidine-4-amine was obtained with a yield of about 22.4%.

$^1$H NMR (400 MHz, CDCl$_3$) δ9.32 (s, 1H), 8.27 (s, 1H), 7.54 (dd, J=11.2, 3.6 Hz, 2H), 7.06 (d, J=1.6 Hz, 1H), 6.36 (d, J=3.2 Hz, 1H), 5.71-5.63 (m, 1H), 3.81 (s, 3H), 3.78-3.67 (m, 2H), 3.50-3.42 (m, 2H), 3.34 (s, 3H), 2.22-2.09 (m, 2H).

LRMS (ESI) calcd for ($C_{15}H_{19}N_7O_2S+H^+$) 362.1, found 362.1.

Example 14. (R)—N-methyl-N-(1-(phenylsulfonyl)pyrrolidine-3-yl)-7H-pyrrolo[2,3-d]pyrimidine-4-amine

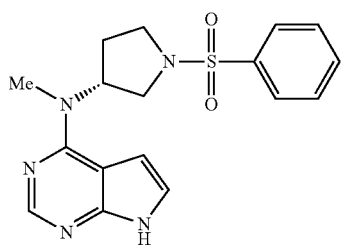 [SMILES: CN(c1ncnc2[nH]ccc12)[C@@H]1CCN(S(=O)(=O)c2ccccc2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane ($CH_2Cl_2$). After 0.0410 mL of benzenesulfonyl chloride was added thereto, the reaction mixture was treated with 0.0590 mL of N,N-diisopropylethylamine and then stirred overnight at room temperature. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 101 mg of (R)—N-methyl-N-(1-(phenylsulfonyl)pyrrolidine-3-yl)-7H-pyrrolo[2,3-d]pyrimidine-4-amine was obtained with a yield of about 84.2%.

$^1$H NMR (400 MHz, CDCl$_3$) δ10.32 (s, 1H), 8.25 (s, 1H), 7.90 (d, J=8.0 Hz, 2H), 7.69-7.54 (m, 3H), 7.02 (s, 1H), 6.48 (s, 1H), 5.65-5.58 (m, 1H), 3.69-3.65 (m, 1H), 3.59-3.35 (m, 2H), 3.29 (s, 3H), 3.15-3.04 (m, 1H), 2.32-2.02 (m, 2H).

LRMS (ESI) calcd for ($C_{17}H_{19}N_5O_2S+H^+$) 358.1, found 358.1.

Example 15. (R)—N-(1-((2-fluorophenyl)sulfonyl)pyrrolidine-3-yl)-N-methyl-7H-pyrrolo[2,3-d]pyrimidine-4-amine

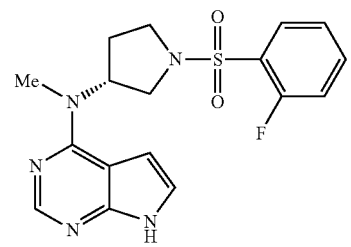 [SMILES: CN(c1ncnc2[nH]ccc12)[C@@H]1CCN(S(=O)(=O)c2ccccc2F)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane ($CH_2Cl_2$). After 0.0450 mL of 2-fluorobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:$CH_2Cl_2$=0:100→1:80→1:50). The resulting fraction was concentrated under reduced pressure and then further under vacuum. As a result, 96.8 mg of (R)—N-(1-((2-fluorophenyl)sulfonyl)pyrrolidine-3-yl)-N-methyl-7H-pyrrolo[2,3-d]pyrimidine-4-amine was obtained with a yield of about 80.6%.

$^1$H NMR (400 MHz, CDCl$_3$) δ9.71 (s, 1H), 8.27 (s, 1H), 7.97-7.93 (m, 1H), 7.67-7.61 (m, 1H), 7.35-7.27 (m, 2H), 7.08-7.02 (m, 1H), 6.58 (dd, J=3.6, 2.0 Hz, 1H), 5.76-5.68 (m, 1H), 3.80→3.75 (m, 1H), 3.64 (dd, J=10.4, 8.4 Hz, 1H), 3.45 (dd, J=10.4, 6.8 Hz, 1H), 3.40-3.36 (m, 1H), 3.33 (s, 3H), 2.28-2.16 (m, 2H).

LRMS (ESI) calcd for ($C_{17}H_{18}FN_5O_2S+H^+$) 376.1, found 376.1.

Example 16. (R)—N-(1-((3-fluorophenyl)sulfonyl)pyrrolidine-3-yl)-N-methyl-7H-pyrrolo[2,3-d]pyrimidine-4-amine

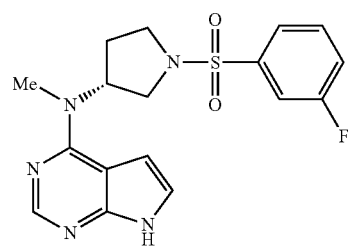 [SMILES: CN(c1ncnc2[nH]ccc12)[C@@H]1CCN(S(=O)(=O)c2cccc(F)c2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 0.0450 mL of 3-fluorobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 101 mg of (R)—N-(1-((3-fluorophenyl)sulfonyl)pyrrolidine-3-yl)-N-methyl-7H-pyrrolo[2,3-d]pyrimidine-4-amine was obtained with a yield of about 84.0%.

$^1$H NMR (400 MHz, CDCl$_3$) δ9.54 (s, 1H), 8.25 (s, 1H), 7.69 (d, J=8.0 Hz, 1H), 7.62-7.57 (m, 2H), 7.38 (dt, J=8.4, 2.4 Hz, 1H), 7.07 (t, J=2.8 Hz, 1H), 6.57 (d, J=1.6 Hz, 1H), 5.67-5.59 (m, 1H), 3.72-3.67 (m, 1H), 3.47 (t, J=10.4 Hz, 1H), 3.39 (dd, J=10.4, 6.8 Hz, 1H), 3.32 (s, 3H), 3.18-3.11 (m, 1H), 2.25-2.10 (m, 2H).

LRMS (ESI) calcd for (C$_{17}$H$_{18}$FN$_5$O$_2$S+H$^+$) 376.1, found 376.1.

Example 17. (R)—N-(1-((4-fluorophenyl)sulfonyl)pyrrolidine-3-yl)-N-methyl-7H-pyrrolo[2,3-d]pyrimidine-4-amine

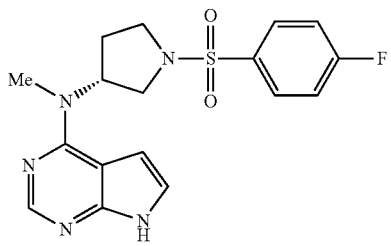 [SMILES: CN(c1ncnc2[nH]ccc12)[C@@H]1CCN(S(=O)(=O)c2ccc(F)cc2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 66.2 mg of 4-fluorobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 93.5 mg of (R)—N-(1-((4-fluorophenyl)sulfonyl)pyrrolidine-3-yl)-N-methyl-7H-pyrrolo[2,3-d]pyrimidine-4-amine was obtained with a yield of about 77.8%.

$^1$H NMR (400 MHz, CDCl$_3$) δ10.35 (s, 1H), 8.26 (s, 1H), 7.91 (dd, J=9.2, 5.2 Hz, 2H), 7.31-7.25 (m, 2H), 7.09 (d, J=2.8 Hz, 1H), 6.55 (d, J=3.2 Hz, 1H), 5.67-5.59 (m, 1H), 3.70-3.65 (m, 1H), 3.45 (dd, J=10.4, 8.4 Hz, 1H), 3.37 (dd, J=10.8, 6.8 Hz, 1H), 3.32 (s, 3H), 3.15-3.08 (m, 1H), 2.25-2.06 (m, 2H).

LRMS (ESI) calcd for (C$_{17}$H$_{18}$FN$_5$O$_2$S+H$^+$) 376.1, found 376.1.

Example 18. (R)-2-((3-(methyl(7H-pyrrolo[2,3-d]pyrimidine-4-yl)amino)pyrrolidine-1-yl)sulfonyl)benzonitrile

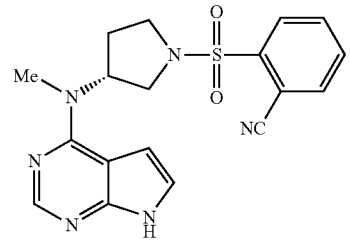 [SMILES: CN(c1ncnc2[nH]ccc12)[C@@H]1CCN(S(=O)(=O)c2ccccc2C#N)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 68.6 mg of 2-cyanobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 68.8 mg of (R)-2-((3-(methyl(7H-pyrrolo[2,3-d]pyrimidine-4-yl)amino)pyrrolidine-1-yl)sulfonyl)benzonitrile was obtained with a yield of about 56.0%.

$^1$H NMR (400 MHz, CDCl$_3$) δ9.70 (s, 1H), 8.27 (s, 1H), 8.14 (d, J=7.6 Hz, 1H), 7.94 (d, J=7.6 Hz, 1H), 7.82-7.73 (m, 2H), 7.08 (t, J=3.2 Hz, 1H), 6.60 (dd, J=3.2, 1.6 Hz, 1H), 5.82-5.74 (m, 1H), 3.87-3.82 (m, 1H), 3.68 (t, J=10.0 Hz, 1H), 3.52-3.41 (s, 2H), 3.35 (s, 3H), 2.33-2.23 (m, 2H).

LRMS (ESI) calcd for (C$_{18}$H$_{18}$N$_6$O$_2$S+H$^+$) 383.1, found 383.1.

Example 19. (R)-3-((3-(methyl(7H-pyrrolo[2,3-d]pyrimidine-4-yl)amino)pyrrolidine-1-yl)sulfonyl)benzonitrile

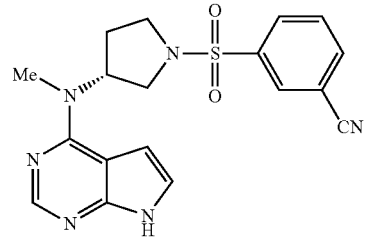 [SMILES: CN(c1ncnc2[nH]ccc12)[C@@H]1CCN(S(=O)(=O)c2cccc(C#N)c2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 68.6 mg of 3-cyanobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 88.6 mg of (R)-3-((3-(methyl(7H-pyrrolo[2,3-d]pyrimidine-4-yl)amino)pyrrolidine-1-yl)sulfonyl)benzonitrile was obtained with a yield of about 72.4%.

$^1$H NMR (400 MHz, CDCl$_3$) δ10.04 (s, 1H), 8.25 (s, 1H), 8.18 (s, 1H), 8.11 (d, J=8.0 Hz, 1H), 7.95 (d, J=7.6 Hz, 1H), 7.75 (t, J=8.0 Hz, 1H), 7.10 (t, J=3.2 Hz, 1H), 6.57 (t, J=1.6 Hz, 1H), 5.62 (t, J=7.6 Hz, 1H), 3.75-3.70 (m, 1H), 3.51 (dd, J=10.4, 8.4 Hz, 1H), 3.40 (dd, J=10.4, 6.8 Hz, 1H), 3.33 (s, 3H), 3.20-3.13 (m, 1H), 2.27-2.14 (m, 2H).

LRMS (ESI) calcd for (C$_{18}$H$_{18}$N$_6$O$_2$S+H$^+$) 383.1, found 383.1.

Example 20. (R)-4-((3-(methyl(7H-pyrrolo[2,3-d]pyrimidine-4-yl)amino)pyrrolidine-1-yl)sulfonyl)benzonitrile

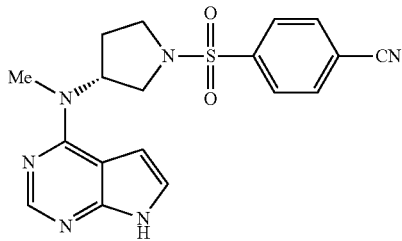

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 68.6 mg of 4-cyanobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 80.5 mg of (R)-4-((3-(methyl(7H-pyrrolo[2,3-d]pyrimidine-4-yl)amino)pyrrolidine-1-yl)sulfonyl)benzonitrile was obtained with a yield of about 65.8%.

$^1$H NMR (400 MHz, CDCl$_3$) δ9.72 (s, 1H), 8.25 (s, 1H), 8.00 (d, J=8.0 Hz, 2H), 7.90 (d, J=8.4 Hz, 2H), 7.09 (dd, J=3.6, 2.4 Hz, 1H), 6.56 (dd, J=3.6, 2.0 Hz, 1H), 5.66-5.58 (m, 1H), 3.74-3.68 (m, 1H), 3.50 (dd, J=10.4, 8.4 Hz, 1H), 3.40 (dd, J=10.4, 6.8 Hz, 1H), 3.31 (s, 3H), 3.20-3.14 (m, 1H), 2.26-2.09 (m, 2H).

LRMS (ESI) calcd for (C$_{18}$H$_{18}$N$_6$O$_2$S+H$^+$) 383.1, found 383.1.

Example 21. (R)—N-methyl-N-(1-((2-nitrophenyl)sulfonyl)pyrrolidine-3-yl)-7H-pyrrolo[2,3-d]pyrimidine-4-amine

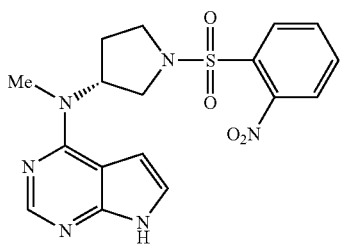 [SMILES: CN(c1ncnc2[nH]ccc12)[C@@H]1CCN(S(=O)(=O)c2ccccc2[N+](=O)[O-])C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 75.4 mg of 2-nitrobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 101 mg of (R)—N-methyl-N-(1-((2-nitrophenyl)sulfonyl)pyrrolidine-3-yl)-7H-pyrrolo[2,3-d]pyrimidine-4-amine was obtained with a yield of about 78.1%.

$^1$H NMR (400 MHz, CDCl$_3$) δ9.83 (s, 1H), 8.30 (s, 1H), 8.08 (d, J=8.4 Hz, 1H), 7.78-7.66 (m, 3H), 7.09 (s, 1H), 6.60 (s, 1H), 5.82-5.74 (m, 1H), 3.82-3.74 (m, 2H), 3.53-3.45 (m, 2H), 3.35 (s, 3H), 2.33-2.18 (m, 2H).

LRMS (ESI) calcd for (C$_{17}$H$_{18}$N$_6$O$_4$S+H$^+$) 403.1, found 403.1.

Example 22. (R)—N-methyl-N-(1-((3-nitrophenyl)sulfonyl)pyrrolidine-3-yl)-7H-pyrrolo[2,3-d]pyrimidine-4-amine

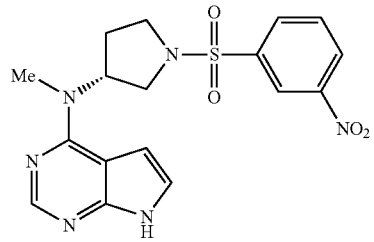 [SMILES: CN(c1ncnc2[nH]ccc12)[C@@H]1CCN(S(=O)(=O)c2cccc([N+](=O)[O-])c2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 75.4 mg of 3-nitrobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 104 mg of (R)—N-methyl-N-(1-((3-nitrophenyl)sulfonyl)pyrrolidine-3-yl)-7H-pyrrolo[2,3-d]pyrimidine-4-amine was obtained with a yield of about 81.0%.

$^1$H NMR (400 MHz, CDCl$_3$) δ10.51 (s, 1H), 8.73 (t, J=1.6 Hz, 1H), 8.52 (dd, J=8.0, 1.6 Hz, 1H), 8.24 (s, 1H), 8.22 (d, J=8.0 Hz, 1H), 7.83 (t, J=8.0 Hz, 1H), 7.10 (dd, J=3.6, 2.0 Hz, 1H), 6.56 (dd, J=3.2, 1.6 Hz, 1H), 5.67-5.61 (m, 1H), 3.78-3.73 (m, 1H), 3.54 (dd, J=10.4, 8.4 Hz, 1H), 3.43 (dd, J=10.4, 6.8 Hz, 1H), 3.33 (s, 3H), 3.23-3.17 (m, 1H), 2.27-2.14 (m, 2H).

LRMS (ESI) calcd for (C$_{17}$H$_{18}$N$_6$O$_4$S+H$^+$) 403.1, found 403.1.

Example 23. (R)—N-methyl-N-(1-((4-nitrophenyl)sulfonyl)pyrrolidine-3-yl)-7H-pyrrolo[2,3-d]pyrimidine-4-amine

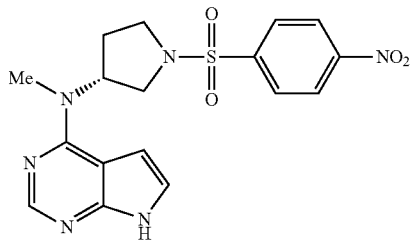 [SMILES: CN(c1ncnc2[nH]ccc12)[C@@H]1CCN(S(=O)(=O)c2ccc([N+](=O)[O-])cc2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane ($CH_2Cl_2$). After 75.4 mg of 4-nitrobenzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:$CH_2Cl_2$=0:100→1:80→1:50). The resulting fraction was concentrated under reduced pressure and then further under vacuum. As a result, 95.3 mg of (R)—N-methyl-N-(1-((4-nitrophenyl)sulfonyl)pyrrolidine-3-yl)-7H-pyrrolo[2,3-d]pyrimidine-4-amine was obtained with a yield of about 74.0%.

$^1$H NMR (400 MHz, $CDCl_3$) δ10.10 (s, 1H), 8.44 (d, J=8.4 Hz, 2H), 8.25 (s, 1H), 8.08 (d, J=8.4 Hz, 2H), 7.09 (s, 1H), 6.55 (t, J=1.6 Hz, 1H), 5.65-5.57 (m, 1H), 3.76-3.70 (m, 1H), 3.53 (t, J=10.0 Hz, 1H), 3.41 (dd, J=10.0, 6.8 Hz, 1H), 3.32 (s, 3H), 3.23-3.17 (m, 1H), 2.27-2.11 (m, 2H).

LRMS (ESI) calcd for ($C_{17}H_{18}N_6O_4S+H^+$) 403.1, found 403.0.

Example 24. (R)—N-methyl-N-(1-(m-tolylsulfonyl)pyrrolidine-3-yl)-7H-pyrrolo[2,3-d]pyrimidine-4-amine

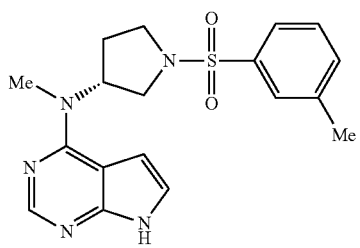 [SMILES: Cc1cccc(S(=O)(=O)N2CC[C@@H](N(C)c3ncnc4[nH]ccc34)C2)c1]

70.0 mg of (R)—N-methyl-N-(pyrrolidine-3-yl)-7H-pyrrolo[2,3-d]pyrimidine-4-amine was added to a 5-mL round-bottomed flask and then dissolved with 2.00 mL of dichloromethane ($CH_2Cl_2$). After 0.0470 mL of 3-toluenesulfonyl chloride was added thereto, the reaction mixture was treated with 0.0590 mL of N,N-diisopropylethylamine and then stirred overnight at room temperature. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 101 mg of (R)—N-methyl-N-(1-(m-tolylsulfonyl)pyrrolidine-3-yl)-7H-pyrrolo[2,3-d]pyrimidine-4-amine was obtained with a yield of about 84.9%.

$^1$H NMR (400 MHz, $CDCl_3$) δ9.33 (s, 1H), 8.24 (s, 1H), 7.69 (s, 2H), 7.47 (s, 2H), 7.06 (s, 1H), 6.55 (s, 1H), 5.63-5.58 (m, 1H), 3.69-3.65 (m, 1H), 3.48-3.35 (m, 2H), 3.30 (s, 3H), 3.13-3.06 (m, 1H), 2.48 (s, 3H), 2.19-2.02 (m, 2H).

LRMS (ESI) calcd for ($C_{18}H_{21}N_5O_2S+H^+$) 372.2, found 372.1.

Example 25. (R)—N-methyl-N-(1-tosylpyrrolidine-3-yl)-7H-pyrrolo[2,3-d]pyrimidine-4-amine

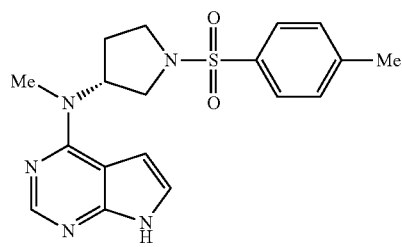 [SMILES: Cc1ccc(S(=O)(=O)N2CC[C@@H](N(C)c3ncnc4[nH]ccc34)C2)cc1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane ($CH_2Cl_2$). After 64.8 mg of p-toluenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:$CH_2Cl_2$=0:100→1:80→1:50). The resulting fraction was concentrated under reduced pressure and then further under vacuum. As a result, 87.4 mg of (R)—N-methyl-N-(1-tosylpyrrolidine-3-yl)-7H-pyrrolo[2,3-d]pyrimidine-4-amine was obtained with a yield of about 73.5%.

$^1$H NMR (400 MHz, $CDCl_3$) δ9.94 (s, 1H), 8.25 (s, 1H), 7.77 (d, J=8.0 Hz, 2H), 7.39 (d, J=8.4 Hz, 2H), 7.07 (t, J=2.8 Hz, 1H), 6.55 (d, J=2.0 Hz, 1H), 5.66-5.58 (m, 1H), 3.68-3.63 (m, 1H), 3.43-3.34 (m, 2H), 3.31 (s, 3H), 3.11-3.05 (m, 1H), 2.49 (s, 3H), 2.22-2.02 (m, 2H).

LRMS (ESI) calcd for ($C_{18}H_{21}N_5O_2S+H^+$) 372.2, found 372.1.

Example 26. (R)—N-(1-((4-methoxyphenyl)sulfonyl)pyrrolidine-3-yl)-N-methyl-7H-pyrrolo[2,3-d]pyrimidine-4-amine

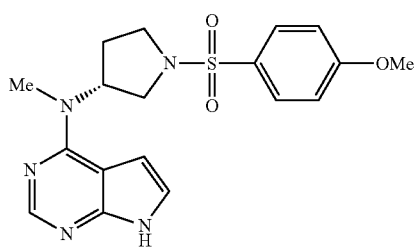 [SMILES: COc1ccc(S(=O)(=O)N2CC[C@@H](N(C)c3ncnc4[nH]ccc34)C2)cc1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 70.3 mg of 4-methoxybenzenesulfonyl chloride was added thereto, the reaction mixture was treated with 0.0590 mL of N,N-diisopropylethylamine and stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 107 mg of (R)—N-(1-((4-methoxyphenyl)sulfonyl)pyrrolidine-3-yl)-N-methyl-7H-pyrrolo[2,3-d]pyrimidine-4-amine was obtained with a yield of about 86.2%.

$^1$H NMR (400 MHz, CDCl$_3$) δ9.82 (s, 1H), 8.26 (s, 1H), 7.83 (d, J=8.8 Hz, 2H), 7.06 (d, J=8.4 Hz, 3H), 6.55 (s, 1H), 5.66-5.58 (m, 1H), 3.93 (s, 3H), 3.67-3.62 (m, 1H), 3.42-3.34 (m, 2H), 3.31 (s, 3H), 3.11-3.04 (m, 1H), 2.23-2.04 (m, 2H).

LRMS (ESI) calcd for (C$_{18}$H$_{21}$N$_5$O$_3$S+H$^+$) 388.1, found 388.1.

Example 27. (R)—N-methyl-N-(1-((4-(trifluoromethyl)phenyl)sulfonyl)pyrrolidine-3-yl)-7H-pyrrolo[2,3-d]pyrimidine-4-amine

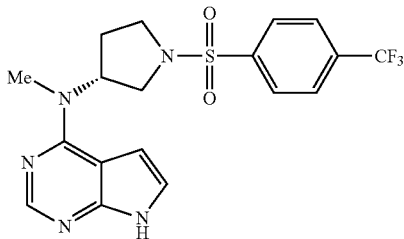

70.0 mg of (R)—N-methyl-N-(pyrrolidine-3-yl)-7H-pyrrolo[2,3-d]pyrimidine-4-amine was added to a 5-mL round-bottomed flask and then dissolved with 1.50 mL of dichloromethane (CH$_2$Cl$_2$). After 83.2 mg of 4-(trifluoromethyl)benzenesulfonyl chloride was added thereto, the reaction mixture was treated with 0.0590 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 99.2 mg of (R)—N-methyl-N-(1-((4-(trifluoromethyl)phenyl)sulfonyl)pyrrolidine-3-yl)-7H-pyrrolo[2,3-d]pyrimidine-4-amine was obtained with a yield of about 72.9%.

$^1$H NMR (400 MHz, CDCl$_3$) δ10.24 (s, 1H), 8.25 (s, 1H), 8.02 (d, J=8.0 Hz, 2H), 7.87 (d, J=8.0 Hz, 2H), 7.09 (dd, J=3.6, 2.4 Hz, 1H), 6.55 (dd, J=3.6, 2.4 Hz, 1H), 5.66-5.58 (m, 1H), 3.74-3.68 (m, 1H), 3.49 (dd, J=10.4, 8.4 Hz, 1H), 3.40 (dd, J=10.4, 6.8 Hz, 1H), 3.32 (s, 3H), 3.19-3.12 (m, 1H), 2.26-2.08 (m, 2H).

LRMS (ESI) calcd for (C$_{18}$H$_{18}$F$_3$N$_5$O$_2$S+H$^+$) 426.1, found 426.1.

Example 28. (R)—N-methyl-N-(1-(naphthalene-2-ylsulfonyl)pyrrolidine-3-yl)-7H-pyrrolo[2,3-d]pyrimidine-4-amine

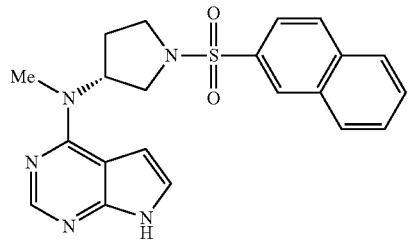 [SMILES: CN(c1ncnc2[nH]ccc12)[C@@H]1CCN(S(=O)(=O)c2ccc3ccccc3c2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 2.00 mL of dichloromethane (CH$_2$Cl$_2$). After 73.0 mg of 2-naphthalenesulfonyl chloride was added thereto, the reaction mixture was treated with 0.0590 mL of N,N-diisopropylethylamine and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 112 mg of (R)—N-methyl-N-(1-(naphthalene-2-ylsulfonyl)pyrrolidine-3-yl)-7H-pyrrolo[2,3-d]pyrimidine-4-amine was obtained with a yield of about 84.7%.

$^1$H NMR (400 MHz, CDCl$_3$) δ9.51 (s, 1H), 8.45 (s, 1H), 8.19 (s, 1H), 8.04-7.97 (m, 3H), 7.90 (dd, J=8.4, 1.6 Hz, 1H), 7.73-7.53 (m, 2H), 7.00-6.99 (m, 1H), 6.49-6.48 (m, 1H), 5.59-5.50 (m, 1H), 3.74-3.71 (m, 1H), 3.53-3.49 (m, 1H), 3.44-3.40 (m, 1H), 3.28 (s, 3H), 3.22-3.11 (m, 1H), 2.21-2.11 (m, 2H).

LRMS (ESI) calcd for (C$_{21}$H$_{21}$N$_5$O$_2$S+H$^+$) 408.2, found 408.1.

Example 29. (R)—N-methyl-N-(1-(piperidine-1-ylsulfonyl)pyrrolidine-3-yl)-7H-pyrrolo[2,3-d]pyrimidine-4-amine

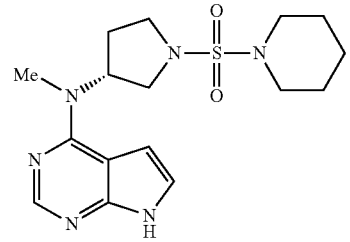 [SMILES: CN(c1ncnc2[nH]ccc12)[C@@H]1CCN(S(=O)(=O)N2CCCCC2)C1]

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0450 mL of piperidine-1-sulfonyl chloride was added thereto, the reaction mixture was treated with 0.0590 mL of N,N-diisopropylethylamine and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 91.0 mg of (R)—N-methyl-N-(1-(piperidine-1-ylsulfonyl)pyrrolidine-3-yl)-7H-pyrrolo[2,3-d]pyrimidine-4-amine was obtained with a yield of about 77.8%.

$^1$H NMR (400 MHz, CDCl$_3$) δ10.57 (s, 1H), 8.34 (s, 1H), 7.02 (s, 1H), 6.61 (s, 1H), 5.87-5.81 (m, 1H), 3.65-3.59 (m, 2H), 3.40-3.33 (m, 5H), 3.31-3.27 (m, 4H), 2.33-2.10 (m, 2H), 1.69-1.58 (m, 6H).

LRMS (ESI) calcd for (C$_{16}$H$_{24}$N$_6$O$_2$S+H$^+$) 365.2, found 365.2.

Example 30. (R)—N-methyl-N-(1-(morpholinosulfonyl)pyrrolidine-3-yl)-7H-pyrrolo[2,3-d]pyrimidine-4-amine

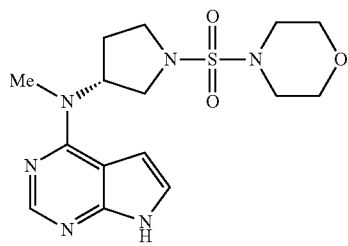 [SMILES: CN(c1ncnc2[nH]ccc12)[C@@H]1CCN(S(=O)(=O)N2CCOCC2)C1]

10.0 mL of dichloromethane (CH$_2$Cl$_2$) was added to a 50-mL round-bottomed flask, which was then cooled down in an ice bath (low-temperature bath). After 0.300 mL of sulfuryl chloride (SO$_2$Cl$_2$) was added thereto, a solution of 213 mg of morpholine dissolved in 3.0 mL of dichloromethane (CH$_2$Cl$_2$) was slowly added while cooling in the ice bath (low-temperature bath). The reaction mixture was treated with 520 mg of trimethylamine and then stirred for about 2 hours. The resulting reaction product was dissolved with 20.0 mL of chloroform and then washed with 20.0 mL of ice water. The chloroform phase was separated, dried with magnesium sulfate (MgSO$_4$), and then filtered. The resulting filtrate was distilled under reduced pressure. As a result, 160 mg of morpholine-4-sulfonyl chloride was obtained with a yield of about 23.3%.

70.0 mg of (R)—N-methyl-N-(pyrrolidine-3-yl)-7H-pyrrolo[2,3-d]pyrimidine-4-amine was added to a 5-mL round-bottomed flask and then dissolved with 1.00 mL of dichloromethane (CH$_2$Cl$_2$). After 0.0390 mL of morpholine-4-sulfonyl chloride was added thereto, the reaction mixture was treated with 0.0590 mL of N,N-diisopropylethylamine and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 47.0 mg of (R)—N-methyl-N-(1-(morpholinosulfonyl)pyrrolidine-3-yl)-7H-pyrrolo[2,3-d]pyrimidine-4-amine was obtained with a yield of about 40.2%.

$^1$H NMR (400 MHz, CDCl$_3$) δ10.06 (s, 1H), 8.39 (s, 1H), 7.11-7.10 (m, 1H), 6.62-6.61 (m, 1H), 5.84-5.76 (m, 1H), 3.78-3.77 (m, 4H), 3.70-3.64 (m, 2H), 3.45-3.29 (m, 9H), 2.36-2.17 (m, 2H).

LRMS (ESI) calcd for (C$_{15}$H$_{22}$N$_6$O$_3$S+H$^+$) 367.2, found 367.1.

Example 31. (S)-3-(3-(methyl(7H-pyrrolo[2,3-d]pyrimidine-4-yl)amino)pyrrolidine-1-yl)-3-oxopropanenitrile

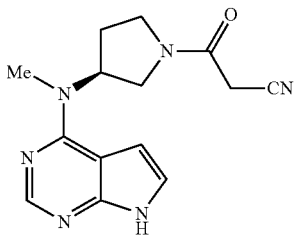 [SMILES: CN(c1ncnc2[nH]ccc12)[C@H]1CCN(C(=O)CC#N)C1]

720 mg of tert-butyl (S)-(1-benzylpyrrolidine-3-yl)carbamate was added to a 100-mL round-bottomed flask. After 11.5 mL of tetrahydrofuran and 623 mg of lithium aluminum hydride (LiAlH$_4$) were sequentially added thereto, the reaction mixture was refluxed for about 4 hours and then cooled at 0° C. 1.16 mL of deionized water was slowly added to the reaction mixture while cooling. After the reaction mixture was stirred for about 5 minutes, 1.16 mL of a 15% sodium hydroxide (NaOH) aqueous solution was added thereto. The reaction mixture was further stirred for about 5 minutes, and then 3.80 mL of deionized water was added thereto to terminate the reaction. The reaction mixture was filtered through a Celite™ 545 filter agent. The resulting filtrate was distilled under reduced pressure, and then the resulting residue was purified by flash column chromatography (MeOH:CH$_2$Cl$_2$:NH$_4$OH=5:90:5). As a result, 440 mg of (S)-1-benzyl-N-methylpyrrolidine-3-amine was obtained with a yield of about 89.9%.

440 mg of (S)-1-benzyl-N-methylpyrrolidine-3-amine was added to a 25-mL round-bottomed flask, and then 9.00 mL of deionized water and 373 mg of 6-chloro-7-deazapurine were sequentially added thereto. After 639 mg of potassium carbonate (K$_2$CO$_3$) was added to the reaction mixture, the reaction mixture was refluxed for about 36 hours and then cooled at room temperature. The reaction mixture was extracted three times with 40.0 mL of dichloromethane (CH$_2$Cl$_2$) to collect an organic phase. The collected organic phase was concentrated under reduced pressure, and the resulting residue was purified by flash column chromatography (MeOH:CH$_2$Cl$_2$=2:98). As a result, 544 mg of (S)—N-(1-benzylpyrrolidine-3-yl)-N-methyl-7H-pyrrolo[2,3-d]pyrimidine-4-amine was obtained with a yield of about 76.6%.

534 mg of (S)—N-(1-benzylpyrrolidine-3-yl)-N-methyl-7H-pyrrolo[2,3-d]pyrimidine-4-amine was added to a 25-mL round-bottomed flask and then dissolved with 5.00 mL of methanol. After 534 mg of a 10 w/w % palladium/carbon (Pd/C) was added thereto, a hydrogen-containing balloon was installed on the reaction flask. The reaction mixture was vigorously stirred overnight and then filtered through a Celite™ 545 filter agent. The resulting filtrate was concentrated under reduced pressure, and then the resulting residue was purified by flash column chromatography (MeOH:CH$_2$Cl$_2$=2:98). The resulting fraction was concentrated under reduced pressure and then further under vacuum. As a result, 250 mg of (S)—N-methyl-N-(pyrrolidine-3-yl)-7H-pyrrolo[2,3-d]pyrimidine-4-amine was obtained with a yield of about 66.1%.

150 mg of (S)—N-methyl-N-(pyrrolidine-3-yl)-7H-pyrrolo[2,3-d]pyrimidine-4-amine was added to a 5-mL round-bottomed flask and then dissolved with 2.25 mL of n-butanol. After 0.0730 mL of ethyl cyanoacetate was added thereinto, the reaction mixture was treated with 0.0520 mL of 1,8-diazabicyclo[5.4.0]undec-7-ene (DBU), and then heated at about 80° C. for about 24 hours. After termination of the reaction, the reaction solution was distilled under reduced pressure to remove the solvent. The resulting residue was purified by flash column chromatography (MeOH:CH$_2$Cl$_2$=2:98). The resulting fraction was concentrated under reduced pressure and then further under vacuum. As a result, 140 mg of (S)-3-(3-(methyl(7H-pyrrolo[2,3-d]pyrimidine-4-yl)amino)pyrrolidine-1-yl)-3-oxopropanenitrile was obtained with a yield of about 71.4%.

$^1$H NMR (400 MHz, CDCl$_3$) δ10.39 (s, 1H), 8.33 (s, 1H), 7.12 (d, J=2.6 Hz, 1H), 6.60 (s, 1H), 5.89-5.56 (m, 1H), 3.96-3.72 (m, 2H), 3.69-3.49 (m, 2H), 3.46 (t, J=5.4 Hz, 2H), 3.35 (d, J=14.9 Hz, 3H), 2.40-2.13 (m, 2H).

LRMS (ESI) calcd for (C$_{14}$H$_{16}$N$_6$O+H$^+$) 285.2, found 285.1.

Example 32. (R)-3-((3-((7H-pyrrolo[2,3-d]pyrimidine-4-yl)amino)pyrrolidine-1-yl)sulfonyl)benzonitrile

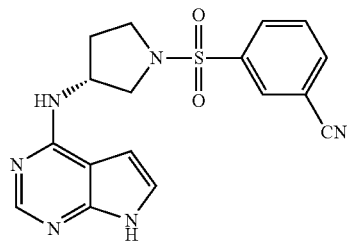 [SMILES: N#Cc1cccc(S(=O)(=O)N2CC[C@@H](Nc3ncnc4[nH]ccc34)C2)c1]

300 mg of (3R)-(+)-1-benzyl-3-aminopyrrolidine was added to a 25-mL round-bottomed flask. After 6.00 mL of deionized water and 274 mg of 6-chloro-7-deazapurine were sequentially added thereto, 470 mg of potassium carbonate (K$_2$CO$_3$) was added to the reaction mixture, and then the reaction mixture was refluxed for about 24 hours and then cooled at room temperature. The reaction mixture was extracted three times with 10.0 mL of dichloromethane (CH$_2$Cl$_2$) to collect an organic phase. The collected organic phase was concentrated under reduced pressure, and the resulting residue was purified by flash column chromatography (MeOH:CH$_2$Cl$_2$=2:98). As a result, 292 mg of (R)—N-(1-benzylpyrrolidine-3-yl)-7H-pyrrolo[2,3-d]pyrimidine-4-amine was obtained with a yield of about 58.5%.

294 mg of (R)—N-(1-benzylpyrrolidine-3-yl)-7H-pyrrolo[2,3-d]pyrimidine-4-amine was added to a 25-mL round-bottomed flask and then dissolved with 4.00 mL of methanol. After 280 mg of a 10 w/w % palladium/carbon (Pd/C) was added thereto, a hydrogen-containing balloon was installed on the reaction flask. The reaction mixture was vigorously stirred overnight and then filtered through a Celite™ 545 filter agent. The resulting filtrate was concentrated under reduced pressure, and then the resulting residue was purified by flash column chromatography (MeOH:CH$_2$Cl$_2$=2:98). The resulting fraction was concentrated under reduced pressure and then further under vacuum. As a result, 191 mg of (R)—N-(pyrrolidine-3-yl)-7H-pyrrolo[2,3-d]pyrimidine-4-amine was obtained with a yield of about 94.8%.

60.0 mg of (R)—N-(pyrrolidine-3-yl)-7H-pyrrolo[2,3-d]pyrimidine-4-amine was added to a 25-mL round-bottomed flask and then dissolved with 1.50 mL of dichloromethane (CH$_2$Cl$_2$). After 59.6 mg of 3-cyanobenzenesulfonyl chloride was added to the solution, the reaction mixture was treated with 0.0770 mL of N,N-diisopropylethylamine. The reaction mixture was then stirred overnight at room temperature and then concentrated under reduced pressure, and then the resulting residue was purified by flash column chromatography (MeOH:CH$_2$Cl$_2$=2:98). The resulting fraction was concentrated under reduced pressure and then further under vacuum. As a result, 42.0 mg of (R)-3-((3-((7H-pyrrolo[2,3-d]pyrimidine-4-yl)amino)pyrrolidine-1-yl)sulfonyl)benzonitrile was obtained with a yield of about 38.2%.

$^1$H NMR (400 MHz, DMSO) δ11.51 (s, 1H), 8.18 (s, 1H), 8.08 (s, 1H), 8.03 (d, J=8.0 Hz, 1H), 7.98 (d, J=7.6 Hz, 1H), 7.65 (t, J=8.0 Hz, 1H), 7.18 (d, J=5.6 Hz, 1H), 7.06 (s, 1H), 6.40 (d, J=1.2 Hz, 1H), 4.43-4.39 (m, 1H), 3.53-3.47 (m, 2H), 3.39-3.26 (m, 2H), 2.14-2.05 (m, 1H), 1.96-1.88 (m, 1H).

LRMS (ESI) calcd for (C$_{17}$H$_{16}$N$_6$O$_2$S+H$^+$) 369.1, found 369.1.

Example 33. (R)-3-(3-(ethyl(7H-pyrrolo[2,3-d]pyrimidine-4-yl)amino)pyrrolidine-1-yl)-3-oxopropanenitrile

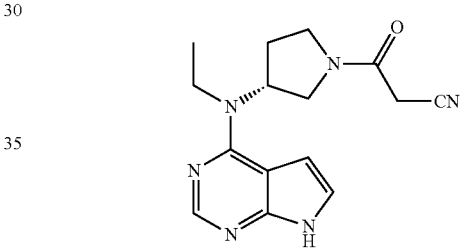

2.00 g of (R)-1-benzylpyrrolidine-3-amine was added to a 50-mL round-bottomed flask and then dissolved with 14.7 mL of dichloromethane (CH$_2$Cl$_2$). 1.07 mL of acetic anhydride was added into the solution and then stirred overnight at room temperature. The resulting fraction was concentrated under reduced pressure without purification and then further under vacuum. As a result, 2.12 g of (R)—N-(1-benzylpyrrolidine-3-yl)acetamide was obtained with a yield of about 85.0%.

2.11 g of (R)—N-(1-benzylpyrrolidine-3-yl)acetamide was added to a 100-mL round-bottomed flask. After 47.6 mL of tetrahydrofuran and 1.61 g of lithium aluminum hydride (LiAlH$_4$) were sequentially added thereto, the reaction mixture was refluxed overnight, and then cooled at 0° C. 2.00 mL of deionized water was slowly added to the reaction mixture while cooling. After the reaction mixture was stirred for about 5 minutes, 1.50 mL of a 15% sodium hydroxide (NaOH) aqueous solution was added thereto. The reaction mixture was further stirred for about 5 minutes, and then 3.80 mL of deionized water was added thereto to terminate the reaction. The reaction mixture was filtered through a Celite™ 545 filter agent. The resulting filtrate was distilled under reduced pressure. As a result, 1.85 g of (R)-1-benzyl-N-ethylpyrrolidine-3-amine was obtained with a yield of about 94.0%.

1.85 g of (R)-1-benzyl-N-ethylpyrrolidine-3-amine was added to a 100-mL round-bottomed flask, and then 46.0 mL of deionized water and 1.46 g of 6-chloro-7-deazapurine were sequentially added thereto. After 1.56 g of potassium carbonate ($K_2CO_3$) was added to the reaction mixture, the reaction mixture was refluxed for about 18 hours and then cooled at room temperature. The reaction mixture was extracted three times with 10.0 mL of dichloromethane ($CH_2Cl_2$) to collect an organic phase. The collected organic phase was concentrated under reduced pressure, and the resulting residue was purified by flash column chromatography (MeOH:$CH_2Cl_2$=0:100→1:80→1:50). As a result, 296 mg of (R)—N-(1-benzylpyrrolidine-3-yl)-N-ethyl-7H-pyrrolo[2,3-d]pyrimidine-4-amine was obtained with a yield of about 10.0%.

296 mg of (R)—N-(1-benzylpyrrolidine-3-yl)-N-ethyl-7H-pyrrolo[2,3-d]pyrimidine-4-amine was added to a 25-mL round-bottomed flask and then dissolved with 9.20 mL of methanol. After 330 mg of a 10 w/w % palladium/carbon (Pd/C) was added thereto, a hydrogen-containing balloon was installed on the reaction flask. The reaction mixture was vigorously stirred overnight and then filtered through a Celite™ 545 filter agent. The resulting filtrate was concentrated under reduced pressure and then further under vacuum. As a result, 189 mg of (R)—N-ethyl-N-(pyrrolidine-3-yl)-7H-pyrrolo[2,3-d]pyrimidine-4-amine was obtained with a yield of about 88.8%.

117 mg of (R)—N-ethyl-N-(pyrrolidine-3-yl)-7H-pyrrolo[2,3-d]pyrimidine-4-amine was added to a 5-mL round-bottomed flask and then dissolved with 2.10 mL of dichloromethane ($CH_2Cl_2$). After 0.0610 mL of chloroacetyl chloride was added to the solution, the reaction mixture was treated with 0.223 mL of N,N-diisopropylethylamine and then stirred at room temperature for about 1 hour. The reaction mixture was concentrated under reduced pressure, and then the resulting residue was purified by flash column chromatography (MeOH:$CH_2Cl_2$=0:100→1:80→1:50). The resulting fraction was concentrated under reduced pressure and then further under vacuum. As a result, 96.0 mg of (R)-2-chloro-1-(3-(ethyl(7H-pyrrolo[2,3-d]pyrimidine-4-yl)amino)pyrrolidine-1-yl)ethane-1-one was obtained with a yield of about 61.0%.

96.0 mg of (R)-2-chloro-1-(3-(ethyl(7H-pyrrolo[2,3-d]pyrimidine-4-yl)amino)pyrrolidine-1-yl)ethane-1-one was added into a 5-mL round-bottomed flask and then dissolved with 2.00 mL of N,N-dimethylformamide. 40.4 mg of potassium cyanide was added to the solution, and the reaction mixture was stirred at about 30° C. to about 40° C. for about 1 hour. After the reaction mixture was concentrated under reduced pressure, 10.0 mL of deionized water and 10.0 mL of dichloromethane ($CH_2Cl_2$) were added into the resulting residue and then stirred for about 5 minutes to separate an organic phase. The organic phase was concentrated under reduced pressure, and then the resulting residue was purified by flash column chromatography (MeOH:$CH_2Cl_2$=0:100→1:80→1:50). The resulting fraction was concentrated under reduced pressure and then further under vacuum. As a result, 50.9 mg of (R)-3-(3-(ethyl(7H-pyrrolo[2,3-d]pyrimidine-4-yl)amino)pyrrolidine-1-yl)-3-oxopropanenitrile was obtained with a yield of about 55.0%.

$^1$H NMR (400 MHz, $CDCl_3$) δ10.47 (s, 1H), 8.34 (s, 1H), 7.15 (d, J=4.0 Hz, 1H), 6.53 (d, J=3.2 Hz, 1H), 5.55-5.53 (m, 1H), 4.05-3.90 (m, 2H), 3.83-3.63 (m, 2H), 3.55-3.44 (m, 3H), 2.42-2.27 (m, 3H), 1.42 (q, J=6.8 Hz, 3H).

LRMS (ESI) calcd for ($C_{15}H_{18}N_6O$+$H^+$) 299.2, found 299.1.

Example 34. (R)-3-((3-(ethyl(7H-pyrrolo[2,3-d]pyrimidine-4-yl)amino)pyrrolidine-1-yl)sulfonyl)benzonitrile

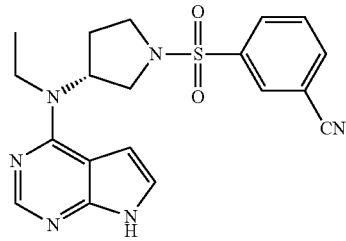 [SMILES: CCN(c1ncnc2[nH]ccc12)[C@@H]1CCN(S(=O)(=O)c2cccc(C#N)c2)C1]

67.0 mg of (R)—N-ethyl-N-(pyrrolidine-3-yl)-7H-pyrrolo[2,3-d]pyrimidine-4-amine was added to a 5-mL round-bottomed flask and then dissolved with 1.45 mL of dichloromethane ($CH_2Cl_2$). After 60.5 mg of 3-cyanobenzenesulfonyl chloride was added to the solution, the reaction mixture was treated with 0.0500 mL of N,N-diisopropylethylamine and then stirred at room temperature for about 1 hour. The reaction mixture was concentrated under reduced pressure, and then the resulting residue was purified by flash column chromatography (MeOH:$CH_2Cl_2$=0:100→1:80→1:50). The resulting fraction was concentrated under reduced pressure and then further under vacuum. As a result, 84.3 mg of (R)-3-((3-(ethyl(7H-pyrrolo[2,3-d]pyrimidine-4-yl)amino)pyrrolidine-1-yl)sulfonyl)benzonitrile was obtained with a yield of about 73.3%.

$^1$H NMR (400 MHz, $CDCl_3$) δ10.34 (s, 1H), 8.20 (s, 1H), 8.12 (d, J=10.0 Hz, 2H), 7.94 (d, J=7.6 Hz, 1H), 7.11 (d, J=3.6 Hz, 1H), 6.45 (d, J=3.6 Hz, 1H), 5.32-5.24 (m, 1H), 3.81-3.63 (m, 4H), 3.38-3.27 (m, 2H), 3.27-2.19 (m, 3H), 1.37 (t, J=7.2 Hz, 3H).

LRMS (ESI) calcd for ($C_{19}H_{20}N_6O_2S$+$H^+$) 397.1, found 397.1.

Example 35. (R)-3-(3-((cyclopropylmethyl)(7H-pyrrolo[2,3-d]pyrimidine-4-yl)amino)pyrrolidine-1-yl)-3-oxopropanenitrile

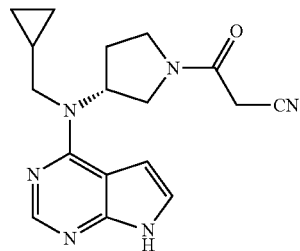 [SMILES: N#CCC(=O)N1CC[C@@H](N(CC2CC2)c2ncnc3[nH]ccc23)C1]

2.00 g of (R)-1-benzylpyrrolidine-3-amine was added to a 100-mL round-bottomed flask and then dissolved with 54.0 mL of dichloromethane ($CH_2Cl_2$). 0.890 mL of cyclopropanecarbonyl chloride was added into the solution and then stirred at room temperature for about 1 hour. The resulting fraction was concentrated under reduced pressure without purification and then further under vacuum. As a result, 3.02 g of (R)—N-(1-benzylpyrrolidine-3-yl)cyclopropane carboxamide was obtained in a quantitative yield.

2.77 g of (R)—N-(1-benzylpyrrolidine-3-yl)cyclopropane carboxamide was added to a 100-mL round-bottomed flask, and 57.0 mL of tetrahydrofuran was added thereto. After 1.90 g of lithium aluminum hydride (LiAlH$_4$) was added thereto, the reaction mixture was refluxed overnight and then cooled at 0° C. 10.0 mL of deionized water was slowly added thereto while cooling. After the reaction mixture was stirred for about 5 minutes, 2.00 mL of a 15% sodium hydroxide (NaOH) aqueous solution was added thereto. The reaction mixture was further stirred for about 5 minutes, and then 10.0 mL of deionized water was added thereto to terminate the reaction. The reaction mixture was filtered through a Celite™ 545 filter agent. The resulting filtrate was distilled under reduced pressure. As a result, 1.68 g of (R)-1-benzyl-N-(cyclopropylmethyl)pyrrolidine-3-amine was obtained with a yield of about 64.0%.

1.68 g of (R)-1-benzyl-N-(cyclopropylmethyl)pyrrolidine-3-amine was added into a 100-mL round-bottomed flask, and 40.0 mL of deionized water was added thereto. After 1.17 g of 6-chloro-7-deazapurine and 1.26 g of potassium carbonate (K$_2$CO$_3$) were added into the reaction mixture, the reaction mixture was refluxed for about 18 hours and then cooled at room temperature. The reaction mixture was then extracted three times with 40.0 mL of dichloromethane (CH$_2$Cl$_2$) to collect an organic phase. The collected organic phase was concentrated under reduced pressure. The resulting residue was purified by flash column chromatography (MeOH:CH$_2$Cl$_2$=0:100→1:80→1:50). As a result, 313 mg of (R)—N-(1-benzylpyrrolidine-3-yl)-N-(cyclopropylmethyl)-7H-pyrrolo[2,3-d]pyrimidine-4-amine was obtained with a yield of about 12.4%.

310 mg of (R)—N-(1-benzylpyrrolidine-3-yl)-N-(cyclopropylmethyl)-7H-pyrrolo[2,3-d]pyrimidine-4-amine was added to a 25-mL round-bottomed flask and then dissolved with 8.90 mL of methanol. After 310 mg of a 10 w/w % palladium/carbon (Pd/C) was added thereto, a hydrogen-containing balloon was installed on the reaction flask. The reaction mixture was vigorously stirred overnight and then filtered through a Celite™ 545 filter agent. The resulting filtrate was concentrated under reduced pressure and then further under vacuum. As a result, 162 mg of (R)—N-(cyclopropylmethyl)-N-(pyrrolidine-3-yl)-7H-pyrrolo[2,3-d]pyrimidine-4-amine was obtained with a yield of about 70.7%.

100 mg of (R)—N-(cyclopropylmethyl)-N-(pyrrolidine-3-yl)-7H-pyrrolo[2,3-d]pyrimidine-4-amine was added to a 5-mL round-bottomed flask and then dissolved with 1.60 mL of dichloromethane (CH$_2$Cl$_2$). After 0.0470 mL of chloroacetyl chloride was added into the solution, the reaction mixture was treated with 0.0170 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 72.6 mg of (R)-2-chloro-1-(3-((cyclopropylmethyl)(7H-pyrrolo[2,3-d]pyrimidine-4-yl)amino)pyrrolidine-1-yl)ethane-1-one was obtained with a yield of about 56.0%.

72.0 mg of (R)-2-chloro-1-(3-((cyclopropylmethyl)(7H-pyrrolo[2,3-d]pyrimidine-4-yl)amino)pyrrolidine-1-yl)ethane-1-one was added to a 5-mL round-bottomed flask and then dissolved with 1.50 mL of N,N-dimethylformamide. After 28.7 mg of potassium cyanide was added into the solution, the reaction mixture was stirred at about 30° C. to about 40° C. for about 1 hour. After the reaction mixture was concentrated under reduced pressure, 10.0 mL of deionized water and 10.0 mL of dichloromethane (CH$_2$Cl$_2$) were added into the resulting residue and then stirred for about 5 minutes to separate an organic phase. The organic phase was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 38.4 mg of (R)-3-(3-((cyclopropylmethyl)(7H-pyrrolo[2,3-d]pyrimidine-4-yl)amino)pyrrolidine-1-yl)-3-oxopropanenitrile was obtained with a yield of about 54.0%.

$^1$H NMR (400 MHz, CDCl$_3$) δ10.15 (s, 1H), 8.35 (s, 1H), 7.15 (t, J=3.6 Hz, 1H), 6.71 (dd, J=5.6, 3.6 Hz, 1H), 5.37-5.30 (m, 1H), 4.05-3.94 (m, 2H), 3.69-3.53 (m, 4H), 3.48 (d, J=14.4 Hz, 2H), 2.50-2.30 (m, 2H), 1.23-1.16 (m, 1H), 0.73 (t, J=6.8 Hz, 2H), 0.30 (t, J=4.8 Hz, 2H).

LRMS (ESI) calcd for (C$_{17}$H$_{20}$N$_6$O+H$^+$) 325.2, found 325.2.

Example 36. (R)-3-((3-((cyclopropylmethyl)(7H-pyrrolo[2,3-d]pyrimidine-4-yl)amino)pyrrolidine-1-yl)sulfonyl)benzonitrile

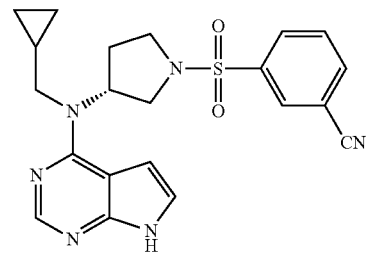 [SMILES: N#Cc1cccc(S(=O)(=O)N2CC[C@@H](N(CC3CC3)c3ncnc4[nH]ccc34)C2)c1]

62.0 mg of (R)—N-(cyclopropylmethyl)-N-(pyrrolidine-3-yl)-7H-pyrrolo[2,3-d]pyrimidine-4-amine was added to a 5-mL round-bottomed flask and then dissolved with 1.20 mL of dichloromethane (CH$_2$Cl$_2$). After 50.4 mg of 3-cyanobenzenesulfonyl chloride was added to the solution, the reaction mixture was treated with 0.0420 mL of N,N-diisopropylethylamine and then stirred at room temperature for about 1 hour. The reaction mixture was concentrated under reduced pressure, and then the resulting residue was purified by flash column chromatography (MeOH:CH$_2$Cl$_2$=0:100→1:80→1:50). The resulting fraction was concentrated under reduced pressure and then further under vacuum. As a result, 62.2 mg of (R)-3-((3-((cyclopropylmethyl)(7H-pyrrolo[2,3-d]pyrimidine-4-yl)amino)pyrrolidine-1-yl)sulfonyl)benzonitrile was obtained with a yield of about 61.0%.

$^1$H NMR (400 MHz, CDCl$_3$) δ10.08 (s, 1H), 8.20 (s, 1H), 8.12 (d, J=8.0 Hz, 1H), 8.04 (s, 1H), 7.94 (d, J=7.6 Hz, 1H), 7.75 (t, J=7.6 Hz, 1H), 7.11 (d, J=4.0 Hz, 1H), 6.64 (d, J=3.6 Hz, 1H), 5.10-5.06 (m, 1H), 3.72-3.61 (m, 4H), 3.52-3.48 (m, 1H), 3.34-3.28 (m, 1H), 2.31-2.25 (m, 2H), 1.17-1.10 (m, 1H), 0.71-0.67 (m, 2H), 0.38-0.35 (m, 2H).

LRMS (ESI) calcd for (C$_{21}$H$_{22}$N$_6$O$_2$S+H$^+$) 423.2, found 423.1.

Example 37. 3-(4-(methyl(7H-pyrrolo[2,3-d]pyrimidine-4-yl)amino)piperidine-1-yl)-3-oxopropanenitrile

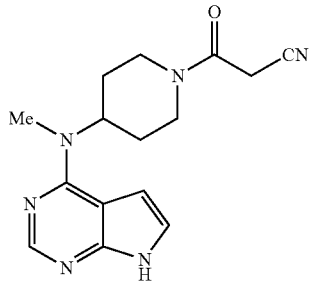 [SMILES: CN(c1ncnc2[nH]ccc12)C1CCN(C(=O)CC#N)CC1]

2.00 g of 4-amino-1-benzylpiperidine was added to a 100-mL round-bottomed flask, and then 20.0 mL of deionized water and 20.0 mL of saturated sodium hydrogen carbonate (NaHCO$_3$) were added thereto. After 2.41 g of di-tert-butyl dicarbonate (Boc$_2$O) was added thereto, the reaction mixture was vigorously stirred for about 4 hours and then concentrated under reduced pressure. The aqueous phase was extracted with 20.0 mL of ethyl acetate (EtOAc) obtain an organic phase. The organic phase was washed with 15.0 mL of deionized water and 5.00 mL of saturated brine. The organic phase was filtered with sodium sulfate (Na$_2$SO$_4$). The resulting filtrate was distilled under reduced pressure. As a result, 3.04 g of tert-butyl (1-benzylpiperidine-4-yl)carbamate was obtained with a yield of about 99.7%.

3.04 g of tert-butyl (1-benzylpiperidine-4-yl)carbamate was added to a 100-mL round-bottomed flask, and then 45.0 mL of tetrahydrofuran was added thereto. After 2.50 g of lithium aluminum hydride (LiAlH$_4$) was added thereto, the reaction mixture was refluxed for about 4 hour and then cooled at room temperature. 4.50 mL of deionized water was slowly added thereto while cooling. After the reaction mixture was stirred for about 5 minutes, 4.50 mL of a 15% sodium hydroxide (NaOH) aqueous solution was added thereto. The reaction mixture was further stirred for about 5 minutes, and then 13.5 mL of deionized water was added thereto to terminate the reaction. The reaction mixture was filtered through a Celite™ 545 filter agent. The resulting filtrate was distilled under reduced pressure. As a result, 2.22 g of 1-benzyl-N-methylpiperidine-4-amine was obtained with a quantitative yield.

1.00 g of 1-benzyl-N-methylpiperidine-4-amine was added to a 50-mL round-bottomed flask, and then 20.0 mL of deionized water was added thereto. After 790 mg of 6-chloro-7-deazapurine was added thereto, 1.35 g of potassium carbonate (K$_2$CO$_3$) was added into the reaction mixture. The reaction mixture was refluxed for about 24 hours and then cooled at room temperature. The reaction mixture was then extracted three times with 10.0 mL of dichloromethane (CH$_2$Cl$_2$) to collect an organic phase. The collected organic phase was concentrated under reduced pressure, and then the resulting residue was purified by flash column chromatography (MeOH:CH$_2$Cl$_2$=2:98). As a result, 607 mg of N-(1-benzylpiperidine-4-yl)-N-methyl-7H-pyrrolo[2,3-d]pyrimidine-4-amine was obtained with a yield of about 38.7%.

350 mg of N-(1-benzylpiperidine-4-yl)-N-methyl-7H-pyrrolo[2,3-d]pyrimidine-4-amine was added to a 50-mL round-bottomed flask, and then dissolved with 7.00 mL of methanol and 1.00 mL of dichloromethane (CH$_2$Cl$_2$). After 350 mg of a 10 w/w % palladium/carbon (Pd/C) was added thereto, a hydrogen-containing balloon was installed on the reaction flask. The reaction mixture was vigorously stirred for about 24 hours and then filtered through a Celite™ 545 filter agent. The resulting filtrate was concentrated under reduced pressure. The resulting fraction was concentrated under reduced pressure and then further under vacuum. As a result, 220 mg of N-methyl-N-(piperidine-4-yl)-7H-pyrrolo[2,3-d]pyrimidine-4-amine was obtained with a yield of about 87.7%.

150 mg of N-methyl-N-(piperidine-4-yl)-7H-pyrrolo[2,3-d]pyrimidine-4-amine was added to a 5-mL round-bottomed flask and then dissolved with 1.50 mL of n-butanol. After 0.690 mL of ethyl cyanoacetate was added into the solution, the reaction mixture was treated with 0.0485 mL of 1,8-diazabicyclo[5.4.0]undec-7-ene (DBU) and then heated at about 80° C. for about 24 hours. After termination of the reaction, the reaction solution was distilled under reduced pressure to remove the solvent. The resulting residue was purified by flash column chromatography (MeOH:CH$_2$Cl$_2$=2:98). The resulting fraction was concentrated under reduced pressure and then further under vacuum. As a result, 6.20 mg of 3-(4-(methyl(7H-pyrrolo[2,3-d]pyrimidine-4-yl)amino)piperidine-1-yl)-3-oxopropanenitrile was obtained with a yield of about 3.20%.

$^1$H NMR (400 MHz, DMSO) δ12.65 (s, 1H), 8.38 (s, 1H), 7.43 (s, 1H), 6.90 (d, J=1.6 Hz, 1H), 4.75 (s, 1H), 4.52 (d, J=12.8 Hz, 1H), 4.08 (s, 2H), 3.81 (d, J=13.6 Hz, 1H), 3.27-3.20 (m, 3H), 2.82-2.75 (m, 1H), 2.03-1.91 (m, 1H), 1.77 (s, 2H), 1.23-1.18 (m, 2H).

LRMS (ESI) calcd for (C$_{15}$H$_{18}$N$_6$O+H$^+$) 299.2, found 299.1.

Example 38. N-methyl-N-(1-(phenylsulfonyl)piperidine-4-yl)-7H-pyrrolo[2,3-d]pyrimidine-4-amine

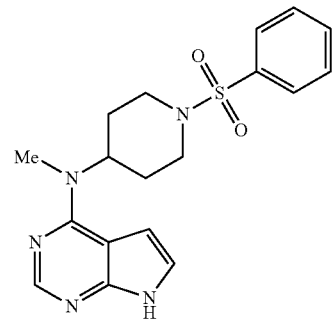 [SMILES: CN(c1ncnc2[nH]ccc12)C1CCN(S(=O)(=O)c2ccccc2)CC1]

70.0 mg of N-methyl-N-(piperidine-4-yl)-7H-pyrrolo[2,3-d]pyrimidine-4-amine was added to a 5-mL round-bottomed flask and then dissolved with 2.00 mL of dichloromethane (CH$_2$Cl$_2$). After 0.0400 mL of benzenesulfonyl chloride was added into the solution, the reaction mixture was treated with 0.0780 mL of N,N-diisopropylethylamine and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 50.0 mg of N-methyl-N-(1-(phenylsulfonyl)piperidine-4-yl)-7H-pyrrolo[2,3-d]pyrimidine-4-amine was obtained with a yield of about 45.5%.

$^1$H NMR (400 MHz, CDCl$_3$) δ 9.97 (s, 1H), 8.20 (s, 1H), 7.81 (d, J=7.2 Hz, 2H), 7.66 (t, J=7.2 Hz, 1H), 7.59 (t, J=7.2 Hz, 2H), 7.03 (d, J=3.6 Hz, 1H), 6.55 (d, J=7.2 Hz, 1H), 4.91-4.85 (m, 1H), 3.99 (d, J=12 Hz, 2H), 3.26 (s, 3H), 2.50-5.45 (m, 2H), 2.04-1.82 (m, 4H).

LRMS (ESI) calcd for (C$_{18}$H$_{21}$N$_5$O$_2$S+H$^+$) 372.2, found 372.1.

Example 39. 3-((4-(methyl(7H-pyrrolo[2,3-d]pyrimidine-4-yl)amino)piperidine-1-yl)sulfonyl)benzonitrile

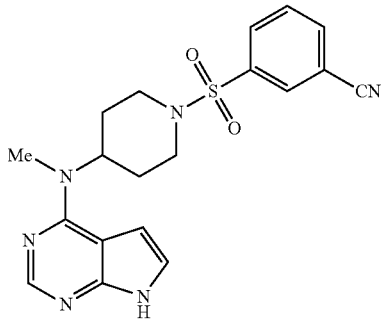 [SMILES: CN(c1ncnc2[nH]ccc12)C1CCN(S(=O)(=O)c2cccc(C#N)c2)CC1]

70.0 mg of N-methyl-N-(piperidine-4-yl)-7H-pyrrolo[2,3-d]pyrimidine-4-amine was added to a 5-mL round-bottomed flask and then dissolved with 1.50 mL of dichloromethane (CH$_2$Cl$_2$). After 61.0 mg of 3-cyanobenzenesulfonyl chloride was added into the solution, the reaction mixture was treated with 0.0790 mL of N,N-diisopropylethylamine and then stirred overnight at room temperature. The reaction mixture was concentrated under reduced pressure, and then the resulting residue was purified by flash column chromatography (MeOH:CH$_2$Cl$_2$=2:98). The resulting fraction was concentrated under reduced pressure and then further under vacuum. As a result, 23.1 mg of 3-((4-(methyl(7H-pyrrolo[2,3-d]pyrimidine-4-yl)amino)piperidine-1-yl)sulfonyl)benzonitrile was obtained with a yield of about 19.6%.

$^1$H NMR (400 MHz, CDCl$_3$) δ 8.22 (s, 1H), 8.10 (t, J=1.2 Hz, 1H), 8.05-8.02 (m, 1H), 7.95-7.92 (m, 1H), 7.76 (t, J=8.0 Hz, 1H), 7.11 (d, J=3.6 Hz, 1H), 6.62 (d, J=3.6 Hz, 1H), 5.00-4.97 (m, 1H), 4.05-4.02 (m, 3H), 3.34 (s, 2H), 2.58-2.50 (m, 3H), 2.08-1.97 (m, 2H), 1.93 (d, J=12.0 Hz, 2H).

LRMS (ESI) calcd for (C$_{19}$H$_{20}$N$_6$O$_2$S+H$^+$) 397.1, found 397.1.

Example 40. (R)-3-(3-(methyl(7H-pyrrolo[2,3-d]pyrimidine-4-yl)amino)piperidine-1-yl)-3-oxopropanenitrile

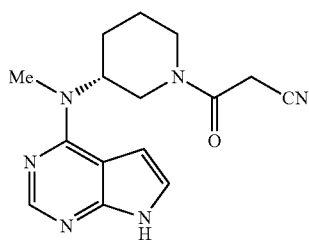 [SMILES: CN(c1ncnc2[nH]ccc12)[C@@H]1CCCN(C(=O)CC#N)C1]

500 mg of (R)-3-amino-1-benzylpiperidine was added to a 100-mL round-bottomed flask, and then 5.00 mL of deionized water and 5.00 mL of saturated sodium hydrogen carbonate (NaHCO$_3$) were added thereto. After 602 mg of di-tert-butyl dicarbamate (Boc$_2$O) was added thereto, the reaction mixture was vigorously stirred for about 4 hours and then concentrated under reduced pressure. An aqueous phase was extracted with 20.0 mL of ethyl acetate (EtOAc) to obtain an organic phase. The organic phase was washed with 10.0 mL of deionized water and 15.0 mL of saturated brine. The organic phase was filtered with sodium sulfate (Na$_2$SO$_4$). The resulting filtrate was distilled under reduced pressure. As a result, 730 mg of tert-butyl (R)-(1-benzylpiperidine-3-yl)carbamate was obtained with a yield of about 95.7%.

730 mg of tert-butyl (R)-(1-benzylpiperidine-3-yl)carbamate was added to a 100-mL round-bottomed flask, and then 12.0 mL of tetrahydrofuran was added thereto. After 601 mg of lithium aluminum hydride (LiAlH$_4$) was added thereto, the reaction mixture was refluxed for about 4 hours and then cooled at room temperature. 1.5 mL of deionized water was slowly added thereto while cooling. After the reaction mixture was stirred for about 5 minutes, 1.5 mL of a 15% sodium hydroxide (NaOH) aqueous solution was added thereto. The reaction mixture was further stirred for about 5 minutes, and then 2.0 mL of deionized water was added thereto to terminate the reaction. The reaction mixture was filtered through a Celite™ 545 filter agent. The resulting filtrate was distilled under reduced pressure. As a result, 580 mg of (R)-1-benzyl-N-methylpiperidine-3-amine was obtained with a quantitative yield.

580 mg of (R)-1-benzyl-N-methylpiperidine-3-amine was added to a 100-mL round-bottomed flask, and then 12.0 mL of deionized water was added thereto. After 458 mg of 6-chloro-7-deazapurine and 785 mg of potassium carbonate (K$_2$CO$_3$) were added into the reaction mixture, the reaction mixture was refluxed for about 24 hours and then collected at room temperature. The reaction mixture was extracted three times with 10.0 mL of dichloromethane (CH$_2$Cl$_2$) to collect an organic phase. The collected organic phase was concentrated under reduced pressure. The resulting residue was purified by flash column chromatography (MeOH:CH$_2$Cl$_2$=2:98). As a result, 440 mg of (R)—N-(1-benzylpiperidine-3-yl)-N-methyl-7H-pyrrolo[2,3-d]pyrimidine-4-amine was obtained with a yield of about 48.2%.

438 mg of (R)—N-(1-benzylpiperidine-3-yl)-N-methyl-7H-pyrrolo[2,3-d]pyrimidine-4-amine was added to a 50-mL round-bottomed flask and then dissolved with 5.00 mL of methanol. After 400 mg of a 10 w/w % palladium/carbon (Pd/C) was added thereto, a hydrogen-containing balloon was installed on the reaction flask. The reaction mixture was vigorously stirred for about 24 hours and then filtered through a Celite™ 545 filter agent. The resulting filtrate was concentrated under reduced pressure. The resulting fraction was concentrated under reduced pressure and then further under vacuum. As a result, 310 mg of (R)—N-methyl-N-(piperidine-3-yl)-7H-pyrrolo[2,3-d]pyrimidine-4-amine was obtained with a yield of about 98.4%.

90.0 mg of (R)—N-methyl-N-(piperidine-3-yl)-7H-pyrrolo[2,3-d]pyrimidine-4-amine was added to a 5-mL round-bottomed flask, and then dissolved with 1.70 mL of n-butanol. After 0.414 mL of ethyl cyanoacetate was added into the solution, the reaction mixture was treated with 0.0291 mL of 1,8-diazabicyclo[5.4.0]undec-7-ene (DBU) and then heated at about 80° C. for about 24 hours. After termination of the reaction, the reaction solution was distilled under reduced pressure to remove the solvent. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 42.0 mg of (R)-3-(3-(methyl(7H-pyrrolo[2,3-d]pyrimidine-4-yl)amino)piperidine-1-yl)-3-oxopropanenitrile was obtained with a yield of about 36.2%.

$^1$H NMR (400 MHz, $CDCl_3$) δ10.41 (d, J=84 Hz, 1H), 8.32 (s, 1H), 7.13-7.12 (m, 1H), 6.62-6.59 (m, 1H), 4.79-4.72 (m, 1H), 4.67 (d, J=11.2 Hz, 1H), 3.91-3.55 (m, 3H), 3.38 (s, 2H), 3.27 (s, 1H), 3.12 (q, J=11.2, 13.2 Hz, 1H), 2.65-2.58 (m, 1H), 2.11-2.08 (m, 1H), 2.02-1.69 (m, 3H).

LRMS (ESI) calcd for ($C_{15}H_{18}N_6O+H^+$) 299.2, found 299.1.

Example 41. (R)-3-((3-(methyl(7H-pyrrolo[2,3-d]pyrimidine-4-yl)amino)piperidine-1-yl)sulfonyl)benzonitrile

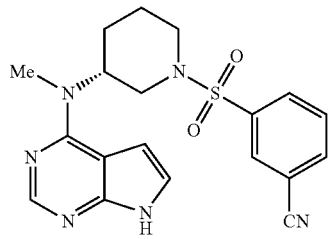 [SMILES: CN(c1ncnc2[nH]ccc12)[C@@H]1CCCN(S(=O)(=O)c2cccc(C#N)c2)C1]

70.0 mg of (R)—N-methyl-N-(piperidine-3-yl)-7H-pyrrolo[2,3-d]pyrimidine-4-amine was added to a 5-mL round-bottomed flask, and then dissolved with 1.50 mL of dichloromethane ($CH_2Cl_2$). After 64.0 mg of 3-cyanobenzenesulfonyl chloride was added to the solution, the reaction mixture was treated with 0.0790 mL of N,N-diisopropylethylamine and then stirred overnight at room temperature. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 70.0 mg of (R)-3-((3-(methyl(7H-pyrrolo[2,3-d]pyrimidine-4-yl)amino)piperidine-1-yl)sulfonyl)benzonitrile was obtained with a yield of about 59.3%.

$^1$H NMR (400 MHz, $CDCl_3$) δ9.81 (s, 1H), 8.36 (s, 1H), 8.15 (t, J=1.2 Hz, 1H), 8.10-8.08 (m, 1H), 7.93-7.91 (m, 1H), 7.74 (t, J=8.0 Hz, 1H), 7.11 (q, J=2.4, 3.6 Hz, 1H), 6.60 (q, J=1.6, 3.6 Hz, 1H), 4.95-4.90 (m, 1H), 4.06 (dd, J=4.4, 11.6 Hz, 1H), 3.94 (d, J=12 Hz, 1H), 3.24 (s, 3H), 2.52 (t, J=11.2 Hz, 1H), 2.46-2.40 (m, 1H), 2.00-1.94 (m, 1H), 1.93-1.91 (m, 1H), 1.84-1.73 (m, 1H), 1.71-1.67 (m, 1H).

LRMS (ESI) calcd for ($C_{19}H_{20}N_6O_2S+H^+$) 397.1, found 397.1.

Example 42. 3-(((3R,4R)-4-methyl-3-(methyl(7H-pyrrolo[2,3-d]pyrimidine-4-yl)amino)piperidine-1-yl)sulfonyl)benzonitrile

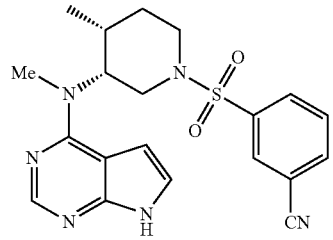 [SMILES: C[C@@H]1CCN(S(=O)(=O)c2cccc(C#N)c2)C[C@@H]1N(C)c1ncnc2[nH]ccc12]

500 mg of (3R,4R)-1-benzyl-N,4-dimethylpiperidine-3-amine dihydrochloride was added to a 25-mL round-bottomed flask, and 5.00 mL of deionized water was added thereto. After 277 mg of 6-chloro-7-deazapurine and 1.08 of potassium carbonate ($K_2CO_3$) were added into the reaction mixture, the reaction mixture was refluxed for about 24 hours and then cooled at room temperature. The reaction mixture was extracted three times with 10.0 mL of dichloromethane ($CH_2Cl_2$) to collect an organic phase. The collected organic phase was concentrated under reduced pressure. The resulting residue was purified by flash column chromatography (MeOH:$CH_2Cl_2$=2:98). As a result, 282 mg of N-((3R,4R)-1-benzyl-4-methylpiperidine-3-yl)-N-methyl-7H-pyrrolo[2,3-d]pyrimidine-4-amine was obtained with a yield of about 48.9%.

282 mg of N-((3R,4R)-1-benzyl-4-methylpiperidine-3-yl)-N-methyl-7H-pyrrolo[2,3-d]pyrimidine-4-amine was added to a 25-mL round-bottomed flask, and then dissolved with 3.00 mL of methanol. After 280 mg of a 10 w/w % palladium/carbon (Pd/C) was added thereto, a hydrogen-containing balloon was installed on the reaction flask. The reaction mixture was vigorously stirred for about 24 hours and then filtered through a Celite™ 545 filter agent. The resulting filtrate was concentrated under reduced pressure. The resulting fraction was concentrated under reduced pressure and then further under vacuum. As a result, 200 mg of N-methyl-N-((3R,4R)-4-methylpiperidine-3-yl)-7H-pyrrolo[2,3-d]pyrimidine-4-amine was obtained with a yield of about 97.1%.

70.0 mg of N-methyl-N-((3R,4R)-4-methylpiperidine-3-yl)-7H-pyrrolo[2,3-d]pyrimidine-4-amine was added to a 5-mL round-bottomed flask, and then dissolved with 1.50 mL of dichloromethane ($CH_2Cl_2$). After 57.0 mg of 3-cyanobenzenesulfonyl chloride was added into the solution, the reaction mixture was treated with 0.0750 mL of N,N-diisopropylethylamine and then stirred overnight at room temperature. The reaction mixture was concentrated under reduced pressure, and then the resulting residue was purified by flash column chromatography (MeOH:$CH_2Cl_2$=2:98). The resulting fraction was concentrated under reduced pressure and then further under vacuum. As a result, 85.9 mg of 3-(((3R,4R)-4-methyl-3-(methyl(7H-pyrrolo[2,3-d]pyrimidine-4-yl)amino)piperidine-1-yl)sulfonyl)benzonitrile was obtained with a yield of about 73.4%.

$^1$H NMR (400 MHz, $CDCl_3$) δ10.40 (s, 1H), 8.27 (s, 1H), 8.09-8.08 (m, 1H), 8.03-8.01 (m, 1H), 7.95-7.92 (m, 1H), 7.64 (t, J=3.6 Hz, 1H), 7.13 (d, J=3.6 Hz, 1H), 6.66 (d, J=3.6 Hz, 1H), 5.49 (d, J=4.8 Hz, 1H), 3.79 (dd, J=4.4, 12.4 Hz, 1H), 3.68 (s, 3H), 3.10 (dd, J=4.4, 12.4 Hz, 1H), 2.83-2.77 (m, 1H), 2.20-2.11 (m, 1H), 1.92-1.86 (m, 3H), 0.98 (d, J=6.8 Hz, 3H).

LRMS (ESI) calcd for ($C_{20}H_{22}N_6O_2S+H^+$) 411.2, found 411.1.

Example 43. (R)-3-(3,3-dimethyl-4-(methyl(7H-pyrrolo[2,3-d]pyrimidine-4-yl)amino)pyrrolidine-1-yl)-3-oxopropanenitrile

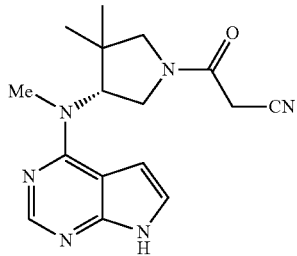 [SMILES: CN(c1ncnc2[nH]ccc12)[C@H]1CN(C(=O)CC#N)CC1(C)C]

6 g of ethyl acetoacetate was added to a 100-mL round-bottomed flask, and then dissolved with 60 mL of toluene. After 4.78 mL of benzyl alcohol was added into the solution, the reaction mixture was treated with 1.21 g of triphenylphosphine. After the reaction mixture was refluxed for about 12 hours, the reaction solution was distilled under reduced pressure to remove the solvent. The resulting residue was purified by flash column chromatography (EtOAc:n-Hexane=1:20). The resulting fraction was concentrated under reduced pressure and then further under vacuum. As a result, 6.69 g of benzyl 3-oxobutanoate was obtained with a yield of about 75.1%.

6.69 g of 3-oxobutanoate was added to a 250-mL round-bottomed flask and then dissolved with 67.0 mL of tetrahydrofuran. After 3.48 g of sodium hydride (sodium hydride (60 wt %) was added thereto at about 0° C., the reaction mixture was stirred at room temperature for about 1 hour. Then, 6.48 mL of iodomethane was added at about 0° C. and stirred at room temperature for about 12 hours. Then, the reaction solution was distilled under reduced pressure to remove the solvent, and then extracted with 100 mL of ethyl acetate (EtOAc), 100 mL of saturated brine, and 50 mL of ammonium chloride ($NH_4Cl$) to collect an organic phase. The collected organic phase was filtered with sodium sulfate ($Na_2SO_4$). The resulting filtrate was distilled under reduced pressure, and then the resulting residue was purified by flash column chromatography (EtOAc:n-Hexane=1:8). As a result, 6.91 g of benzyl-2,2-dimethyl-3-oxobutanoate was obtained with a yield of about 90.1%.

9.69 g of 2,2-dimethyl-3-oxobutanoate was added to a 250-mL round-bottomed flask, and then 195 mL of benzene was added thereto. After 4.90 mL of ethylene glycol was added thereto, 0.41 g of p-toluenesulfonic acid monohydrate was added into the reaction mixture. The reaction mixture was then refluxed with a Dean-Stark trap for about 24 hours at 120° C. The resulting reaction solution was distilled under reduced pressure to remove the solvent, and then extracted with 100 mL of ethyl acetate (EtOAc), 200 mL of saturated brine, and 100 mL of a saturated sodium hydrogen carbonate ($NaHCO_3$) aqueous solution to collect an organic phase. The collected organic phase was filtered with sodium sulfate ($Na_2SO_4$). The resulting filtrate was distilled under reduced pressure, and the resulting residue was purified by flash column chromatography (EtOAc:n-Hexane=1:10). The resulting fraction was concentrated under reduced pressure and then further under vacuum. As a result, 9.47 g of benzyl-2-methyl-2-(2-methyl-1,3-dioxolan-2-yl)propanoate was obtained with a yield of about 81.6%.

9.47 g of benzyl 2-methyl-2-(2-methyl-1,3-dioxolan-2-yl)propanoate was added to a 100-mL round-bottomed flask and then dissolved with 95.0 mL of methanol. After 9.47 g of a 10 w/w % palladium/carbon (Pd/C) was added into the solution, a hydrogen-containing balloon was installed on the reaction flask. The reaction mixture was vigorously stirred for about 24 hours and then filtered through a Celite™ 545 filter agent. The resulting filtrate was concentrated under reduced pressure. The resulting fraction was concentrated under reduced pressure and then further under vacuum. As a result, 5.94 g of 2-methyl-2-(2-methyl-1,3-dioxolan-2-yl)propanoic acid was obtained with a yield of about 95.2%.

5.94 g of 2-methyl-2-(2-methyl-1,3-dioxolan-2-yl)propanoic acid was added to a 100-mL round-bottomed flask, and 53 mL of dichloromethane ($CH_2Cl_2$) was added thereto. After 9.51 mL of triethylamine was added thereto at about −20° C., 3.59 mL of ethyl chloroformate was added to the reaction mixture and then stirred at about −20° C. for about 40 minutes. Then, 4.78 mL of (R)-(+)-1-phenylethylamine ((R)-(+)-1-phenylethylamine) was slowly dropwise added thereto at about −20° C., and the reaction mixture was stirred at room temperature for about 12 hours and then extracted with 50 mL of water to collect an organic phase. The collected organic phase was filtered with sodium sulfate ($Na_2SO_4$). The resulting filtrate was concentrated under reduced pressure, and then the resulting residue was purified by flash column chromatography (EtOAc:n-Hexane=1:8). As a result, 1.89 g of (R)-2-methyl-2-(2-methyl-1,3-dioxolan-2-yl)-N-(1-phenylethyl)propanamide was obtained with a yield of about 20.0%.

1.89 g of (R)-2-methyl-2-(2-methyl-1,3-dioxolan-2-yl)-N-(1-phenylethyl)propanamide was added to a 100-mL round-bottomed flask, and then dissolved with 18.0 mL of diethyl ether and 8.00 mL of 1,4-dioxane. Then, a mixture obtained by dissolving 0.590 mL of bromine in 30.0 mL of 1,4-dioxane was dropwise added thereto at about 0° C. The reaction mixture was stirred at room temperature for about 12 hours, concentrated under reduced pressure to remove the solvent, and then extracted with 18.0 mL of ethyl acetate (EtOAc), 18.0 mL of saturated brine, and 18.0 mL of a saturated sodium thiosulfate ($Na_2S_2O_3$) to collect an organic phase. The collected organic phase was filtered with sodium sulfate ($Na_2SO_4$). The resulting filtrate was concentrated under reduced pressure, and then the resulting residue was purified by flash column chromatography (EtOAc:n-Hexane=1:10). The resulting fraction was concentrated under reduced pressure and then further under vacuum. As a result, 2.29 g of (R)-2-(2-(bromomethyl)-1,3-dioxolan-2-yl)-2-methyl-N-(1-phenylethyl)propanamide was obtained with a yield of about 94.2%.

2.29 g of (R)-2-(2-(bromomethyl)-1,3-dioxolan-2-yl)-2-methyl-N-(1-phenylethyl)propanamide was added to a 50-mL round-bottomed flask and then dissolved with 22.0 mL of N,N-dimethylformamide. After 0.440 g of sodium hydride (60 wt %) was added thereto at about 0° C. The reaction mixture was stirred at about 0° C. for about 3 hours, and then extracted with 200 mL of ethyl acetate (EtOAc) and 500 mL of saturated brine to collect an organic phase. The collected organic phase was filtered with sodium sulfate ($Na_2SO_4$). The resulting filtrate was distilled under reduced pressure, and the resulting residue was purified by flash column chromatography (EtOAc:$CH_2Cl_2$=1:100). As a result, 1.07 g of (R)-9,9-dimethyl-7-(1-phenylethyl)-1,4-dioxa-7-azaspiro[4.4]nonane-8-one was obtained with a yield of about 60.5%.

1.07 g of (R)-9,9-dimethyl-7-(1-phenylethyl)-1,4-dioxa-7-azaspiro[4.4]nonane-8-one was added to a 50-mL round-bottomed flask, and 11.0 mL of acetone was then added thereto. After 4.67 mL of a 1N HCl solution was added thereto at room temperature, the reaction mixture was refluxed at about 60° C. for about 12 hours and then concentrated under reduced pressure. The reaction mixture was extracted with 50.0 mL of ethyl acetate (EtOAc) and 50.0 mL of saturated brine to collect an organic phase. The collected organic phase was filtered with sodium sulfate ($Na_2SO_4$). The resulting filtrate was concentrated under reduced pressure. As a result, 0.840 g of (R)-3,3-dimethyl-1-(1-phenylethyl)pyrrolidine-2,4-dione was obtained with a yield of about 93.2%.

0.840 g of (R)-3,3-dimethyl-1-(1-phenylethyl)pyrrolidine-2,4-dione was added to a 50-mL round-bottomed flask, and 9.00 mL of ethanol was added thereto. After 395 mg of hydroxylamine hydrochloride and 0.782 mL of triethylamine were added thereto, the reaction mixture was stirred at room temperature for 5 hrs. The reaction mixture was concentrated under reduced pressure, and then the resulting residue was purified by flash column chromatography (EtOAc:$CH_2Cl_2$=1:3). As a result, 730 mg of (R)-4-(hydroxyimino)-3,3-dimethyl-1-(1-phenylethyl)pyrrolidine-2-one was obtained with a yield of about 94.1%.

730 mg of (R)-4-(hydroxyimino)-3,3-dimethyl-1-(1-phenylethyl)pyrrolidine-2-one was added to a 50-mL round-bottomed flask, and 36.5 mL of methanol was added thereto. After 1.56 mL of Raney®-nickel was added thereto, a hydrogen-containing balloon was installed on the reaction flask. The reaction mixture was vigorously stirred for about 12 hours and then filtered through a Celite™ 545 filter agent. The resulting filtrate was concentrated under reduced pressure. The resulting fraction was concentrated under reduced pressure and then further under vacuum. The resulting residue was purified by flash column chromatography (MeOH:$CH_2Cl_2$=2:98). As a result, 264 mg of (R)-4-amino-3,3-dimethyl-1-((R)-1-phenylethyl)pyrrolidine-2-one was obtained with a yield of about 38.4%, and 300 mg of (S)-4-amino-3,3-dimethyl-1-((R)-1-phenylethyl)pyrrolidine-2-one was obtained with a yield of about 43.7%.

264 mg of (R)-4-amino-3,3-dimethyl-1-((R)-1-phenylethyl)pyrrolidine-2-one was added to a 50-mL round-bottomed flask, and 13.0 mL of tetrahydrofuran was added thereto. After 189 mg of lithium aluminum hydride ($LiAlH_4$) was slowly dropwise added thereto at about 0° C., the reaction mixture was refluxed for about 12 hours and then cooled at 0° C. 1.15 m L of deionized water was slowly added to the reaction mixture while cooling. After the reaction mixture was stirred for about 5 minutes, 1.15 mL of a 15% sodium hydroxide (NaOH) aqueous solution was added to terminate the reaction. The reaction mixture was filtered through a Celite™ 545 filter agent. The resulting filtrate was distilled under reduced pressure. The distilled product was extracted with 10.0 mL of ethyl acetate (EtOAc) and 10.0 mL of saturated brine to collect an organic phase. The collected organic phase was filtered with sodium sulfate ($Na_2SO_4$). The resulting filtrate was concentrated under reduced pressure. As a result, 240 mg of (R)-4,4-dimethyl-1-((R)-1-phenylethyl)pyrrolidine-3-amine was obtained with a yield of about 96.8%.

240 mg of (R)-4,4-dimethyl-1-((R)-1-phenylethyl)pyrrolidine-3-amine was added to a 25-mL round-bottomed flask, and then 2.40 mL of tetrahydrofuran and 2.40 mL of saturated sodium hydrogen carbonate ($NaHCO_3$) aqueous solution were added thereto. After 252 mg of di-tert-butyl dicarbamate ($Boc_2O$) was added thereto, the reaction mixture was vigorously stirred overnight and then concentrated under reduced pressure. The reaction mixture was then extracted with 5.00 mL of ethyl acetate (EtOAc) and 5.00 mL of saturated brine to collect an organic phase. The collected organic phase was filtered with sodium sulfate ($Na_2SO_4$). The resulting filtrate was concentrated under reduced pressure. As a result, 335 mg of tert-butyl ((R)-4,4-dimethyl-1-((R)-1-phenylethyl)pyrrolidine-3-yl)carbamate was obtained with a yield of about 95.7%.

335 mg of tert-butyl ((R)-4,4-dimethyl-1-((R)-1-phenylethyl)pyrrolidine-3-yl)carbamate was added to a 25-mL round-bottomed flask, and 5.03 mL of tetrahydrofuran was added thereto. After 252 mg of lithium aluminum hydride ($LiAlH_4$) was slowly dropwise added at 0° C., the reaction mixture was refluxed for about 12 hours and then cooled at 0° C. 1.00 mL of deionized water was slowly added while cooling. After the reaction mixture was stirred for about 5 minutes, 1.00 mL of a 15% sodium hydroxide (NaOH) aqueous solution was added to terminate the reaction. The reaction mixture was filtered through a Celite™ 545 filter agent. The resulting filtrate was concentrated under reduced pressure. As a result, 238 mg of (R)—N,4,4-trimethyl-1-((R)-1-phenylethyl)pyrrolidine-3-amine was obtained with a yield of about 97.9%.

238 mg of (R)—N,4,4-trimethyl-1-((R)-1-phenylethyl)pyrrolidine-3-amine was added into a 50-mL round-bottomed flask, and 4.80 mL of deionized water was added thereto. After 165 mg of 6-chloro-7-deazapurine and 284 mg of potassium carbonate ($K_2CO_3$) were sequentially added into the reaction mixture, the reaction mixture was refluxed for about 24 hours and then cooled at room temperature. The reaction mixture was extracted three times with 10.0 mL of dichloromethane ($CH_2Cl_2$) to collect an organic phase. The collected organic phase was concentrated under reduced pressure, and then the resulting residue was purified by flash column chromatography (MeOH:$CH_2Cl_2$=2:98). As a result, 106 mg of N—((R)-4,4-dimethyl-1-((R)-1-phenylethyl)pyrrolidine-3-yl)-N-methyl-7H-pyrrolo[2,3-d]pyrimidine-4-amine was obtained with a yield of about 30.7%.

106 mg of N—((R)-4,4-dimethyl-1-((R)-1-phenylethyl)pyrrolidine-3-yl)-N-methyl-7H-pyrrolo[2,3-d]pyrimidine-4-amine was added to a 10-mL round-bottomed flask, and then dissolved with 1.06 mL of methanol. After 106 mg of a 10 w/w % palladium/carbon (Pd/C) was added thereto, a hydrogen-containing balloon was installed on the reaction flask. The reaction mixture was vigorously stirred overnight and then filtered through a. Celite™ 545 filter agent. The resulting filtrate was concentrated under reduced pressure. As a result, 58.2 mg of (R)—N-(4,4-dimethylpyrrolidine-3-yl)-N-methyl-7H-pyrrolo[2,3-d]pyrimidine-4-amine was obtained with a yield of about 79.1%.

57.0 mg of (R)—N-(4,4-dimethylpyrrolidine-3-yl)-N-methyl-7H-pyrrolo[2,3-d]pyrimidine-4-amine was added to a 10-mL round-bottomed flask and then dissolved with 1.14 mL of n-butanol. After 0.247 mL of ethyl cyanoacetate was added into the solution, the reaction mixture was treated with 0.0174 mL of 1,8-diazabicyclo[5.4.0]undec-7-ene (DBU) and then heated at about 80° C. for about 24 hours. After termination of the reaction, the reaction solution was distilled under reduced pressure to remove the solvent. The resulting residue was purified by flash column chromatography (MeOH:$CH_2Cl_2$=2:98). The resulting fraction was concentrated under reduced pressure and then further under vacuum. As a result, 41.4 mg of (R)-3-(3,3-dimethyl-4-(methyl(7H-pyrrolo[2,3-d]pyrimidine-4-yl)amino)pyrrolidine-1-yl)-3-oxopropanenitrile was obtained with a yield of about 57.1%.

¹H NMR (400 MHz, CDCl₃) δ 9.58 (s, 1H), 8.25 (s, 1H), 7.07 (q, J=3.6, 5.6 Hz, 1H), 6.61 (q, J=2.0, 3.6 Hz, 1H), 5.76-5.63 (m, 1H), 4.08-3.97 (m, 1H), 3.87-3.76 (m, 1H), 3.57-3.52 (m, 1H), 3.47 (d, J=7.2 Hz, 2H), 3.41-3.35 (m, 1H), 3.34 (d, J=11.6 Hz, 3H), 1.27 (s, 3H), 1.04 (s, 3H).

LRMS (ESI) calcd for (C₁₆H₂₀N₆O+H⁺) 313.1, found 313.2.

Example 44. (S)-3-(3,3-dimethyl-4-(methyl(7H-pyrrolo[2,3-d]pyrimidine-4-yl)amino)pyrrolidine-1-yl)-3-oxopropanenitrile

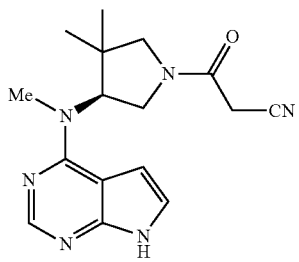 [SMILES: CN(c1ncnc2[nH]ccc12)[C@@H]1CN(C(=O)CC#N)CC1(C)C]

300 mg of (S)-4-amino-3,3-dimethyl-1-((R)-1-phenylethyl)pyrrolidine-2-one (an intermediated obtained during synthesis in Example 43) was added to a 50-mL round-bottomed flask, and 15.0 mL of tetrahydrofuran was added thereto. After 215 mg of lithium aluminum hydride (LiAlH₄) was slowly dropwise added thereto at 0° C., the reaction mixture was refluxed for about 12 hours and then cooled 0° C. 1.50 mL of deionized water was slowly added thereto while cooling. After the reaction mixture was stirred for about 5 minutes, 1.50 mL of a 15% sodium hydroxide (NaOH) aqueous solution was added thereto to terminate the reaction. The reaction mixture was filtered through a Celite™ 545 filter agent. The resulting filtrate was distilled under reduced pressure. Then, the reaction mixture was extracted with 10.0 mL of ethyl acetate (EtOAc) and 10.0 mL of saturated brine to collect an organic phase. The collected organic phase was filtered with sodium sulfate (Na₂SO₄). The resulting filtrate was concentrated under reduced pressure. As a result, 254 mg of (S)-4,4-dimethyl-1-((R)-1-phenylethyl)pyrrolidine-3-amine was obtained with a yield of about 90.4%.

250 mg of (S)-4,4-dimethyl-1-((R)-1-phenylethyl)pyrrolidine-3-amine was added into a 50-mL round-bottomed flask, and then 2.50 mL of tetrahydrofuran and 2.50 mL of a saturated sodium hydrogen carbonate (NaHCO₃) solution were added thereto. After 262 mg of di-tert-butyl dicarbamate (Boc₂O) was added, the reaction mixture was vigorously stirred overnight and then concentrated under reduced pressure. Then, the reaction mixture was extracted with 3.00 mL of ethyl acetate (EtOAc) and 6.00 mL of saturated brine to collect an organic phase. The collected organic phase was filtered with sodium sulfate (Na₂SO₄). The resulting filtrate was concentrated under reduced pressure. As a result, 354 mg of tert-butyl ((S)-4,4-dimethyl-1-((R)-1-phenylethyl)pyrrolidine-3-yl)carbamate was obtained with a yield of about 96.7%.

354 mg of tert-butyl ((S)-4,4-dimethyl-1-((R)-1-phenylethyl)pyrrolidine-3-yl)carbamate was added to a 25-mL round-bottomed flask, and 5.30 mL of tetrahydrofuran was added thereinto. After 265 mg of lithium aluminum hydride (LiAlH₄) was slowly dropwise added thereinto at 0° C., the reaction mixture was refluxed for about 12 hours and then cooled at about 0° C. 1.00 mL of deionized water was added thereinto while cooling. After the reaction mixture was stirred for about 5 minutes, 1.00 mL of a 15% sodium hydroxide (NaOH) aqueous solution was added thereto to terminate the reaction. The reaction mixture was filtered through a Celite™ 545 filter agent. The resulting filtrate was concentrated under reduced pressure. As a result, 247 mg of (S)—N,4,4-trimethyl-1-((R)-1-phenylethyl)pyrrolidine-3-amine was obtained with a yield of about 96.1%.

247 mg of (S)—N,4,4-trimethyl-1-((R)-1-phenylethyl)pyrrolidine-3-amine was added to a 50-mL round-bottomed flask, and 4.94 mL of deionized water was added thereto. After 171 mg of 6-chloro-7-deazapurine and 293 mg of potassium carbonate (K₂CO₃) were sequentially added to the reaction mixture, the reaction mixture was refluxed for about 24 hours and then cooled at room temperature. The reaction mixture was extracted tree times with 5 mL of dichloromethane (CH₂Cl₂) to collect an organic phase. The collected organic phase was concentrated under reduced pressure. The resulting residue was purified by flash column chromatography (MeOH:CH₂Cl₂=2:98). As a result, 97.0 mg of N—((S)-4,4-dimethyl-1-((R)-1-phenylethyl)pyrrolidine-3-yl)-N-methyl-7H-pyrrolo[2,3-d]pyrimidine-4-amine was obtained with a yield of about 26.2%.

96.8 mg of N—((S)-4,4-dimethyl-1-((R)-1-phenylethyl)pyrrolidine-3-yl)-N-methyl-7H-pyrrolo[2,3-d]pyrimidine-4-amine was added to a 25-mL round-bottomed flask and then dissolved with 1.00 mL of methanol. After 96.8 mg of a 10 w/w % palladium/carbon (Pd/C) was added thereto, a hydrogen-containing balloon was installed on the reaction flask. The reaction mixture was vigorously stirred overnight and then filtered through a Celite™ 545 filter agent. The resulting filtrate was distilled under reduced pressure. As a result, 63.0 mg of (S)—N-(4,4-dimethylpyrrolidine-3-yl)-N-methyl-7H-pyrrolo[2,3-d]pyrimidine-4-amine was obtained with a yield of about 92.6%.

63.0 mg of (S)—N-(4,4-dimethylpyrrolidine-3-yl)-N-methyl-7H-pyrrolo[2,3-d]pyrimidine-4-amine was added to a 10-mL round-bottomed flask, and then dissolved with 1.26 mL of n-butanol. After 0.237 mL of ethyl cyanoacetate was added into the solution, the reaction mixture was treated with 0.0192 mL of 1,8-diazabicyclo[5.4.0]undec-7-ene (DBU) and then heated at about 80° C. for about 24 hours. After termination of the reaction, the reaction solution was distilled under reduced pressure to remove the solvent. The resulting residue was purified by flash column chromatography (MeOH:CH₂Cl₂=2:98). The resulting fraction was distilled under reduced pressure and then concentrated under vacuum. As a result, 26.3 mg of (S)-3-(3,3-dimethyl-4-(methyl(7H-pyrrolo[2,3-d]pyrimidine-4-yl)amino)pyrrolidine-1-yl)-3-oxopropanenitrile was obtained with a yield of about 32.8%.

¹H NMR (400 MHz, CDCl₃) δ 9.45 (s, 1H), 8.26 (s, 1H), 7.07 (q, J=3.2, 5.6 Hz, 1H), 6.61 (q, J=2.0, 3.6 Hz, 1H), 5.76-5.63 (m, 1H), 4.08-3.97 (m, 1H), 3.89-3.75 (m, 1H), 3.59-3.52 (m, 1H), 3.47 (d, J=7.6 Hz, 2H), 3.43-3.35 (m, 1H), 3.34 (d, J=11.6 Hz, 3H), 1.28 (s, 3H), 1.04 (s, 3H).

LRMS (ESI) calcd for (C₁₆H₂₀N₆O+H⁺) 313.1, found 313.1.

Example 45. 3-(4-((7H-pyrrolo[2,3-d]pyrimidine-4-yl)oxy)piperidine-1-yl)-3-oxopropanenitrile

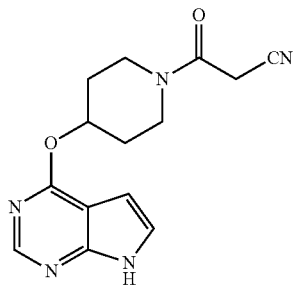 [SMILES: N#CCC(=O)N1CCC(Oc2ncnc3[nH]ccc23)CC1]

2.00 g of 4-hydroxypiperidine was added to a 100-mL round-bottomed flask, and then 20.0 mL of dichloromethane ($CH_2Cl_2$) and 20.0 mL of a saturated sodium hydrogen carbonate ($NaHCO_3$) solution were added thereto. After 4.32 g of di-tert-butyl dicarbamate ($Boc_2O$) was added thereto, the reaction mixture was vigorously stirred for about 15 hours and then concentrated under reduced pressure. The aqueous phase was extracted with 20.0 mL of ethyl acetate (EtOAc) to collect an organic phase. The collected organic phase was washed with 10.0 mL of deionized water and 15.0 mL of saturated brine. The organic phase was then filtered with sodium sulfate ($Na_2SO_4$). The resulting filtrate was distilled under reduced pressure. As a result, 3.871 g of tert-butyl 4-hydroxypiperidine-1-carboxylate was obtained with a yield of about 97.2%.

300 mg of 6-chloro-7-deazapurine was added to a 50-mL round-bottomed flask, and then 3.75 mL of N,N-dimethylformamide was added. After 86.0 mg of sodium hydride (60 wt %) was added thereto at about 0° C., the reaction mixture was refluxed at room temperature for about 15 minutes. After 0.403 mL of 2-(trimethylsillyl)ethoxymethyl chloride) was added thereto, the reaction mixture was stirred for about 30 minutes and concentrated under reduced pressure. The reaction mixture was extracted with 4.50 mL of ethyl acetate (EtOAc) and 4.50 mL of deionized water to collect an organic phase. The collected organic phase was filtered with magnesium sulfate ($MgSO_4$). The resulting filtrate was distilled under reduced pressure. As a result, 534 mg of 4-chloro-7-((2-(trimethylsillyl)ethoxy)methyl)-7H-pyrrolo[2,3-d]pyrimidine was obtained with a yield of about 96.6%.

408 mg of tert-butyl 4-hydroxypiperidine-1-carboxylate was added to a 50-mL round-bottomed flask, and 5.60 mL of dimethyl sulfoxide (DMSO) was added thereinto. After 61.4 mg of sodium hydride (60 wt %) was added thereinto at about 0° C., the reaction mixture was refluxed at room temperature for about 1.5 hours. Then, a solution of 574 mg of 4-chloro-7-((2-(trimethylsillyl)ethoxy)methyl)-7H-pyrrolo[2,3-d]pyrimidine dissolved in 4.60 mL of dimethyl sulfoxide (DMSO) was slowly dropwise added into the reaction mixture, and the reaction mixture was stirred at about 50° C. for about 2 hours and then cooled down to room temperature. The reaction mixture was then extracted with 10.0 mL of ethyl acetate (EtOAc) and 10.0 mL of deionized water to collect an organic phase. The collected organic phase was filtered with sodium sulfate ($Na_2SO_4$). The resulting filtrate was distilled under reduced pressure, and then the resulting residue was purified by flash column chromatography (EtOAc:Hexane=1:5). As a result, 457 mg of tert-butyl 4-((7-((2-(trimethylsillyl)ethoxy)methyl)-7H-pyrrolo[2,3-d]pyrimidine-4-yl)oxy)piperidine-1-carboxylate was obtained with a yield of about 66.6%.

452 mg of tert-butyl 4-((7-((2-(trimethylsillyl)ethoxy)methyl)-7H-pyrrolo[2,3-d]pyrimidine-4-yl)oxy)piperidine-1-carboxylate was added to a 50-mL round-bottomed flask, and 5.00 mL of tetrahydrofuran was added thereinto. After 20.4 mL of a solution of 1.0 M tetrabutylammonium fluoride in tetrahydrofuran was added thereinto, the reaction mixture was refluxed at room temperature for about 5 hours and then cooled down to room temperature. The reaction mixture was concentrated under reduced pressure and then extracted with 100 mL of ethyl acetate (EtOAc) and 100 mL of deionized water to collect an organic phase. The collected organic phase was filtered with sodium sulfate ($Na_2SO_4$). The resulting filtrated was distilled under reduced pressure, and then the resulting residue was purified by flash column chromatography (EtOAc:Hexane=1:6). As a result, 310 mg of tert-butyl 4-((7H-pyrrolo[2,3-d]pyrimidine-4-yl)oxy)piperidine-1-carboxylate was obtained with a yield of about 95.7%.

310 mg of tert-butyl 4-((7H-pyrrolo[2,3-d]pyrimidine-4-yl)oxy)piperidine-1-carboxylate was added to a 50-mL round-bottomed flask, and 6.00 mL of 1,4-dioxane was added thereinto. After 10.0 mL of 4N HCl solution was added thereinto, the reaction mixture was stirred at room temperature for about 2 hours. Then, 20.0 mL of ethyl acetate (EtOAc) was added into the reaction mixture and a 10% ammonium hydroxide solution was added to basify the reaction mixture. An organic phase was filtered with sodium sulfate ($Na_2SO_4$). The resulting filtrate was distilled under reduced pressure. As a result, 230 mg of 4-(piperidine-4-yloxy)-7H-pyrrolo[2,3-d]pyrimidine was obtained with a quantitative yield.

177 mg of 4-(piperidine-4-yloxy)-7H-pyrrolo[2,3-d]pyrimidine was added to a 25-mL round-bottomed flask and then dissolved with 3.00 mL of dichloromethane ($CH_2Cl_2$). After 0.0480 mL of chloroacetyl chloride was added into the solution, the reaction mixture was treated with 0.211 mL of N,N-diisopropylethylamine and then stirred overnight at room temperature. The reaction mixture was concentrated under reduced pressure, and the resulting residue was purified by flash column chromatography (EtOAc:Hexane=1:6). The resulting fraction was concentrated under reduced pressure and then further under vacuum. As a result, 56.0 mg of 1-(4-((7H-pyrrolo[2,3-d]pyrimidine-4-yl)oxy)piperidine-1-yl)-2-chloroethane-1-one was obtained with a yield of about 23.5%.

55.6 mg of 1-(4-((7H-pyrrolo[2,3-d]pyrimidine-4-yl)oxy)piperidine-1-yl)-2-chloroethane-1-one was added to a 25-mL round-bottomed flask and then dissolved with 1.00 mL of N,N-dimethylformamide. After 24.3 mg of potassium cyanide was added into the solution, the reaction mixture was stirred overnight at about 30° C. to 40° C. The reaction mixture was concentrated under reduced pressure, and then the resulting residue was purified by flash column chromatography (EtOAc:Hexane=1:1). The resulting fraction was concentrated under reduced pressure and then further under vacuum. As a result, 35.4 mg of 3-(4-((7H-pyrrolo[2,3-d]pyrimidine-4-yl)oxy)piperidine-1-yl)-3-oxopropanenitrile was obtained with a yield of about 49.4%.

$^1$H NMR (400 MHz, $CDCl_3$) δ12.03 (s, 1H), 8.34 (s, 1H), 7.35 (t, J=3.2 Hz, 1H), 6.47 (q, J=2.0, 3.6 Hz, 1H), 5.58-5.43 (m, 1H), 4.08 (s, 2H), 3.90-3.86 (m, 1H), 3.63-3.59 (m, 1H), 3.47-3.32 (m, 2H), 2.09-2.00 (m, 2H), 1.82-1.77 (m, 1H), 1.69-1.61 (m, 1H).

LRMS (ESI) calcd for ($C_{14}H_{15}N_5O_2+H^+$) 286.1, found 286.1.

Example 46. 3-((4-((7H-pyrrolo[2,3-d]pyrimidine-4-yl)oxy)piperidine-1-yl)sulfonyl)benzonitrile

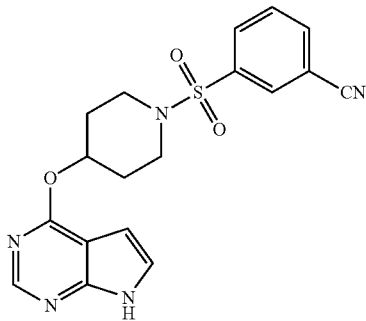 [SMILES: N#Cc1cccc(S(=O)(=O)N2CCC(Oc3ncnc4[nH]ccc34)CC2)c1]

50.0 mg of 4-(piperidine-4-yloxy)-7H-pyrrolo[2,3-d]pyrimidine was added to a 25-mL round-bottomed flask and then dissolved with 1.00 mL of dichloromethane ($CH_2Cl_2$). After 46.0 mg of 3-cyanobenzenesulfonyl chloride was added thereinto, the reaction mixture was treated with 0.0600 mL of N,N-diisopropylethylamine and then stirred overnight at room temperature. The reaction mixture was concentrated under reduced pressure, and then the resulting residue was purified by flash column chromatography (EtOAc:Hexane=1:1). The resulting fraction was concentrated under reduced pressure and then further under vacuum. As a result, 27.7 mg of 3-((4-((7H-pyrrolo[2,3-d]pyrimidine-4-yl)oxy)piperidine-1-yl)sulfonyl)benzonitrile was obtained with a yield of about 31.4%.

$^1$H NMR (400 MHz, $CDCl_3$) δ12.02 (s, 1H), 8.29 (s, 1H), 8.26-8.21 (m, 2H), 8.11-8.08 (m, 1H), 7.89 (t, J=8.0 Hz, 1H), 7.32 (q, J=2.4, 2.8 Hz, 1H), 6.30 (q, J=2.0, 3.2 Hz, 1H), 5.32-5.27 (m, 1H), 3.38-3.50 (m, 2H), 3.01-2.95 (m, 2H), 2.11-2.07 (m, 2H), 1.85-1.77 (m, 2H).

LRMS (ESI) calcd for ($C_{18}H_{17}N_5O_3S+H^+$) 384.1, found 384.1.

Example 47. 3-(3-(((7H-pyrrolo[2,3-d]pyrimidine-4-yl)oxy)methyl)piperidine-1-yl)-3-oxopropanenitrile

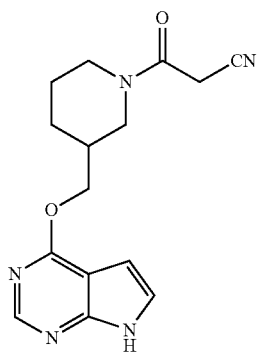 [SMILES: N#CCC(=O)N1CCCC(COc2ncnc3[nH]ccc23)C1]

1.05 g of 3-piperidinemethanol was added to a 100-mL round-bottomed flask, and 19.0 mL of tetrahydrofuran and 19.0 mL of saturated sodium hydrogen carbonate ($NaHCO_3$) solution were added thereinto. After 1.19 g of di-tert-butyl dicarbamate ($Boc_2O$) was added thereinto, the reaction mixture was stirred for about 48 hours and then refluxed for about 24 hours. 2.53 mL of triethylamine was added into the reaction mixture and then stirred at room temperature for about 1 hour. The aqueous phase was extracted with 20.0 mL of ethyl acetate (EtOAc) to collect an organic phase. The collected organic phase was washed with 10.0 mL of deionized water and 15.0 mL of saturated brine. The organic phase was then filtered with sodium sulfate ($Na_2SO_4$). The resulting filtrate was distilled under reduced pressure, and then the resulting residue was purified by flash column chromatography (MeOH:$CH_2Cl_2$=0:100→1:80→1:50). As a result, 964 mg of tert-butyl-3-(hydroxymethyl)piperidine-1-carboxylate was obtained with a yield of about 49.0%.

307 mg of 6-chloro-7-deazapurine was added to a 50-mL round-bottomed flask, and 4.00 mL of N,N-dimethylformamide was added thereinto. After 132 mg of sodium hydride (60 wt %) was added thereto at about 0° C., the reaction mixture was stirred at room temperature for about 20 minutes. Then, 0.370 mL of 2-(trimethylsillyl)ethoxymethyl chloride was added thereinto, the reaction mixture was stirred at room temperature for about 1 hour and concentrated under reduced pressure. The reaction mixture was extracted with 5.00 mL of ethyl acetate (EtOAc) and 5.00 mL of deionized water to collect an organic phase. The organic phase was filtered with magnesium sulfate ($MgSO_4$). The resulting filtrate was distilled under reduced pressure. As a result, 252 mg of 4-chloro-7-((2-(trimethylsillyl)ethoxy)methyl)-7H-pyrrolo[2,3-d]pyrimidine was obtained with a yield of about 45.0%.

192 mg of tert-butyl 3-(hydroxymethyl)piperidine-1-carboxylate was added to a 50-mL round-bottomed flask, and 2.50 mL of dimethyl sulfoxide (DMSO) was added thereinto. After 53.4 mg of sodium hydride (60 wt %) was added thereinto at about 0° C., the reaction mixture was stirred at room temperature for about 1.5 hour. Then, a solution of 252 mg of 4-chloro-7-((2-(trimethylsillyl)ethoxy)methyl)-7H-pyrrolo[2,3-d]pyrimidine in 2.00 mL of dimethyl sulfoxide (DMSO) was slowly dropwise added thereinto, the reaction mixture was stirred at about 50° C. for about 2 hours and then cooled down to room temperature. Then, the reaction mixture was extracted with 10.0 mL of ethyl acetate (EtOAc) and 10.0 mL of deionized water to collect an organic phase. The organic phase was filtered with sodium sulfate ($Na_2SO_4$). The resulting filtrate was distilled under reduced pressure, and then the resulting residue was purified by flash column chromatography (MeOH:$CH_2Cl_2$=0:100→1:80→1:50). As a result, 282 mg of tert-butyl-3-(((7-((2-(trimethylsillyl)ethoxy)methyl)-7H-pyrrolo[2,3-d]pyrimidine-4-yl)oxy)methyl)piperidine-1-carboxylate was obtained with a yield of about 71.0%.

280 mg of tert-butyl 3-(((7-((2-(trimethylsillyl)ethoxy)methyl)-7H-pyrrolo[2,3-d]pyrimidine-4-yl)oxy)methyl)piperidine-1-carboxylate was added to a 50-mL round-bottomed flask, and then 3.00 mL of tetrahydrofuran was added thereto. After 6.20 mL of a solution of 1.0 M tetrabutylammonium fluoride in tetrahydrofuran was added into the reaction mixture over about 2 hours, the reaction mixture was stirred at room temperature for about 24 hours and then concentrated under reduced pressure. The reaction mixture was extracted with 100 mL of ethyl acetate (EtOAc) and 100 mL of deionized water to collect an organic phase. The organic phase was filtered with sodium sulfate ($Na_2SO_4$). The resulting filtrate was distilled under reduced pressure, and then the resulting residue was purified by flash column chromatography (MeOH:$CH_2Cl_2$=0:100→1:80→1:50). As a result, 120 mg of tert-butyl-3-(((7H-pyrrolo[2,3-d]pyrimidine-4-yl)oxy)methyl)piperidine-1-carboxylate was obtained with a yield of about 58.0%.

203 mg of tert-butyl-3-(((7H-pyrrolo[2,3-d]pyrimidine-4-yl)oxy)methyl)piperidine-1-carboxylate was added to a 50-mL round-bottomed flask, and then 2.00 mL of 1,4-dioxane was added thereinto. After 4.00 mL of 4N HCl solution was added into the reaction mixture, the reaction mixture was stirred at room temperature for about 2 hours. Then, the reaction mixture was distilled under reduced pressure. Then, 10.0 mL of ethyl acetate (EtOAc) was added into the reaction mixture, and 10.0 mL of a 10% ammonium hydroxide solution was added to basify the reaction mixture (pH=10). An organic phase was filtered with sodium sulfate ($Na_2SO_4$). The resulting filtrate was distilled under reduced pressure. As a result, 141 mg of 4-(piperidine-3-ylmethoxy)-7H-pyrrolo[2,3-d]pyrimidine was obtained with a yield of about 61%.

140 mg of 4-(piperidine-3-ylmethoxy)-7H-pyrrolo[2,3-d]pyrimidine was added to a 25-mL round-bottomed flask, and then dissolved with 2.50 mL of dichloromethane ($CH_2Cl_2$). After 0.0710 mL of chloroacetyl chloride was added into the solution, the reaction mixture was treated with 0.250 mL of N,N-diisopropylethylamine and then stirred at room temperature for about 1 hour. The reaction mixture was concentrated under reduced pressure, and then the resulting residue was purified by flash column chromatography ($MeOH:CH_2Cl_2$=0:100→1:80→1:50). The resulting fraction was concentrated under reduced pressure and then further under vacuum. As a result, 54.9 mg of 1-(3-(((7H-pyrrolo[2,3-d]pyrimidine-4-yl)oxy)methyl)piperidine-1-yl)-2-chloroethane-1-one was obtained with a yield of about 30.0%.

54.9 mg of 1-(3-(((7H-pyrrolo[2,3-d]pyrimidine-4-yl)oxy)methyl)piperidine-1-yl)-2-chloroethane-1-one was added to a 5-mL round-bottomed flask, and then dissolved with 1.10 mL of N,N-dimethylformamide. After 22.4 mg of potassium cyanide was added into the solution, the reaction mixture was stirred at about 30° C. to 40° C. for about 1 hour. After the reaction mixture was concentrated under reduced pressure, 5.00 mL of deionized water and 5.00 mL of dichloromethane ($CH_2Cl_2$) were added into the resulting residue and then stirred for about 5 minutes. An organic phase was separated and concentrated under reduced pressure, and then the resulting residue was purified by flash column chromatography ($MeOH:CH_2Cl_2$=0:100→1:80→1:50). The resulting fraction was concentrated under reduced pressure and then further under vacuum. As a result, 34.4 mg of 3-(3-(((7H-pyrrolo[2,3-d]pyrimidine-4-yl)oxy)methyl)piperidine-1-yl)-3-oxopropanenitrile was obtained with a yield of about 64.0%.

$^1$H NMR (400 MHz, DMSO) δ12.03 (s, 1H), 8.34 (s, 1H), 7.36 (s, 1H), 6.54-6.46 (m, 1H), 4.43-4.39 (m, 1H), 4.35-4.26 (m, 2H), 4.06-4.02 (m, 2H), 3.07-3.01 (m, 1H), 2.76-2.67 (m, 2H), 1.98-1.91 (m, 1H), 1.90-1.84 (m, 1H), 1.74-1.66 (m, 1H), 1.45-1.37 (m, 2H).

LRMS (ESI) calcd for ($C_{15}H_{17}N_5O_2$+H$^+$) 300.2, found 300.1.

Example 48. 3-((3-(((7H-pyrrolo[2,3-d]pyrimidine-4-yl)oxy)methyl)piperidine-1-yl)sulfonyl)benzonitrile

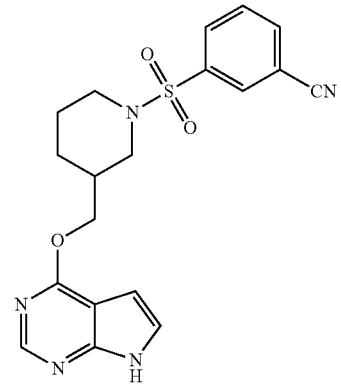 [SMILES: N#Cc1cccc(S(=O)(=O)N2CCCC(COc3ncnc4[nH]ccc34)C2)c1]

32.4 mg of 4-(piperidine-3-ylmethoxy)-7H-pyrrolo[2,3-d]pyrimidine was added to a 25-mL round-bottomed flask, and then dissolved with 1.00 mL of dichloromethane ($CH_2Cl_2$). After 30.2 mg of 3-cyanobenzenesulfonyl chloride was added into the solution, the reaction mixture was treated with 0.0250 mL of N,N-diisopropylethylamine and then stirred at room temperature for about 1 hour. The reaction mixture was concentrated under reduced pressure, and then the resulting residue was purified by flash column chromatography ($MeOH:CH_2Cl_2$=0:100→1:80→1:50). The resulting fraction was concentrated under reduced pressure and then further under vacuum. As a result, 30.1 mg of 3-((3-(((7H-pyrrolo[2,3-d]pyrimidine-4-yl)oxy)methyl)piperidine-1-yl)sulfonyl)benzonitrile was obtained with a yield of about 54.0%.

$^1$H NMR (400 MHz, CDCl$_3$) δ10.45 (s, 1H), 8.53 (s, 1H), 8.08 (s, 1H), 8.00 (d, J=8.0 Hz, 1H), 7.89 (d, J=7.6 Hz, 1H), 7.70 (t, J=8.0 Hz, 1H), 7.30 (d, J=3.6 Hz, 1H), 6.70 (d, J=3.2 Hz, 1H), 4.57 (dd, J=10.8, 5.2 Hz, 1H), 4.45 (dd, J=10.8, 8.0 Hz, 1H), 3.92-3.84 (m, 1H), 3.65 (d, J=11.6 Hz, 1H), 2.60-2.55 (m, 1H), 2.45 (t, J=10.8 Hz, 1H), 2.42-2.34 (m, 2H), 1.90-1.87 (m, 2H), 1.79-1.74 (m, 1H).

LRMS (ESI) calcd for ($C_{19}H_{19}N_5O_3S$+H$^+$) 398.1, found 398.1.

Example 49. 3-((4aR,7aR)-1-(7H-pyrrolo[2,3-d]pyrimidine-4-yl)octahydro-6H-pyrrolo[3,4-b]pyridine-6-yl)-3-oxopropanenitrile

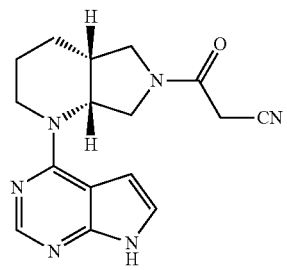 [SMILES: N#CCC(=O)N1C[C@H]2CCCN(c3ncnc4[nH]ccc34)[C@H]2C1]

100 mg of (R,R)-6-benzyl-octahydro-pyrrolo[3,4-b]pyridine dihydrochloride was added into a 25-mL round-bottomed flask, and 2.00 mL of deionized water was added thereinto. After 55.8 mg of 6-chloro-7-deazapurine was added into the reaction mixture, 191 mg of potassium carbonate ($K_2CO_3$) was added into the reaction mixture, and the reaction mixture was refluxed for about 36 hours and then cooled at room temperature. The reaction mixture was extracted three times with 3.00 mL of dichloromethane ($CH_2Cl_2$) to collect an organic phase. The collected organic phase was concentrated under reduced pressure. The resulting residue was purified by flash column chromatography (MeOH:$CH_2Cl_2$=2:98). As a result, 93.6 mg of 4-((4aR,7aR)-6-benzyl-octahydro-1H-pyrrolo[3,4-b]pyridine-1-yl)-7H-pyrrolo[2,3-d]pyrimidine was obtained with a yield of about 81.4%.

93.6 mg of 4-((4aR,7aR)-6-benzyl-octahydro-1H-pyrrolo[3,4-b]pyridine-1-yl)-7H-pyrrolo[2,3-d]pyrimidine was added to a 25-mL round-bottomed flask and then dissolved with 1.00 mL of methanol. After 40.0 mg of a 10 w/w % palladium/carbon (Pd/C) was added thereinto, a hydrogen-containing balloon was installed on the reaction flask. The reaction mixture was vigorously stirred for about 24 hours, and then filtered through a Celite™ 545 filter agent. The resulting filtrate was concentrated under reduced pressure. The resulting fraction was concentrated under reduced pressure and then further under vacuum. As a result, 60.1 mg of 4-((4aR,7aR)-octahydro-1H-pyrrolo[3,4-b]pyridine-1-yl)-7H-pyrrolo[2,3-d]pyrimidine was obtained with a yield of about 88.4%.

60.1 mg of 4-((4aR,7aR)-octahydro-1H-pyrrolo[3,4-b]pyridine-1-yl)-7H-pyrrolo[2,3-d]pyrimidine was added to a 5-mL round-bottomed flask, and then dissolved with 1.50 mL of n-butanol. After 0.237 mL of ethyl cyanoacetate was added into the solution, the reaction mixture was treated with 0.0169 mL of 1,8-diazabicyclo[5.4.0]undec-7-ene (DBU) and then heated at about 80° C. for about 24 hours. After termination of the reaction, the reaction solution was distilled under reduced pressure to remove the solvent. The resulting residue was purified by flash column chromatography (MeOH:$CH_2Cl_2$=2:98). The resulting fraction was concentrated under reduced pressure and then further under vacuum. As a result, 50.0 mg of 3-((4aR,7aR)-1-(7H-pyrrolo[2,3-d]pyrimidine-4-yl)octahydro-6H-pyrrolo[3,4-b]pyridine-6-yl)-3-oxopropanenitrile was obtained with a yield of about 63.3%.

$^1$H NMR (400 MHz, $CDCl_3$) δ10.04 (s, 1H), 8.36 (d, J=2.8 Hz, 1H), 7.15-7.12 (m, 1H), 6.58-6.54 (m, 1H), 5.65-5.51 (m, 1H), 4.65-4.57 (m, 1H), 4.01-3.49 (m, 4H), 3.46 (d, J=3.6 Hz, 2H), 3.41-3.20 (m, 1H), 2.53-2.39 (m, 1H), 2.01-1.94 (m, 2H), 1.80-1.69 (m, 1H), 1.54-1.42 (m, 1H).

LRMS (ESI) calcd for ($C_{16}H_{18}N_6O+H^+$) 311.2, found 311.1.

Example 50. 3-((4aS,7aS)-1-(7H-pyrrolo[2,3-d]pyrimidine-4-yl)octahydro-6H-pyrrolo[3,4-b]pyridine-6-yl)-3-oxopropanenitrile

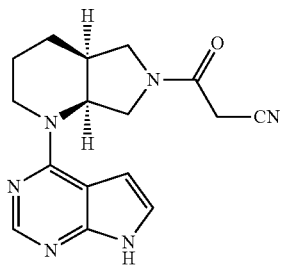 [SMILES: N#CCC(=O)N1C[C@@H]2CCCN(c3ncnc4[nH]ccc34)[C@@H]2C1]

100 mg of (S,S)-6-benzyl-octahydro-pyrrolo[3,4-b]pyridine dihydrochloride was added to a 25-mL round-bottomed flask, and 2.00 mL of deionized water was added thereinto. After 55.8 mg of 6-chloro-7-deazapurine and 191 mg of potassium carbonate ($K_2CO_3$) were sequentially added into the reaction mixture, the reaction mixture was refluxed for about 36 hours and then cooled down at room temperature. The reaction mixture was extracted three times with 3.00 mL of dichloromethane ($CH_2Cl_2$) to collect an organic phase. The organic phase was concentrated under reduced pressure, and the resulting residue was purified by flash column chromatography (MeOH:$CH_2Cl_2$=2:98). As a result, 114 mg of 4-((4aS,7aS)-6-benzyloctahydro-1-pyrrolo[3,4-b]pyridine-1-yl)-7H-pyrrolo[2,3-d]pyrimidine was obtained with a yield of about 99.1%.

114 mg of 4-((4aS,7S)-6-benzyloctahydro-1-pyrrolo[3,4-b]pyridine-1-yl)-7H-pyrrolo[2,3-d]pyrimidine was added to a 25-mL round-bottomed flask and then dissolved with 1.50 mL of methanol. After 20.0 mg of a 10 w/w % palladium/carbon (Pd/C) was added thereinto, a hydrogen-containing balloon was installed on the reaction flask. The reaction mixture was vigorously stirred for about 24 hours and then filtered through Celite™ 545 filter agent. The resulting filtrate was concentrated under reduced pressure. The resulting fraction was concentrated under reduced pressure and then further under vacuum. As a result, 370 mg of 4-((4aS,7aS)-octahydropyrrolo[3,4-b]pyridine-1-yl)-7H-pyrrolo[2,3-d]pyrimidine was obtained with a yield of about 66.0%.

70.0 mg of 4-((4aS,7aS)-octahydropyrrolo[3,4-b]pyridine-1-yl)-7H-pyrrolo[2,3-d]pyrimidine was added to a 5-mL round-bottomed flask, and then dissolved with 1.50 mL of n-butanol. After 0.240 mL of ethyl cyanoacetate was added into the solution, the reaction mixture was treated with 0.0170 mL of 1,8-diazabicyclo[5.4.0]undec-7-ene (DBU) and then heated at about 80° C. for about 12 hours. After termination of the reaction, the reaction solution was distilled under reduced pressure to remove the solvent. The resulting residue was purified by flash column chromatography (MeOH:$CH_2Cl_2$=2:98). The resulting fraction was concentrated under reduced pressure and then further under vacuum. As a result, 36.0 mg of 3-((4aS,7aS)-1-(7H-pyrrolo[2,3-d]pyrimidine-4-yl)octahydro-6H-pyrrolo[3,4-b]pyridine-6-yl)-3-oxopropanenitrile was obtained with a yield of about 56.4%.

$^1$H NMR (400 MHz, $CDCl_3$) δ 10.28 (s, 1H), 8.37 (d, J=2.8 Hz, 1H), 7.18-7.13 (m, 1H), 6.58-6.54 (m, 1H), 5.66-5.54 (m, 1H), 4.65-4.54 (m, 1H), 4.01-3.49 (m, 4H), 3.46 (d, J=12.4 Hz, 2H), 3.45-3.38 (m, 1H), 2.52-2.39 (m, 1H), 2.03-1.95 (m, 2H), 1.78-1.71 (m, 1H), 1.54-1.42 (m, 1H).

LRMS (ESI) calcd for ($C_{16}H_{18}N_6O+H^+$) 311.2, found 311.1.

Example 51. (R)-3-(3-(methyl(7H-pyrrolo[2,3-d]pyrimidine-4-yl)amino)pyrrolidine-1-yl)-3-oxopropanenitrile hydrochloride (Preparation of hydrochloride of Example 1)

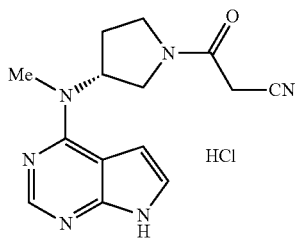 [SMILES: CN(c1ncnc2[nH]ccc12)[C@@H]1CCN(C(=O)CC#N)C1 ; Cl]

750 mg of (R)-3-(3-(methyl(7H-pyrrolo[2,3-d]pyrimidine-4-yl)amino)pyrrolidine-1-yl)-3-oxopropanenitrile (Example 1) was added to a 50-mL round-bottomed flask, and 48.0 mL of anhydrous tetrahydrofuran was added thereinto. Then, this mixture was refluxed until the mixture became a transparent solution. A solution of 1M HCl (available from Aldrich) dissolved in 2.77 mL of diethyl ether was slowly dropwise added into the solution. The resulting mixture was stirred under reflux for about 5 minutes, cooled down to room temperature, and then further stirred for about 1 hour. After the reaction mixture was filtered, the resulting solid product was dried under vacuum. As a result, 596 mg of (R)-3-(3-(methyl(7H-pyrrolo[2,3-d]pyrimidine-4-yl)amino)pyrrolidine-1-yl)-3-oxopropanenitrile hydrochloride was obtained with a yield of about 70.7%.

The compounds of Examples 1 to 36 are represented in the following tables.

| Example | $R^1$ | $R^2$ |
|---|---|---|
| 1 | Methyl | 2-Cyanoacetyl |
| 2 | Methyl | 2-Cyanoethyl |
| 3 | Methyl | Butyl |
| 4 | Methyl | 2-Azidoacetyl |
| 5 | Methyl | 3-Methylbutanoyl |
| 6 | Methyl | Isobutoxycarbonyl |
| 7 | Methyl | Anilinocarbonyl |
| 8 | Methyl | Methylsulfonyl |
| 9 | Methyl | (Trifluoromethyl)sulfonyl |
| 10 | Methyl | Ethylsulfonyl |
| 11 | Methyl | Propylsulfonyl |
| 12 | Methyl | Isopropylsulfonyl |
| 13 | Methyl | (1-Methyl-1H-imidazol-4-yl)sulfonyl |
| 14 | Methyl | Phenylsulfonyl |
| 15 | Methyl | (2-Fluorophenyl)sulfonyl |
| 16 | Methyl | (3-Fluorophenyl)sulfonyl |
| 17 | Methyl | (4-Fluorophenyl)sulfonyl |
| 18 | Methyl | (2-Cyanophenyl)sulfonyl |
| 19 | Methyl | (3-Cyanophenyl)sulfonyl |
| 20 | Methyl | (4-Cyanophenyl)sulfonyl |
| 21 | Methyl | (2-Nitrophenyl)sulfonyl |
| 22 | Methyl | (3-Nitrophenyl)sulfonyl |
| 23 | Methyl | (4-Nitrophenyl)sulfonyl |
| 24 | Methyl | m-Tolyl sulfonyl |
| 25 | Methyl | Tosyl |
| 26 | Methyl | (4-Methoxphenyl)sulfonyl |
| 27 | Methyl | ((4-Trifluoromethyl)phenyl)sulfonyl |
| 28 | Methyl | Naphtnalene-2-yl sulfonyl |
| 29 | Methyl | Piperidine-1-yl sulfonyl |
| 30 | Methyl | Morpholinosulfonyl |
| 31 | Methyl | 2-Cyanoacetyl |
| 32 | Hydrogen | (3-Cyanophenyl)sulfonyl |
| 33 | Ethyl | 2-Cyanoacetyl |
| 34 | Ethyl | (3-Cyanophenyl)sulfonyl |
| 35 | Cyclopropylmethyl | 2-Cyanoacetyl |
| 36 | Cyclopropylmethyl | (3-Cyanophenyl)sulfonyl |

| Example | X | $R^1$ | $R^2$ |
|---|---|---|---|
| 37 | Nitrogen | Methyl | 1-(2-Cyanoacetyl)piperidine-4-yl |
| 38 | Nitrogen | Methyl | 1-(Phenylsulfonyl)piperidine-4-yl |
| 39 | Nitrogen | Methyl | 1-(3-Cyanophenylsulfonyl)piperidine-4-yl |
| 40 | Nitrogen | Methyl | 1-(2-Cyanoacetyl)piperidine-3-yl |
| 41 | Nitrogen | Methyl | 1-(3-Cyanophenylsulfonyl)piperidine-3-yl |
| 42 | Nitrogen | Methyl | 1-(3-Cyanophenylsulfonyl)-4-methyl-piperidine-3-yl |
| 43 | Nitrogen | Methyl | 1-(2-Cyanoacetyl)-3,3-dimethylpyrrolidine-4-yl |
| 44 | Nitrogen | Methyl | 1-(2-Cyanoacetyl)-3,3-dimethylpyrrolidine-4-yl |
| 45 | Oxygen | — | 1-(2-Cyanoacetyl)piperidine-4-yl |
| 46 | Oxygen | — | 1-(3-Cyanophenylsulfonyl)piperidine-4-yl |
| 47 | Oxygen | — | [1-(2-Cyanoacetyl)piperidine-3-yl]methyl |
| 48 | Oxygen | — | [1-(3-Cyanophenylsulfonyl)piperidine-3-yl]methyl |
| 49 | Nitrogen | 6-(2-Cyanoacetyl)-(4aR,7aR)-octahydro-6H-pyrrolo[3,4-b]pyridine-1-yl, with nitrogen as X | |

-continued

| Example | X | R¹ | R² |
|---|---|---|---|
| 50 | Nitrogen | | 6-(2-Cyanoacetyl)-(4aS,7aS)-octahydro-6H-pyrrolo[3,4-b]pyridine-1-yl, with nitrogen as X |

Test Example 1: JAK Inhibitory Effect

1. In-Vitro Kinase Inhibition Test
(1) Dilution of Kinase
Human-derived JAK1, JAK2, JAK3 and TYK2 (Millipore, Germany) were used as kinases. Each kinase was diluted with an appropriate buffer as described below, and then mixed with reaction reagents.

(1.1) Composition of JAK1 Dilution Buffer
Tris(hydroxymethyl)aminomethane (TRIS) and ethylenediaminetetraacetic acid (EDTA) were dissolved in deionized water at a concentration of 20 mM and 0.2 mM, respectively, and then, per 100 mL of the solution, 100 µL of β-mercaptoethanol, 10 µL of Brij-35™, and 5 mL glycerol were added, thereby preparing a JAK1 dilution buffer.

(1.2) Composition of JAK2, JAK3, and TYK2 Dilution Buffer
3-morpholinopropane-1-sulfonic acid (MOPS) and EDTA were dissolved in deionized water at a concentration of 20 mM and 1 mM, respectively, and then 100 µL of β-mercaptoethanol, 10 µL of Brij-35™, 5 mL of glycerol, and 100 mg of bovine serum albumin (BSA), each per 100 mL of the solution, were added to the solution, thereby preparing a dilution buffer for JAK2, JAK3, and TYK2.

(2) Preparation of Compounds and Experimental Method
Each compound was dissolved in a 100%-DMSO solution at a concentration of about 50 µM. This prepared solution was reacted with reaction reagents in each well of a 96-well plate until a final concentration of the compound reached 1 µM. A detailed experimental method for each kinase is as follows.

(2.1) JAK1
Final concentrations of materials in 25 µL of a reaction solution are shown in Table 1.

TABLE 1

| Materials | Concentration |
|---|---|
| Human JAK1 | 1 unit |
| Tris HCl (pH 7.5) | 20 mM |
| EDTA | 0.2 mM |
| Peptide of SEQ ID NO: 1/100 mM HEPES | 1 mM |
| MgAcetate (available from BDH, Cat.# 101484T) | 10 mM |
| γ-$^{33}$P-ATP | 2 mM |
| Test compound | 1 uM |

γ-$^{33}$P-ATP prepared from non-radiolabeled ATP (available from Sigma, Cat. no. A-7699) was used. After reaction at room temperature for about 40 minutes, the reaction was stopped by adding 5 µL of a 3 (v/v) % phosphoric acid solution. After the termination of the reaction, 10 µL of the reaction solution was dropped onto a GF/P30 filtermat (PerkinElmer™, 1450-523), which was then washed three times with a 75-mM phosphoric acid solution for about 5 minutes, followed by methanol drying and scintillation assay. Methanol drying is a drying process that uses an azeotropic effect, and is performed by adding methanol to an aqueous solution.

(2.2) JAK2
Final concentrations of materials in 25 µL of a reaction solution are shown in Table 2.

TABLE 2

| Materials | Concentration |
|---|---|
| Human JAK2 | 1 unit |
| MOPS (pH 7.0) | 8 mM |
| EDTA | 0.2 mM |
| Peptide of SEQ ID NO: 2/50 mM Tris pH 8.0 | 100 uM |
| MgAcetate (available from BDH, Cat.# 101484T) | 10 mM |
| γ-$^{33}$P-ATP | 2 mM |
| Test compound | 1 uM |

γ-$^{33}$P-ATP prepared from non-radiolabeled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay.

(2.3) JAK3
Final concentrations of materials in 25 uL of the reaction solution are shown in Table 3.

TABLE 3

| Materials | Concentration |
|---|---|
| Human JAK3 | 1 unit |
| MOPS (pH 7.0) | 8 mM |
| EDTA | 0.2 mM |
| Peptide of SEQ ID NO: 3/20 mM MOPS pH 7.0 | 50 uM |
| MgAcetate (available from BDH, Cat.# 101484T) | 10 mM |
| γ-$^{33}$P-ATP | 2 mM |
| Test compound | 1 uM |

γ-$^{33}$P-ATP prepared from non-radiolabeled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay.

(2.4) TYK2
Final concentrations of materials in 25 uL of the reaction solution are shown in Table 4.

TABLE 4

| Materials | Concentration |
|---|---|
| Human TYK2 | 1 unit |
| MOPS (pH7.0) | 8 mM |

TABLE 4-continued

| Materials | Concentration |
|---|---|
| EDTA | 0.2 mM |
| Peptide of SEQ ID NO: 4/water | 250 uM |
| MgAcetate (available from BDH, Cat.# 101484T) | 10 mM |
| γ-$^{33}$P-ATP | 2 mM |
| Test compound | 1 uM |

γ-$^{33}$P-ATP prepared from non-radiolabeled ATP (available from Sigma, Cat. no. A-7699) was used. After reaction for about 40 minutes at room temperature, the reaction was stopped by adding 5 uL of a 3% (v/v) phosphoric acid solution. After the termination of the reaction, 10 uL of the solution was spotted onto a GF/P30 filtermat (available from PerkinElmer™, 1450-523), and then washed three times for about 5 minutes in a 75 mM phosphoric acid solution, followed by methanol drying and scintillation assay.

(2.5) IC$_{50}$ Value Measurement

Kinase-activity inhibitory effects of some of the compounds of Examples 1 to 48 (for example, Examples 1 and 38) for JAK1, JAK2, JAK3, and TYK2 were measured at various concentrations by the above-described method, and IC$_{50}$ values were determined. The IC$_{50}$ values of the test compounds were calculated from % inhibition values of the compounds, by the Cheng-Prusoff method (*Biochem. Pharmacol.*, 1973, 22(23), 3099-3108)).

(3) Test Results

Tables 5 and 6 show the results of measuring JAK1, JAK2, JAK3, and TYK2 phosphorylation inhibitory levels of the compounds synthesized in Examples 1 to 48, by the above-described method. In Tables 5 and 6, the numbers in the "Example" column, which are identification numbers of the examples, indicate the compounds synthesized in the corresponding examples, the values in the "JAK1", "JAK2", "JAK3", and "TYK2" columns represent kinase-phosphorylation inhibitory levels as a percentage (%) of the compounds synthesized in the corresponding examples at a 1 uM concentration. In Tables 5 and 6, negative values substantially indicate no inhibitory effect.

The inhibitory levels (% inhibition) represent a percentage of reduction in phosphorylation activity in each test group with respect to the phosphorylation activity of a corresponding kinase in a negative control group lacking any of the compounds synthesized in the examples.

% inhibition=[(Scintillation value of Test compound non-treatment group−Scintillation value of Test compound treatment group)/(Scintillation value of Test compound non-treatment group)]×100

As the control group, 1 uM of tofacitinib citrate (available from Hangzhou Tacon Co., Ltd.) was used. The % inhibition values of the control group for JAK1, JAK2, JAK3, and TYK2 were 99%, 98%, 99%, and 100%, respectively.

TABLE 5

| Example | JAK1 | JAK2 | JAK3 | TYK2 | JAK1/JAK2 |
|---|---|---|---|---|---|
| 1 | 97 | 70 | 20 | 84 | 1.39 |
| 2 | 91 | 42 | 39 | 58 | 2.17 |
| 3 | 52 | 6 | 4 | 8 | ∞ |
| 4 | 98 | 79 | 33 | 86 | 1.24 |
| 5 | 93 | 13 | 10 | 63 | 7.15 |
| 6 | 93 | 9 | 9 | 34 | 10.33 |
| 7 | 97 | 68 | 42 | 72 | 1.43 |

TABLE 5-continued

| Example | JAK1 | JAK2 | JAK3 | TYK2 | JAK1/JAK2 |
|---|---|---|---|---|---|
| 8 | 91 | 7 | 21 | 59 | 13.00 |
| 9 | 90 | 9 | 11 | 59 | 10.00 |
| 10 | 94 | 27 | 22 | 74 | 3.48 |
| 11 | 95 | 62 | 20 | 78 | 1.55 |
| 12 | 86 | 11 | 13 | 47 | 7.82 |
| 13 | 52 | 9 | 4 | 17 | 5.78 |
| 14 | 99 | 69 | 17 | 91 | 1.43 |
| 15 | 98 | 66 | 25 | 92 | 1.48 |
| 16 | 98 | 93 | 47 | 98 | 1.05 |
| 17 | 99 | 81 | 29 | 92 | 1.22 |
| 18 | 97 | 73 | 22 | 81 | 1.33 |
| 19 | 99 | 81 | 42 | 95 | 1.22 |
| 20 | 97 | 46 | 9 | 84 | 2.11 |
| 21 | 93 | 48 | 21 | 67 | 1.94 |
| 22 | 100 | 97 | 74 | 99 | 1.03 |
| 23 | 100 | 84 | 31 | 94 | 1.19 |
| 24 | 95 | 53 | 8 | 87 | 1.79 |
| 25 | 97 | 42 | 10 | 68 | 2.31 |
| 26 | 98 | 44 | 10 | 71 | 2.23 |
| 27 | 96 | 21 | 4 | 56 | 4.57 |
| 28 | 99 | 57 | 23 | 82 | 1.74 |
| 29 | 91 | 21 | 10 | 65 | 4.33 |
| 30 | 87 | 6 | 13 | 44 | 14.50 |
| 31 | 23 | −6 | 27 | 2 | ∞ |
| 32 | 67 | 29 | 3 | 30 | 2.31 |
| 33 | 97 | 91 | 63 | 94 | 1.07 |
| 34 | 97 | 86 | 19 | 92 | 1.13 |
| 35 | 88 | 34 | 14 | 37 | 2.59 |
| 36 | 87 | 40 | 10 | 57 | 2.18 |

TABLE 6

| Example | JAK1 | JAK2 | JAK3 | TYK2 | JAK1/JAK2 |
|---|---|---|---|---|---|
| 37 | 49 | 1 | 8 | −3 | 49.00 |
| 38 | 97 | 94 | 77 | 97 | 1.03 |
| 39 | 87 | 59 | 1 | 69 | 1.47 |
| 40 | 99 | 83 | 81 | 93 | 1.19 |
| 41 | 92 | 64 | 39 | 79 | 1.44 |
| 42 | 95 | 79 | 89 | 86 | 1.20 |
| 43 | 86 | 19 | 36 | 38 | 4.53 |
| 44 | 26 | −8 | 1 | −1 | ∞ |
| 45 | 35 | 5 | 14 | 10 | 7.00 |
| 47 | 30 | 10 | 16 | 20 | 3.00 |
| 48 | 25 | 17 | 19 | 7 | 1.47 |
| 49 | 54 | −7 | 1 | 21 | ∞ |
| 50 | 14 | −10 | 1 | 6 | ∞ |

Table 7 represents IC$_{50}$ values of the compounds of Examples 1 and 38 for JAK1, JAK2, JAK3, and TYK2 activity.

TABLE 7

| | IC$_{50}$ (nM) | | | |
|---|---|---|---|---|
| Example | JAK1 | JAK2 | JAK3 | TYK2 |
| 1 | 18.8 | 127.8 | >1000 | 110.8 |
| 38 | 4.2 | 19.0 | 147.4 | 18.8 |

Test Example 2: Anti-Inflammation Test Using Croton Oil-Induced Inflammation Model (1) Animal ICR mice (6-week old, male) were purchased from Japan SLC, Inc., and maintained under controlled lighting in a 12-hour light/dark cycle (07:00-19:00). The temperature was maintained at about 22° C., and the mice were allowed free access to feed and drinking water, but were restricted from the feed for 2 hours before administration of the test compound.

(2) Induction of Croton Oil-Induced Inflammation (Croton Oil-Induced Ear Edema)

Croton oil (available from Sigma-Aldrich, Cat. # C6719) as an edema inducer was diluted to about 0.2 (v/v) % with acetone (available from Sigma-Aldrich, Cat #650501). After 30 minutes from the oral administration of a dose of the test compound per body weight of each animal, each animal of the test groups was treated with croton oil by uniformly applying 20 of the croton oil to the inside and outside of the right ear of each test animal.

(3) Experimental Design

Anti-inflammatory efficacy of the compounds according to embodiments was determined using a croton oil-induced mouse animal model. The mice were randomly grouped with 10 mice per group. To determine the anti-inflammatory efficacy of test drugs (compounds), a negative control and each drug were orally administered once 30 minutes before croton oil treatment, as described above in (2). As an excipient of the drugs administered, an aqueous solution of 0.45 v/v % carboxymethyl cellulose (CMC) (available from Sigma Aldrich, Cat # C5678, 0.5 v/v % in deionized water) and 10 v/v % ethanol in deionized water was used. 1 mL of the excipient (per 100 g of weight) only was administered into the negative control group. For the positive control group, 1 mL of a solution of indomethacin and the excipient (100 mg/10 mL) was administered per 100 g of body weight (100 mg of indomethacin per 1 kg of body weight). Each test compound was prepared at a concentration of 100 mg/10 mL, and 1 mL of solution per 100 g of weight was administered (100 mg per 1 kg of weight). Indomethacin as a member of the non-steroidal anti-inflammatory drug (NASID) family exhibits an efficacy of reducing various inflammation, pains and fevers, and anti-inflammatory efficacy through inhibitory action on cyclooxygenase (COXs).

(4) Evaluation of Inflammation (Ear Edema) Model Test

Figure 2:
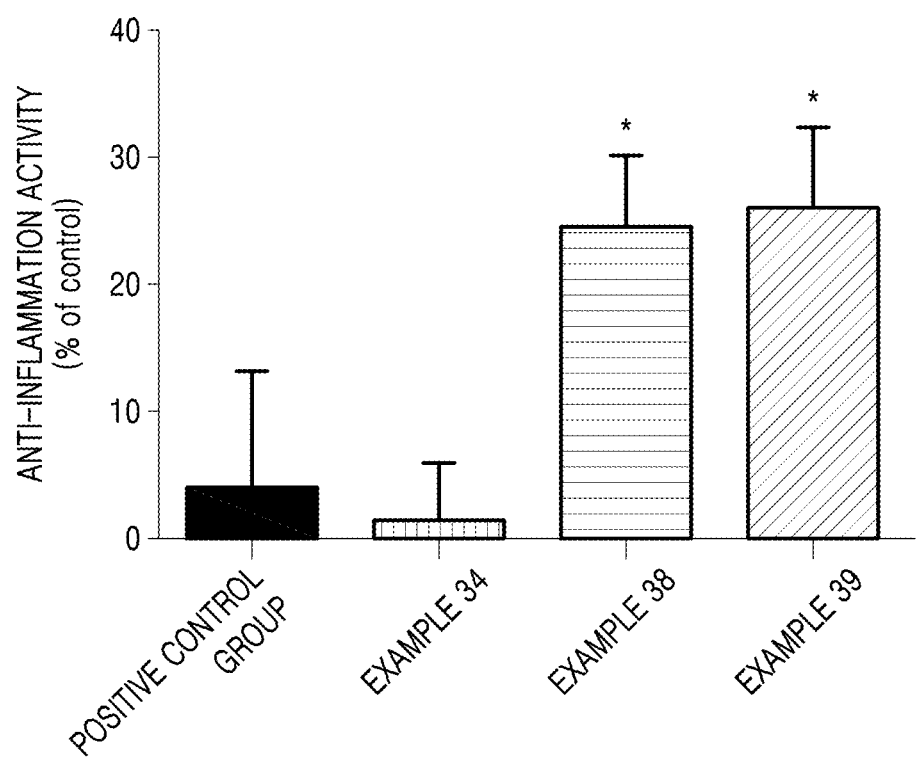

The degree of inflammation was determined by measuring the ear thicknesses of experimental animals using a digital outer diameter measuring device (Digimatic micrometer, Mitutoyo Corporation, Japan, Cat # MDC-25SB). The ear thickness measurement was performed after 4 hours from the treatment with croton oil. The thicknesses of a right ear treated with croton oil and a left ear treated with only acetone were measured, and a percentage of thickness increase in the right ear with respect to the thickness of the left ear was calculated. The results are shown in FIGS. 1 and 2.

Test Example 3: Pharmacokinetic Test

After a hydrochloride of the compound of Example 1 was orally or intravenously administered, blood was collected at intervals over 24 hours to analyze a pharmacokinetic profile. The compound of Example 49 (as a hydrochloride of the compound of Example 1) was used, and tofacitinib citrate (approved by EMA) was used as a comparative drug.

A dose of the compound was about 20 mg/kg, which was orally or intraveneously administered one time, followed by blood collection from the jugular veins of three mice at each of blood sampling intervals, i.e., 0, 0.25 (15 min), 0.5 (30 min), 1, 2, 4, 6, 12, and 24 hours from the administration, and measuring a drug concentration. The resulting pharmacokinetic profiles are shown in Table 8.

TABLE 8

| | Sample | | | |
|---|---|---|---|---|
| | Tofacitinib citrate (EMA) | | [Example 1] · HCl | |
| | Administration route | | | |
| | Oral administration | Intravenous injection | Oral administration | Intravenous injection |
| No. of test amimals/Sex | 4/male | 4/male | 3/male | 3/male |
| Dose (mg/kg) | 10 | 5 | 20 | 20 |
| $C_{max}$ (ng/mL) | 2400 | — | 4530 | 15490 |
| $T_{max}$ (h) | 0.31 | — | 0.50 | — |
| $AUC_{0 \rightarrow t}$ (ng · h/mL) | 2750 | 3180 | 13060 | 18910 |
| $AUC_{0 \rightarrow t}$/Dose (kg · h/mL) | 0.275 | 0.636 | 0.653 | 0.946 |
| $t_{1/2}$ (h) | 2.0 | 2.8 | 2.78 | 1.97 |
| Bioavailability (%) | 43.3 | — | 69.1 | — |

According to the test results, since the longer the half-life period of a drug, the longer the administration interval becomes, the compound according to an embodiment was found to have a remarkably increased administration interval, compared to conventional tofacitinib, and thus improved patients' medication compliance.

While this invention has been particularly shown and described with reference to preferred embodiments thereof, it will be understood by those skilled in the art that various changes in form and details may be made therein without departing from the spirit and scope of the invention as defined by the appended claims. The disclosed embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. A compound of Formula 1, or a pharmaceutically acceptable salt, solvate, or stereoisomer thereof,

[Formula 1]

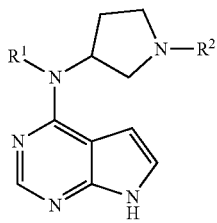

wherein, in Formula 1, $R^1$ is hydrogen, $C_{1-2}$ alkyl, or cyclopropylmethyl;

$R^2$ is 2-cyanoacetyl, 2-cyanoethyl, butyl, 2-azidoacetyl, 3-methylbutanoyl, isobutoxycarbonyl, anilinocarbonyl, methylsulfonyl, (trifluoromethyl)sulfonyl, ethylsulfonyl, propylsulfonyl, isopropylsulfonyl, (1-methyl-1H-imidazole-4-yl)sulfonyl, phenylsulfonyl, (2-fluorophenyl)sulfonyl, (3-fluorophenyl)sulfonyl, (4-fluorophenyl)sulfonyl, (2-cyanophenyl)sulfonyl, (3-cyanophenyl)sulfonyl, (4-cyanophenyl)sulfonyl, (2-nitrophenyl)sulfonyl, (3-nitrophenyl)sulfonyl, (4-nitrophenyl)sulfonyl, m-tolylsulfonyl, tosyl, (4-methoxyphenyl)sulfonyl, ((4-trifluoromethyl)phenyl)sulfonyl, naphthalene-2-ylsulfonyl, piperidine-1-ylsulfonyl, or morpholinosulfonyl.

2. The compound according to claim 1, or a pharmaceutically acceptable salt, solvate, or stereoisomer thereof, wherein the compound of Formula 1 is (R)-3-(3-(methyl(7H-pyrrolo[2,3-d]pyrimidine-4-yl)amino)pyrrolidine-1-yl)-3-oxopropanenitrile;

(R)-3-(3-(methyl(7H-pyrrolo[2,3-d]pyrimidine-4-yl)amino)pyrrolidine-1-yl)propanenitrile;

(R)—N-(1-butylpyrrolidine-3-yl)-N-methyl-7H-pyrrolo[2,3-d]pyrimidine-4-amine;

(R)-2-azido-1-(3-(methyl(7H-pyrrolo[2,3-d]pyrimidine-4-yl)amino)pyrrolidine-1-yl)ethane-1-one;

(R)-3-methyl-1-(3-(methyl(7H-pyrrolo[2,3-d]pyrimidine-4-yl)amino)pyrrolidine-1-yl)butane-1-one;

isobutyl (R)-3-(methyl(7H-pyrrolo[2,3-d]pyrimidine-4-yl)amino)pyrrolidine-1-carboxylate;

(R)-3-(methyl(7H-pyrrolo[2,3-d]pyrimidine-4-yl)amino)-N-phenylpyrrolidine-1-carboxamide;

(R)—N-methyl-N-(1-(methylsulfonyl)pyrrolidine-3-yl)-7H-pyrrolo[2,3-d]pyrimidine-4-amine;

(R)—N-methyl-N-(1-(((trifluoromethyl)sulfonyl)pyrrolidine-3-yl)-7H-pyrrolo[2,3-d]pyrimidine-4-amine;

(R)—N-(1-(ethylsulfonyl)pyrrolidine-3-yl)-N-methyl-7H-pyrrolo[2,3-d]pyrimidine-4-amine;

(R)—N-methyl-N-(1-(propylsulfonyl)pyrrolidine-3-yl)-7H-pyrrolo[2,3-d]pyrimidine-4-amine;
(R)—N-(1-(isopropylsulfonyl)pyrrolidine-3-yl)-N-methyl-7H-pyrrolo[2,3-d]pyrimidine-4-amine;
(R)—N-methyl-N-(1-((1-methyl-1H-imidazole-4-yl)sulfonyl)pyrrolidine-3-yl)-7H-pyrrolo[2,3-d]pyrimidine-4-amine;
(R)—N-methyl-N-(1-(phenylsulfonyl)pyrrolidine-3-yl)-7H-pyrrolo[2,3-d]pyrimidine-4-amine;
(R)—N-(1-((2-fluorophenyl)sulfonyl)pyrrolidine-3-yl)-N-methyl-7H-pyrrolo[2,3-d]pyrimidine-4-amine;
(R)—N-(1-((3-fluorophenyl)sulfonyl)pyrrolidine-3-yl)-N-methyl-7H-pyrrolo[2,3-d]pyrimidine-4-amine;
(R)—N-(1-((4-fluorophenyl)sulfonyl)pyrrolidine-3-yl)-N-methyl-7H-pyrrolo[2,3-d]pyrimidine-4-amine;
(R)-2-((3-(methyl(7H-pyrrolo[2,3-d]pyrimidine-4-yl)amino)pyrrolidine-1-yl)sulfonyl)benzonitrile;
(R)-3-((3-(methyl(7H-pyrrolo[2,3-d]pyrimidine-4-yl)amino)pyrrolidine-1-yl)sulfonyl)benzonitrile;
(R)-4-((3-(methyl(7H-pyrrolo[2,3-d]pyrimidine-4-yl)amino)pyrrolidine-1-yl)sulfonyl)benzonitrile;
(R)—N-methyl-N-(1-((2-nitrophenyl)sulfonyl)pyrrolidine-3-yl)-7H-pyrrolo[2,3-d]pyrimidine-4-amine;
(R)—N-methyl-N-(1-((3-nitrophenyl)sulfonyl)pyrrolidine-3-yl)-7H-pyrrolo[2,3-d]pyrimidine-4-amine;
(R)—N-methyl-N-(1-((4-nitrophenyl)sulfonyl)pyrrolidine-3-yl)-7H-pyrrolo[2,3-d]pyrimidine-4-amine;
(R)—N-methyl-N-(1-(m-tolylsulfonyl)pyrrolidine-3-yl)-7H-pyrrolo[2,3-d]pyrimidine-4-amine;
(R)—N-methyl-N-(1-tosylpyrrolidine-3-yl)-7H-pyrrolo[2,3-d]pyrimidine-4-amine;
(R)—N-(1-((4-methoxyphenyl)sulfonyl)pyrrolidine-3-yl)-N-methyl-7H-pyrrolo[2,3-d]pyrimidine-4-amine;
(R)—N-methyl-N-(1-((4-(trifluoromethyl)phenyl)sulfonyl)pyrrolidine-3-yl)-7H-pyrrolo[2,3-d]pyrimidine-4-amine;
(R)—N-methyl-N-(1-(naphthalene-2-ylsulfonyl)pyrrolidine-3-yl)-7H-pyrrolo[2,3-d]pyrimidine-4-amine;
(R)—N-methyl-N-(1-(piperidine-1-ylsulfonyl)pyrrolidine-3-yl)-7H-pyrrolo[2,3-d]pyrimidine-4-amine;
(R)—N-methyl-N-(1-(morpholinosulfonyl)pyrrolidine-3-yl)-7H-pyrrolo[2,3-d]pyrimidine-4-amine;
(S)-3-(3-(methyl(7H-pyrrolo[2,3-d]pyrimidine-4-yl)amino)pyrrolidine-1-yl)-3-oxopropanenitrile;
(R)-3-((3-((7H-pyrrolo[2,3-d]pyrimidine-4-yl)amino)pyrrolidine-1-yl)sulfonyl)benzonitrile;
(R)-3-(3-(ethyl(7H-pyrrolo[2,3-d]pyrimidine-4-yl)amino)pyrrolidine-1-yl)-3-oxopropanenitrile;
(R)-3-((3-(ethyl(7H-pyrrolo[2,3-d]pyrimidine-4-yl)amino)pyrrolidine-1-yl)sulfonyl)benzonitrile;
(R)-3-(3-((cyclopropylmethyl)(7H-pyrrolo[2,3-d]pyrimidine-4-yl)amino)pyrrolidine-1-yl)-3-oxopropanenitrile; or
(R)-3-((3-((cyclopropylmethyl)(7H-pyrrolo[2,3-d]pyrimidine-4-yl)amino)pyrrolidine-1-yl)sulfonyl)benzonitrile.

3. A compound of Formula 2, or a pharmaceutically acceptable salt, solvate, or stereoisomer thereof,

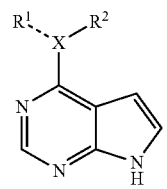

[Formula 2]

wherein, in Formula 2,
X is nitrogen or oxygen,
-- is a single bond when X is nitrogen, or is absent when X is oxygen, and
$R^1$ is methyl,
$R^2$ is 1-(2-cyanoacetyl)piperidine-4-yl, 1-(phenylsulfonyl)piperidine-4-yl, 1-(3-cyanophenylsulfonyl)piperidine-4-yl, 1-(2-cyanoacetyl)piperidine-3-yl, 1-(3-cyanophenylsulfonyl)piperidine-3-yl, 1-(3-cyanophenylsulfonyl)-4-methyl-piperidine-3-yl, 1-(2-cyanoacetyl)-3,3-dimethylpyrrolidine-4-yl, [1-(2-cyanoacetyl)piperidine-3-yl]methyl, or [1-(3-cyanophenylsulfonyl)piperidine-3-yl]methyl, or
$R^1$ and $R^2$, together with X, form 6-(2-cyanoacetyl)octahydro-6H-pyrrolo-[3,4-b]pyridine-1-yl.

4. The compound according to claim 3, or a pharmaceutically acceptable salt, solvate, or stereoisomer thereof, wherein the compound of Formula 2 is
3-(4-(methyl(7H-pyrrolo[2,3-d]pyrimidine-4-yl)amino)piperidine-1-yl)-3-oxopropanenitrile;
N-methyl-N-(1-(phenylsulfonyl)piperidine-4-yl)-7H-pyrrolo[2,3-d]pyrimidine-4-amine;
3-((4-(methyl(7H-pyrrolo[2,3-d]pyrimidine-4-yl)amino)piperidine-1-yl)sulfonyl)benzonitrile;
(R)-3-(3-(methyl(7H-pyrrolo[2,3-d]pyrimidine-4-yl)amino)piperidine-1-yl)-3-oxopropanenitrile;
(R)-3-((3-(methyl(7H-pyrrolo[2,3-d]pyrimidine-4-yl)amino)piperidine-1-yl)sulfonyl)benzonitrile;
3-(((3R,4R)-4-methyl-3-(methyl(7H-pyrrolo[2,3-d]pyrimidine-4-yl)amino)piperidine-1-yl)sulfonyl)benzonitrile;
(R)-3-(3,3-dimethyl-4-(methyl(7H-pyrrolo[2,3-d]pyrimidine-4-yl)amino)pyrrolidine-1-yl)-3-oxopropanenitrile;
(S)-3-(3,3-dimethyl-4-(methyl(7H-pyrrolo[2,3-d]pyrimidine-4-yl)amino)pyrrolidine-1-yl)-3-oxopropanenitrile;
3-(4-((7H-pyrrolo[2,3-d]pyrimidine-4-yl)oxy)piperidine-1-yl)-3-oxopropanenitrile;
3-((4-((7H-pyrrolo[2,3-d]pyrimidine-4-yl)oxy)piperidine-1-yl)sulfonyl)benzonitrile;
3-(3-(((7H-pyrrolo[2,3-d]pyrimidine-4-yl)oxy)methyl)piperidine-1-yl)-3-oxopropanenitrile;
3-((3-(((7H-pyrrolo[2,3-d]pyrimidine-4-yl)oxy)methyl)piperidine-1-yl)sulfonyl)benzonitrile;
3-((4aR,7aR)-1-(7H-pyrrolo[2,3-d]pyrimidine-4-yl)octahydro-6H-pyrrolo[3,4-b]pyridine-6-yl)-3-oxopropanenitrile; and
3-((4aS,7aS)-1-(7H-pyrrolo[2,3-d]pyrimidine-4-yl)octahydro-6H-pyrrolo[3,4-b]pyridine-6-yl)-3-oxopropanenitrile.

5. A pharmaceutical composition for the treatment of a disease associated with a Janus kinase (JAK), the pharmaceutical composition comprising the compound according to claim 1 or a pharmaceutically acceptable salt, solvate, or stereoisomer thereof.

6. The pharmaceutical composition according to claim 5, wherein the disease is an autoimmune disease, an immune system dysfunction, a viral disease, or a cancer.

7. The pharmaceutical composition according to claim 6, wherein the autoimmune disease is a skin disease, multiple sclerosis, rheumatoid arthritis, juvenile arthritis, type I diabetes, lupus, psoriasis, inflammatory bowel disease, Crohn's disease, or an autoimmune thyroid disease; the immune system dysfunction is an allograft rejection, a graft-versus-host disease, an allograft rejection reaction, or a graft-versus-host reaction; the viral disease is Epstein-Barr virus (EBV), hepatitis B, hepatitis C, HIV, HTLV 1, chickenpox, herpes zoster virus (VZV), or human papillomavirus (HPV); and the cancer is prostate cancer, lymphoma, leukemia, or multiple myeloma.

8. A method of inhibiting the activity of a Janus kinase (JAK), the method comprising contacting the JAK with the compound according to claim 1 or a pharmaceutically acceptable salt, solvate, or stereoisomer thereof.

9. The method according to claim 8, wherein the activity of JAK1 is selectively inhibited over the activity of JAK2.

10. A method of treating a disease associated with a Janus kinase (JAK) in a subject, the method comprising administering a therapeutically effective amount of the compound according to claim 1 or a pharmaceutically acceptable salt, solvate, or stereoisomer thereof to the subject,
wherein the disease is an autoimmune disease, an immune system dysfunction, or a cancer;
wherein the autoimmune disease is autoimmune skin disease, inflammatory skin disease, multiple sclerosis, rheumatoid arthritis, juvenile arthritis, type I diabetes, lupus, psoriasis, inflammatory bowel disease, Crohn's disease, or an autoimmune thyroid disease;
wherein the immune system dysfunction is an allograft rejection or graft-versus-host disease; and
wherein the cancer is prostate cancer, lung cancer, lymphoma, leukemia, or multiple myeloma.

11. A pharmaceutical composition for the treatment of a disease associated with a JAK, the pharmaceutical composition comprising the compound according to claim 2 or a pharmaceutically acceptable salt, solvate, or stereoisomer thereof.

12. A pharmaceutical composition for the treatment of a disease associated with a JAK, the pharmaceutical composition comprising the compound according to claim 3 or a pharmaceutically acceptable salt, solvate, or stereoisomer thereof.

13. A pharmaceutical composition for the treatment of a disease associated with a JAK, the pharmaceutical composition comprising the compound according to claim 4 or a pharmaceutically acceptable salt, solvate, or stereoisomer thereof.

14. A method of inhibiting the activity of a JAK, the method comprising contacting the JAK with the compound according to claim 2 or a pharmaceutically acceptable salt, solvate, or stereoisomer thereof.

15. A method of inhibiting the activity of a JAK, the method comprising contacting the JAK with the compound according to claim 3 or a pharmaceutically acceptable salt, solvate, or stereoisomer thereof.

16. A method of inhibiting the activity of a JAK, the method comprising contacting the JAK with the compound according to claim 4 or a pharmaceutically acceptable salt, solvate, or stereoisomer thereof.

17. A method of treating a disease associated with a JAK in a subject, the method comprising administering a therapeutically effective amount of the compound according to claim 2 or a pharmaceutically acceptable salt, solvate, or stereoisomer thereof to the subject,
wherein the disease is an autoimmune disease, an immune system dysfunction, or a cancer;
wherein the autoimmune disease is autoimmune skin disease, inflammatory skin disease, multiple sclerosis, rheumatoid arthritis, juvenile arthritis, type I diabetes, lupus, psoriasis, inflammatory bowel disease, Crohn's disease, or an autoimmune thyroid disease;
wherein the immune system dysfunction is an allograft rejection or graft-versus-host disease; and
wherein the cancer is prostate cancer, lung cancer, lymphoma, leukemia, or multiple myeloma.

18. A method of treating a disease associated with a JAK in a subject, the method comprising administering a therapeutically effective amount of the compound according to claim 3 or a pharmaceutically acceptable salt, solvate, or stereoisomer thereof to the subject,
wherein the disease is an autoimmune disease, an immune system dysfunction, or a cancer;
wherein the autoimmune disease is autoimmune skin disease, inflammatory skin disease, multiple sclerosis, rheumatoid arthritis, juvenile arthritis, type I diabetes, lupus, psoriasis, inflammatory bowel disease, Crohn's disease, or an autoimmune thyroid disease;
wherein the immune system dysfunction is an allograft rejection or graft-versus-host disease; and
wherein the cancer is prostate cancer, lung cancer, lymphoma, leukemia, or multiple myeloma.

* * * * *